United States Patent
Malik

(10) Patent No.: US 11,518,981 B2
(45) Date of Patent: Dec. 6, 2022

(54) METHODS OF ENHANCING ENGRAFTMENT ACTIVITY OF HEMATOPOIETIC STEM CELLS

(71) Applicant: CHILDREN'S HOSPITAL MEDICAL CENTER, Cincinnati, OH (US)

(72) Inventor: Punam Malik, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 476 days.

(21) Appl. No.: 16/481,294

(22) PCT Filed: Jan. 26, 2018

(86) PCT No.: PCT/US2018/015547
§ 371 (c)(1),
(2) Date: Jul. 26, 2019

(87) PCT Pub. No.: WO2018/140791
PCT Pub. Date: Aug. 2, 2018

(65) Prior Publication Data
US 2019/0338249 A1 Nov. 7, 2019

Related U.S. Application Data

(60) Provisional application No. 62/451,594, filed on Jan. 27, 2017.

(51) Int. Cl.
*C12N 5/0789* (2010.01)
*A61K 35/28* (2015.01)

(52) U.S. Cl.
CPC ............ *C12N 5/0647* (2013.01); *A61K 35/28* (2013.01); *C12N 2501/02* (2013.01); *C12N 2501/999* (2013.01); *C12N 2510/00* (2013.01)

(58) Field of Classification Search
None
See application file for complete search history.

(56) References Cited

U.S. PATENT DOCUMENTS

| | | |
|---|---|---|
| 2012/0276064 A1 | 11/2012 | Blau et al. |
| 2013/0171110 A1 | 7/2013 | Woods et al. |
| 2015/0166969 A1 | 6/2015 | Takeuchi et al. |
| 2015/0174169 A1 | 6/2015 | Genovese et al. |
| 2016/0024474 A1 | 1/2016 | Conway et al. |
| 2016/0030478 A1 | 2/2016 | Pelus et al. |
| 2018/0187156 A1 | 7/2018 | Rossi et al. |
| 2018/0187173 A1 | 7/2018 | Cost et al. |

FOREIGN PATENT DOCUMENTS

| | | |
|---|---|---|
| WO | WO 2012/141971 A2 | 10/2012 |
| WO | WO 2014/026110 A2 | 2/2014 |
| WO | WO 2016/041080 A1 | 3/2016 |
| WO | WO 2016/210292 A1 | 12/2016 |

OTHER PUBLICATIONS

Cutler et al. "Prostaglandin-modulated umbilical cord blood hematopoietic stem cell transplantation." Blood, The Journal of the American Society of Hematology 122.17 (2013): 3074-3081. (Year: 2013).*
Cartier et al., Hematopoietic stem cell gene therapy with a lentiviral vector in X-linked adrenoleukodystrophy. Science. Nov. 6, 2009;326(5954):818-23.
Goessling et al., Prostaglandin E2 enhances human cord blood stem cell xenotransplants and shows long-term safety in preclinical nonhuman primate transplant models. Cell Stem Cell. Apr. 8, 2011;8(4):445-58.
Gonsalves et al., Erythropoietin-mediated expression of placenta growth factor is regulated via activation of hypoxia-inducible factor-1α and post-transcriptionally by miR-214 in sickle cell disease. Biochem J. Jun. 15, 2015;468(3):409-23, Epub Apr. 16, 2015.
Ito et al., Reactive Oxygen Species Act Through p38 MAPK to Limit the Lifespan of Hematopoietic Stem Cells. Nature Medicine. Apr. 2006;12(4):446-451.
Li et al., Genomic editing of the HIV-1 coreceptor CCR5 in adult hematopoietic stem and progenitor cells using zinc finger nucleases. Mol Ther. Jun. 2013;21(6):1259-69. Epub Apr. 16, 2013.
Ludin et al., Reactive oxygen species regulate hematopoietic stem cell self-renewal, migration and development, as well as their bone marrow microenvironment. Antioxid Redox Signal. Oct. 10, 2014;21(11):1605-19. Epub Jun. 26, 2014.
Luo et al., Rapamycin Enhances Long-Term Hematopoietic Reconstitution of ex vivo Expanded Mouse Hematopoietic Stem Cells by Inhibiting Senescene. Transplantation. Jan. 1, 2014;97(1):20-9.
Millington et al., Towards a clinically relevant lentiviral transduction protocol for primary human CD34 hematopoietic stem/progenitor cells. PLoS One. Jul. 30, 2009;4(7):e6461(1-10).
Piccoli et al., The hypoxia-inducible factor is stabilized in circulating hematopoietic stem cells under normoxic conditions. FEBS Lett. Jun. 26, 2007;581(16):3111-9, Epub Jun. 6, 2007.
Santoni De Sio et al., Proteasome activity restricts lentiviral gene transfer into hematopoietic stem cells and is down-regulated by cytokines that enhance transduction. Blood. Jun. 1, 2006;107(11):4257-65. Epub Feb. 9, 2006.
Scott, Stem cell plasticity or fusion: two approaches to targeted cell therapy. Blood Cells Mol Dis. Jan.-Feb. 2004;32(1):65-7.
Speth et al., Pharmacologic increase in HIF1α enhances hematopoietic stem and progenitor homing and engraftment. Blood. Jan. 9, 2014;123(2):203-7, Epub Oct. 28, 2013, Supplementary Information.

(Continued)

Primary Examiner — Emily A Cordas
(74) Attorney, Agent, or Firm — McDermott Will & Emery

(57) ABSTRACT

Provided herein are methods for preparing hematopoietic stem cells (HSCs) having enhanced engraftment activity, for example, by contacting HSCs in the presence of a p38 MAPK inhibitor and a HIF-1a stabilizer.

18 Claims, 35 Drawing Sheets

(56) References Cited

OTHER PUBLICATIONS

Thalheimer et al., Cytokine-regulated GADD45G induces differentiation and lineage selection in hematopoietic stem cells. Stem Cell Reports. Jun. 19, 2014;3(1):34-43.

Verma et al., Activation of the p38 mitogen-activated protein kinase mediates the suppressive effects of type I interferons and transforming growth factor-beta on normal hematopoiesis. J Biol Chem. Mar. 8, 2002;277(10):7726-35. Epub Dec. 31, 2001.

Wang et al., Inhibition of p38 mitogen-activated protein kinase promotes ex vivo hematopoietic stem cell expansion. Stem Cells Dev. Jul. 2011;20(7):1143-52, Epub Feb. 24, 2011.

Xiao et al., The possible mechanisms underlying the impairment of HIF-1α pathway signaling in hyperglycemia and the beneficial effects of certain therapies. Int J Med Sci. Aug. 22, 2013;10(10):1412-21.

Zou et al., Inhibition of p38 MAPK Activity Promotes ex vivo Expansion of Human Cord Blood Hematopoietic Stem Cells. Ann. Hematol. Jan. 19, 2012;91:813-23.

\* cited by examiner

METHODS OF ENHANCING ENGRAFTMENT ACTIVITY OF HEMATOPOIETIC STEM CELLS

CROSS-REFERENCE TO RELATED APPLICATIONS

This application is a National Stage Application under 35 U.S.C. § 371 of PCT International Application No. PCT/US2018/015547, filed Jan. 26, 2018, which claims the benefit under 35 U.S.C. § 119(e) of U.S. provisional application No. 62/451,594, filed Jan. 27, 2017, the contents of each of which are incorporated by reference herein in their entirety.

STATEMENT REGARDING FEDERALLY SPONSORED RESEARCH OR DEVELOPMENT

This invention was made with Government support under NIH Grant Number DK102890 awarded by the National Institutes of Health. The Government has certain rights in this invention.

TECHNICAL FIELD

Provided herein are methods for preparing stem cells, e.g., hematopoietic stem cells (HSCs), having enhanced engraftment activity.

BACKGROUND

Hematopoietic stem cells (HSC) are a unique and rare population of cells that have the ability to reconstitute the whole hematopoietic system and to undergo self-renewal for the maintenance of their population. Gene therapy (GT), which involves transferring a gene into or editing a gene in HSCs, offers an attractive treatment strategy for curing monogenic disorders or hematopoietic disorders. It also offers an attractive alternative to allogenic hematopoietic stem cell transplantation to cure patients in need thereof who lack a suitable transplant donor. However, GT requires ex vivo manipulation and culture of HSCs, which results in a large amount of HSC loss as they age and lose their lymphoid phenotype.

Currently, the numbers of human HSCs that repopulate after autologous transplants are a major limitation to effective gene transfer. Myeloablative conditioning is therefore often required to destroy resident HSCs, giving an engraftment advantage to the limited numbers of genetically-manipulated HSCs following ex vivo manipulation.

Accordingly, there is a need for development of a method to maintain sternness of HSCs during ex vivo genetic manipulation and/or cell culture, thereby increasing their engraftment activity and thus the therapeutic success of gene therapy.

SUMMARY

The present disclosure is based, at least in part, on the unexpected discovery that inhibiting activation of p38 mitogen-activated protein kinase (MAPK) in stem cells, for example, using a p38 MAPK inhibitor such as doramapimod, in conjunction with stabilizing hypoxia inducible factor-1α (HIF-1α), for example, using a HIF-1α stabilizer such as prostaglandin E2 (PGE2), successfully reduced the loss of stem cells (e.g., dividing stem cells such as dividing HSCs) during in vitro or ex vivo culture, as compared to the single treatment with a p38 MAPK inhibitor or a HIF-1α stabilizer alone. Hence, the combined treatment of stem cells (e.g., dividing stem cells such as dividing HSCs) with a p38 MAPK inhibitor and a HIF-1α stabilizer unexpectedly increased engraftment of the cultured stem cells in vivo.

Accordingly, one aspect of the present disclosure features a method for preparing stem cells, such as hematopoietic stem cells (HSCs), having enhanced engraftment activity. The method comprises culturing stem cells (e.g., HSCs) in the presence of an effective amount of a p38 MAPK inhibitor and an effective amount of a HIF-1α stabilizer. In some embodiments, the HSCs may be cultured in a culture medium containing both a p38 MAPK inhibitor and a HIF-1α stabilizer. The stem cells that are amenable to the methods described herein can be subjected to a genetic manipulation that induces a DNA double strand break (e.g., transduction of an integration vector or genome editing). In some instances, the stem cells can be cycling or dividing stems cells (e.g., in S-G2M phase).

Any of the methods described herein may further comprise, prior to the culturing step, genetically manipulating the stem cells. The genetic manipulation can be performed in a cell-cycle independent or in a cell-cycle dependent manner. In some examples, the genetic manipulation may be performed during a cell division cycle. The genetic manipulation may comprise transducing the stem cells with an integrating vector. Examples of an integrating vector include, but are not limited to viral vectors such as retroviral vectors (e.g., lentiviral vectors). Alternatively or additionally, the genetic manipulation may comprise performing genome editing in the stem cells. The genome editing may involve uses of, e.g., but not limited to CRISPR-Cas9 systems, zinc finger nucleases (ZFN), homing endonucleases, meganucleases, and/or transcription activator-like effector-based nucleases (TALEN).

Any of the methods described herein may further comprise administering or transplanting to a subject in need thereof the HSCs that have been cultured in the presence of a p38 MAPK inhibitor and a HIF-1α stabilizer. For example, a dose of about 50,000 to about 500,000 HSCs (or even a lower dose such as about 50,000 to about 100,000 HSCs) that have been cultured in the presence of a p38 MAPK inhibitor and a HIF-1α stabilizer may be administered to the subject. The stem cells (e.g., HSCs) can be allogeneic stem cells (e.g., HSCs) or autologous stem cells (e.g., HSCs). The HSCs may be cultured for 1 to 7 days prior to their administration or transplantation into the subject. In some examples, the recipient subject is free of myeloablative chemotherapy conditioning or any other equivalent method that is capable of destroying resident HSCs in the recipient subject, prior to administration or transplantation of the HSCs.

In any methods described herein, the stem cells (e.g., HSCs) may be adult stem cells, which may be derived from bone marrow and/or peripheral blood cells of a suitable source (e.g., human). Alternatively, the stem cells may be derived from umbilical cord blood of a suitable source (e.g., human).

In any aspects described herein, the p38 MAPK inhibitor can be a protein, a nucleic acid, a small molecule, or a combination thereof. In some examples, the p38 MAPK inhibitor can be a p38 MAPK blocking agent (e.g., a small molecule that binds p38-α and blocks p38 MAPK signaling). Examples of the p39 MAPK inhibitor include, but are not limited to doramapimod (e.g., BIRB-796), ralimetinib (e.g., LY2228820 dimesylate), aminopyridine-based, ATP-competitive inhibitors of p38 MAPK (e.g., Vx702), pyridinyl imidazole inhibitors (e.g., SB203580), and any combinations thereof.

In any of the methods described herein, the amount of the p38 MAPK inhibitor can be effective to increase the proportion of stem cells (e.g., HSCs) in the G0 quiescent phase and to decrease the proportion of the stem cells (e.g., HSCs) in the S-G2-M phase before the first cell division cycle (e.g., 24 hours); to delay the transition of stem cells from G0 quiescent phase to S phase; and/or to reduce DNA damage response and repair (DDR) (e.g., reduced γH2AX levels) in the stem cells associated with cell culture and/or genetic manipulation. In some instances, the amount of the p38 MAPK inhibitor is selected to specifically decrease p38 phosphorylation in the stem cells with minimal or no other non-specific inhibition.

In any aspects described herein, the HIF-1α stabilizer can be a protein, a nucleic acid, a small molecule, or a combination thereof. In some examples, the HIF-1α stabilizer can stabilize HIF-1α protein and/or transcriptional activity without affecting messenger RNA (mRNA). In some examples, the HIF-1α stabilizer can increase HIF-1α gene expression. Examples of the HIF-1α stabilizer include, but are not limited to, prostaglandin E2 (PGE2) and its analog, e.g., 16-16 dimethyl PGE2 (dmPEG2), diethyl fumarate (DEF), and dimethyloxalyglycine (DMOG; also known as N-(methoxyoxoacetyl)-glycine), and any combinations thereof.

In any of the methods described herein, the amount of the HIF-1α stabilizer can be effective to stabilize HIF-1α protein and/or transcriptional activity in the stem cells (e.g., HSCs such as cycling or dividing HSCs); and/or to upregulate CXCR4 in the stem cells (e.g., HSCs such as cycling or dividing HSCs).

In any of the methods described herein, the combined amounts of the p38 MAPK inhibitor and HIF-1α stabilizer can be effective to reduce accumulation of the stem cells (e.g., HSCs such as cycling or dividing HSCs) in the G2M phase of the cell cycle; to reduce loss of long term repopulating potential (LTRP) in the stem cells; to reduce the myeloid skewing phenotype in the stem cells; and/or to promote engraftment of the HSCs transplanted to the subject.

In some instances, the effect(s) of the combination treatment of the stem cells (e.g., HSCs such as cycling or dividing HSCs) with a p38 MAPK inhibitor and a HIF-1α stabilizer may be synergistic. For example, the combination of a p38 MAPK inhibitor and a HIF-1α stabilize enhances in vivo engraftment of cycling or dividing stem cells that have undergone in vitro or ex vivo manipulation (e.g., cell culture and/or genetic manipulation), but absence of either molecule fails to do so.

In any of the methods described herein, the subject can be a human subject. In some embodiments, the subject is a human patient having a hematopoietic disorder. In some embodiments, the subject is a human patient having a monogenic disorder.

Also within the scope of the present disclosure is a composition for use in promoting engraftment of stem cells (e.g., HSCs) in a subject who is in need for a stem cell (e.g., HSC) transplantation. The composition comprises (i) any of the p38 MAPK inhibitors described herein; (ii) any of the HIF-1α stabilizer described herein; and (iii) stem cells such as hematopoietic stem cells. The composition may further comprise a cell culture medium. The subject can be a human patient having a hematopoietic disorder or a monogenic disorder.

The details of one or more embodiments of the disclosure are set forth in the description below. Other features or advantages of the present disclosure will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

Figure 1:
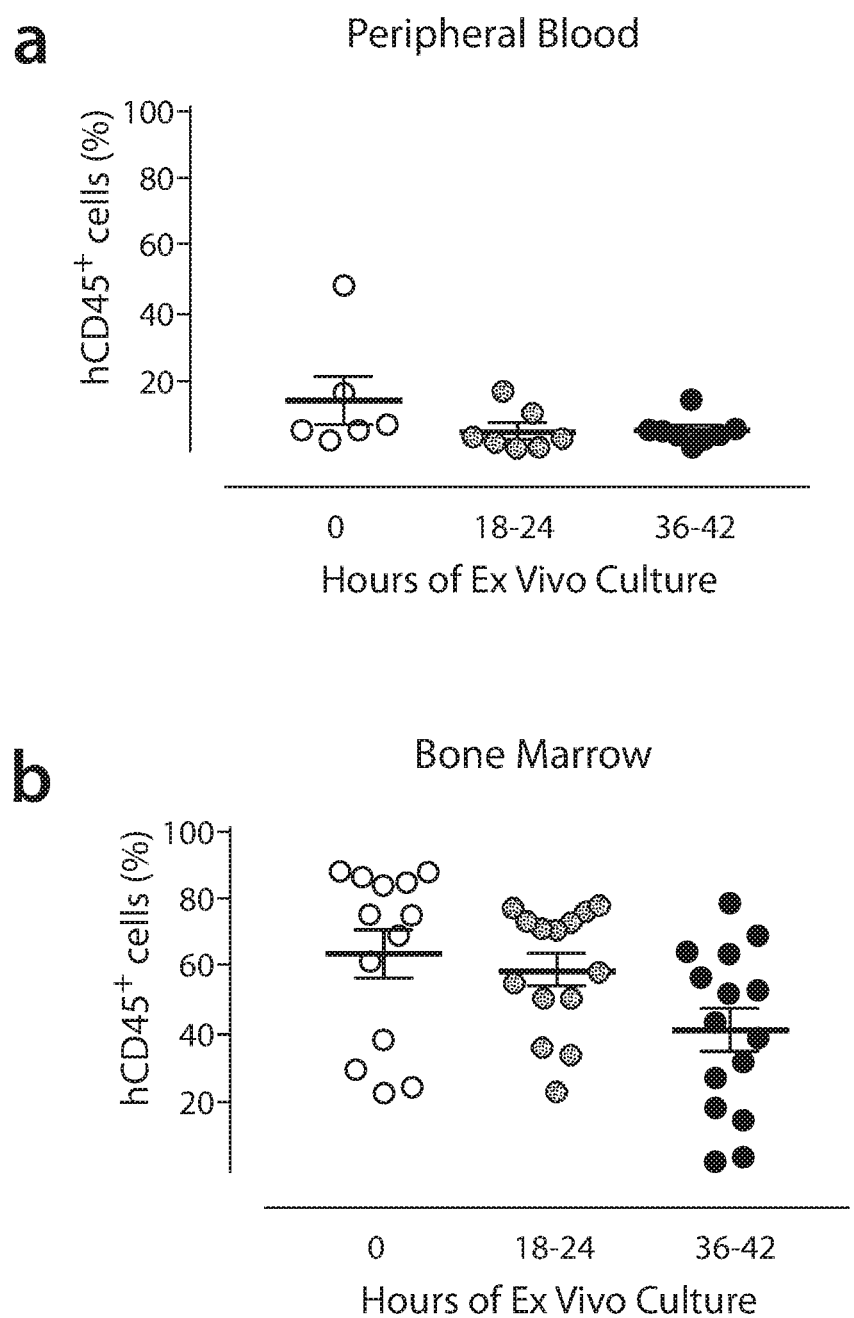
FIG. 1 shows a human xenograft model of adult hematopoietic stem cells. Freshly isolated human mobilized peripheral blood (MPB) derived CD34$^+$ cells (1 million cells/mouse) were transduced with a lentiviral vector (LV) within 18 hours and injected into irradiated NSG mice. Primary human engraftment was analyzed in mice at 6 weeks, in bone marrow (BM) (Panel A) and in peripheral blood (PB) concurrently (Panel B). Each symbol represents an individual mouse, lines show mean±S.E.M. (BM for 0 h n=13, 18-24 h n=14, 36-42 h n=15; PB: for 0 h n=6, 18-24 h n=7, 36-42 h n=8 mice). Panel C: At 6, 12 and 24 weeks post primary transplant (1 T), BM was analyzed for the different human cell populations by flow cytometry. Representative FACS plots showing human CD45$^+$ cells gated for GFP$^+$ (transduced) versus GFP$^-$ (untransduced) cells at 24 weeks post primary transplant (1 T). From the GFP$^-$ and GFP$^+$ human CD45$^+$ populations, human CD33$^+$ myeloid cells, human CD19$^+$ B-Lymphoid and CD3+T-Lymphoid cells and human CD34$^+$ HSPCs, that were negative for CD19 are shown. Panel D: The percentage multi-lineage engraftment analyzed at 6, 12, and 24 weeks after 1 T of uncultured MPB derived CD34$^+$ cells is shown. Data plotted as mean±S.E.M. For 6 weeks n=20, 12 weeks n=12, 24 weeks n=10 mice).
Figure 1:
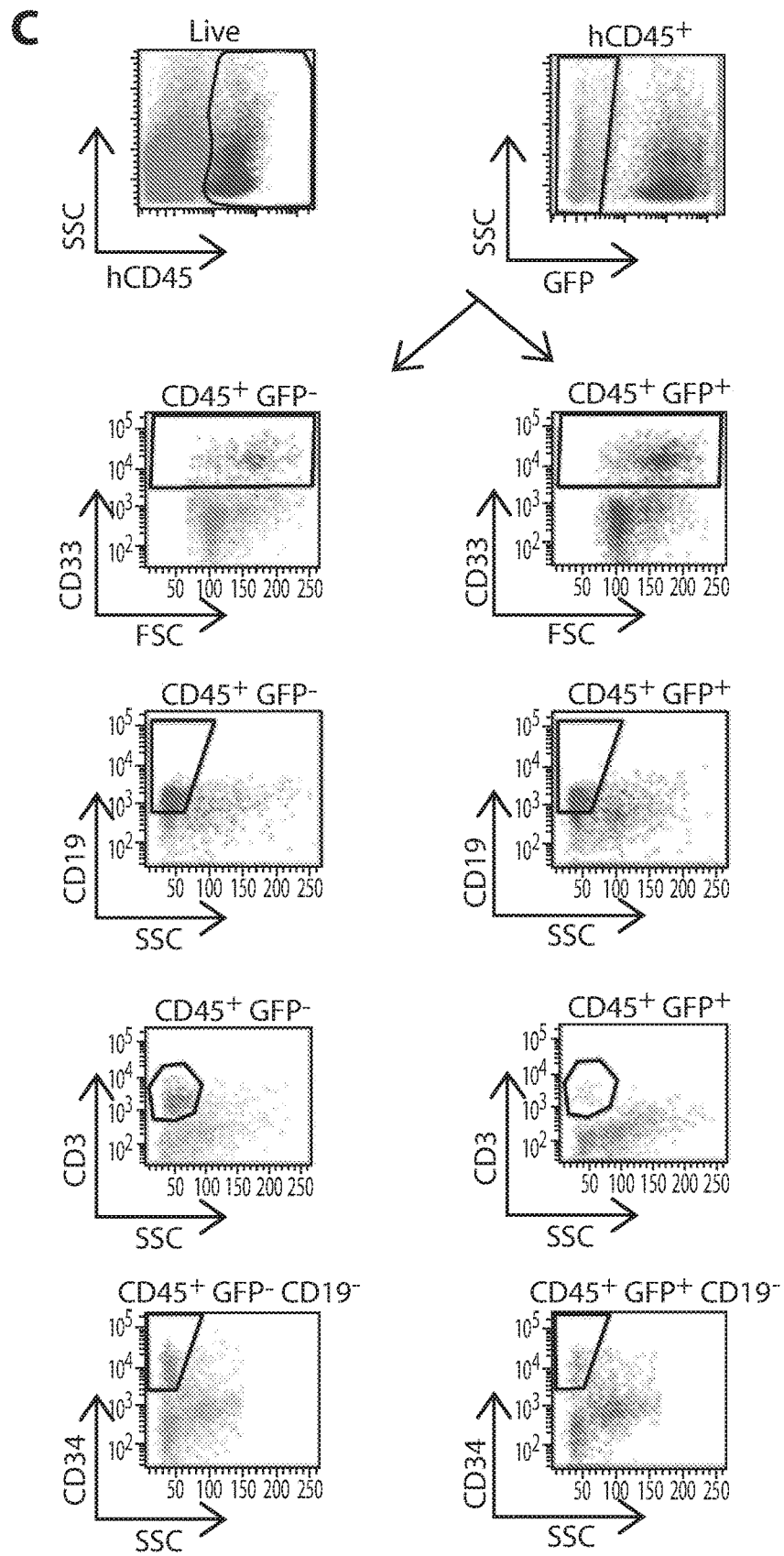
Figure 1:
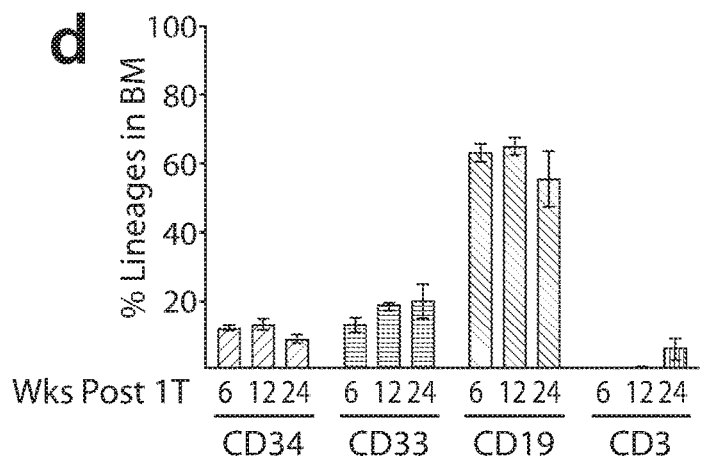

MAPK MFI in HSCs (Panel B). Data expressed as mean±SEM from 3 independent experiments. Human CD45$^+$ engraftment in NSG mice with (striped bars) or without p38 inhibitor (solid bars) after 24 weeks post 1 T (Panel C), and human engraftment in NSG mice with or without p38i after 6 weeks post 2 T (Panel D). Non-engrafted mice (<0.01% CD45$^+$ cells in the whole BM) over total mice transplanted is shown as percentage. Statistics: For Panel D, Fisher's exact test was performed. Human CD33$^+$ myeloid (Panels E and F), CD19$^+$ B-Lymphoid (Panels G and H) and CD34$^+$ HSPCs (Panels I and J) re-constitution with or without p38i (Panels E, G and I: GFP$^-$ untransduced; Panels F, H, and J: GFP$^+$ transduced) in 1 T mice 24 weeks post transplantation. Data expressed as mean±SEM from 5 independent experiments (for Panels C and E-J). For 0 h: n=15 mice, 18-24 h no treatment (Φ) n=19 mice, 18-24 h p38i n=21 mice, 36-42 h Φn=17 mice, 36-42 h p38i n=14 mice, 72-96 LV Φn=12 mice 72-96 LV p38i n=7 mice, 72-96 h RV Φn=17 mice, 72-96 h RV p38i n=17 mice for the total of 139 mice. Statistics: Mann Whitney U test (for Panels C and E-J), *P<0.05, P<0.01, *P<0.001.

Figure 10:
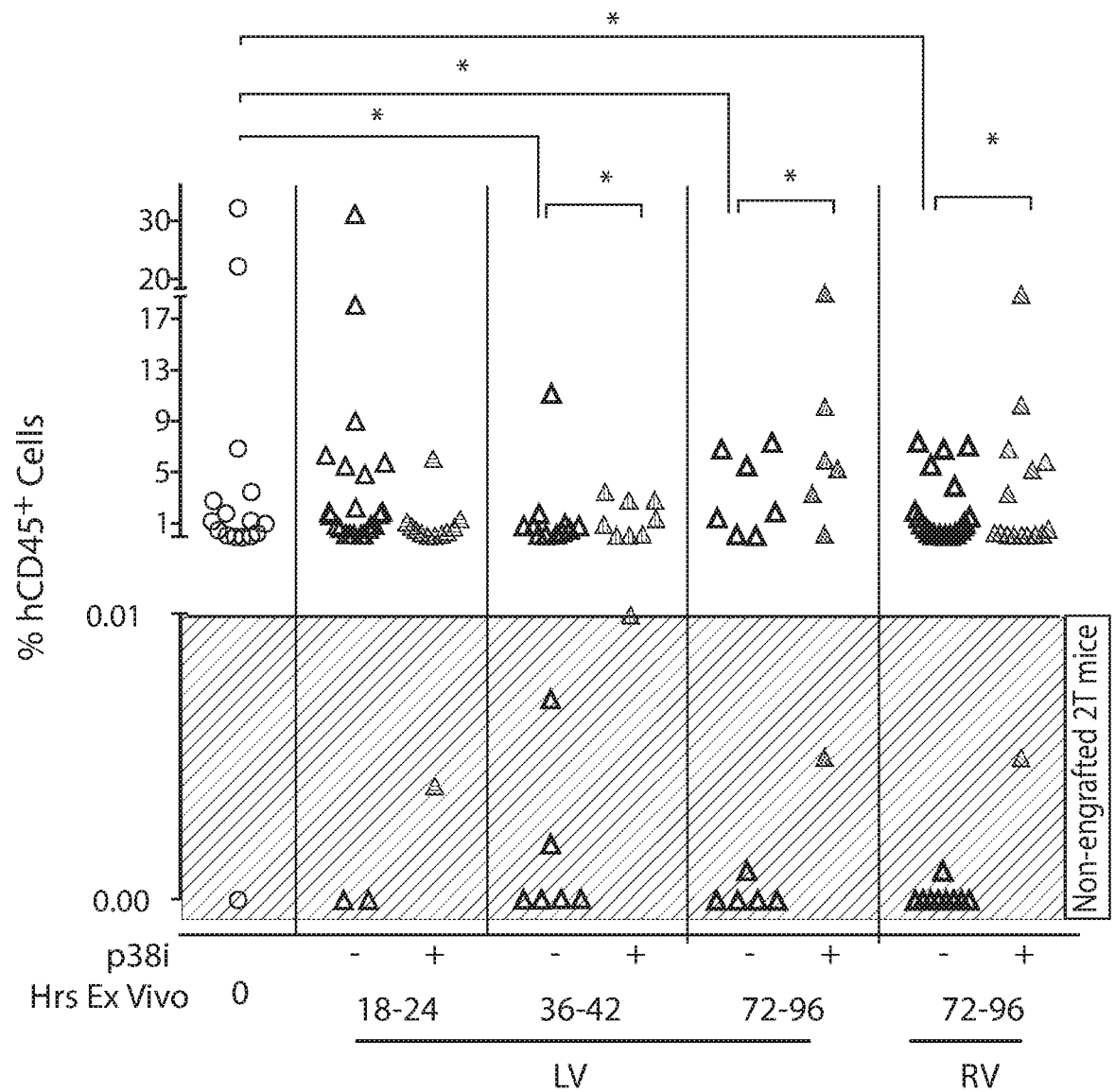

FIG. 10 shows that inhibition of p38 MAPK during ex vivo culture retains the human engraftment in the secondary transplanted NSG mice. Human engraftment in NSG mice with or without Birb 796 after 6 weeks of secondary transplant was examined. Engrafted mice (>0.01% CD45$^+$ cells in the whole bone marrow) are shown above the middle bar, engrafted/Total mice number is shown on the side. Empty triangles are control & filled triangles are treated with p38i. Each symbol represents an individual mouse. Data expressed as mean±SEM from 5 independent experiments (for 0 h n=16, for 18-24 h LV control n=25, for 18-24 h LV p38i n=11, for 36-42 h LV control n=17, for 36-42 h LV p38i n=9, for 72-96 h LV control n=12, for 72-96 h LV p38i n=7, for 72-96 h RV control n=29 and for 72-96 h RV p38i n=16) Statistics: Mann Whitney U test, *p<0.05, p<0.01, *p<0.001.

Figure 11:
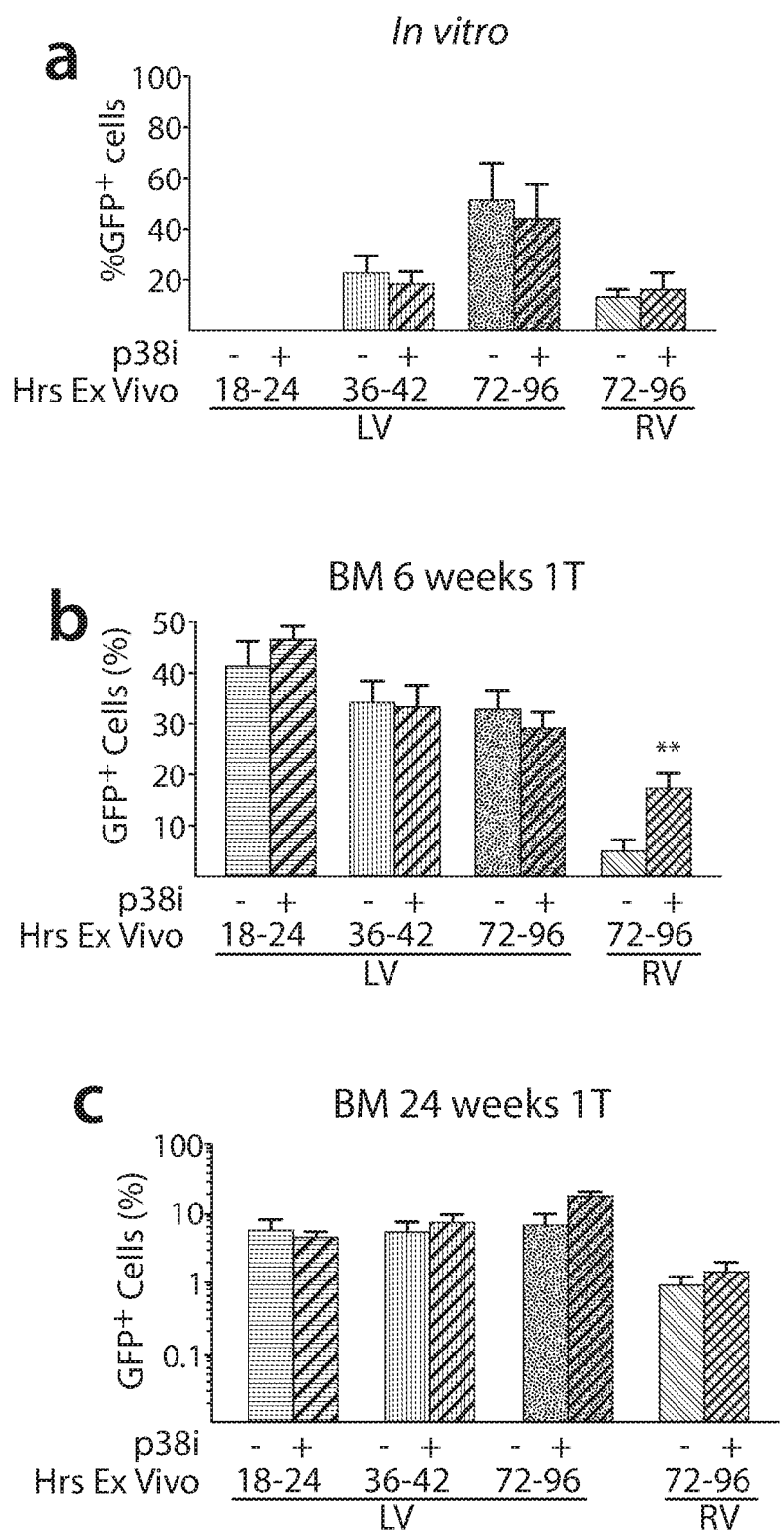

FIG. 11 shows GFP marking in bone marrow of NSG mice. Human CD34$^+$ cells were cultured as described in FIG. 9 and transplanted into NSG mice. Total human GFP$^+$ cells were analyzed in vitro before transplant (Panel A) and in vivo at 6 weeks (Panel B) and 24 weeks (Panel C) post primary transplant (1 T). In Panel A, 18-24 hours was not sufficient time for measuring GFP expression and thus not shown. Data expressed as mean±SEM from 5 independent experiments (n=12-21 mice per group). Statistics: Paired t test, **p<0.01.

Figure 12:
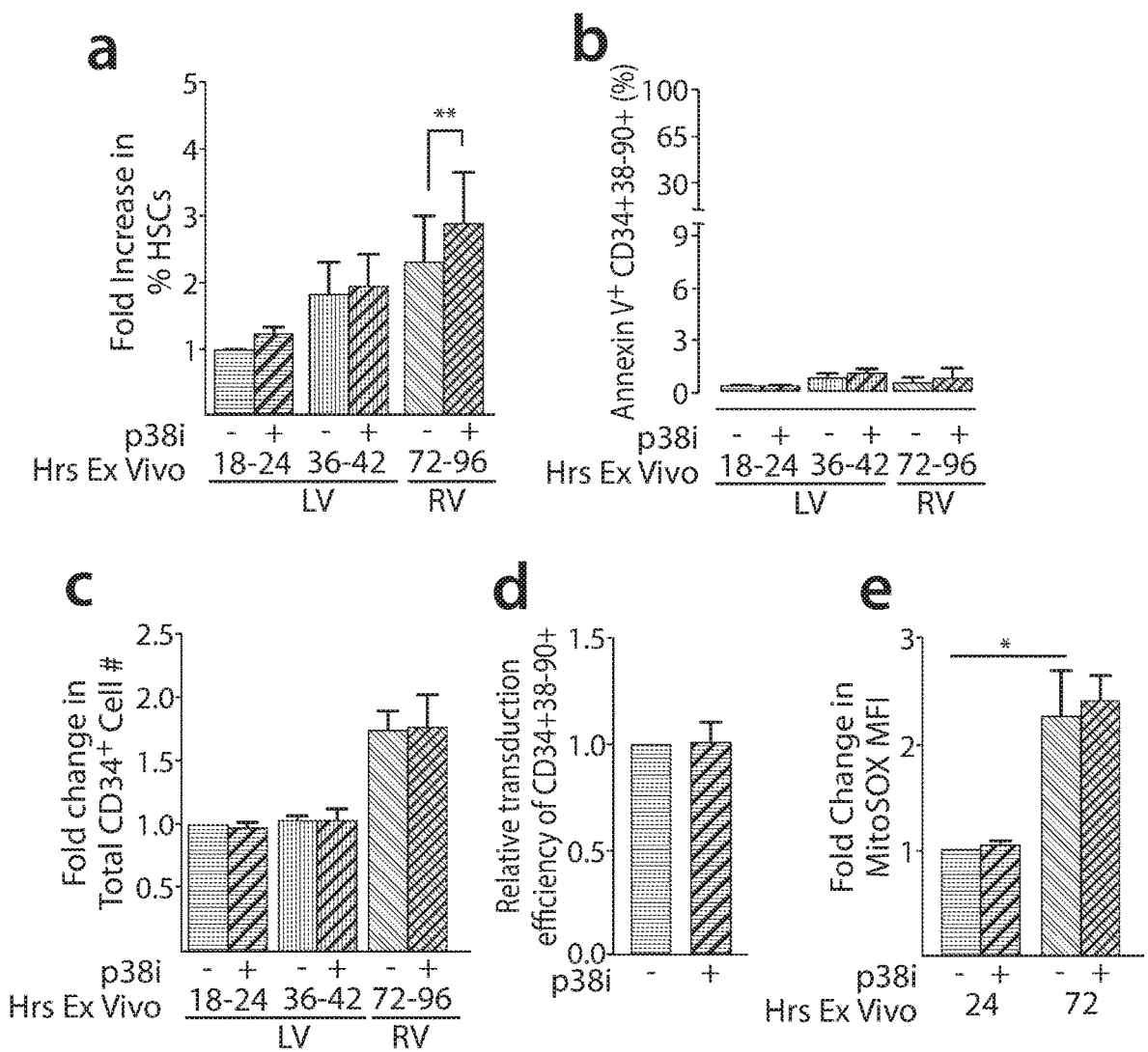

FIG. 12 shows that p38 inhibition does not change total CD34$^+$ cell number/viability, apoptosis, transduction efficiency, and ROS level but may retain the percentage of phenotypic HSCs. Human CD34$^+$ cells were cultured and transduced as described in FIG. 9, Panel A. Harvested cells were stained with trypan blue for viability, fold change in percent human CD34$^+$38$^-$90$^+$45RA$^-$49f$^+$ (HSCs) (Panel A) (n=6), percent annexin V$^+$ (apoptotic) CD34$^+$38$^-$90$^+$ cells (Panel B) (n=3), fold change in total viable CD34$^+$ cell number (Panel C), fold change in transduction efficiency (based on GFP marker percentage) over non-treated CD34$^+$38$^-$90$^+$ cells (Panel D) (n=5), and fold change in MITO-SOX™ (Red Mitochondrial Superoxide Indicator) in CD34$^+$38$^-$90$^+$ cells (Panel E) (n=3) are shown. Data represents mean±SEM. Statistics: Paired t test, *p<0.05.

Figure 13:
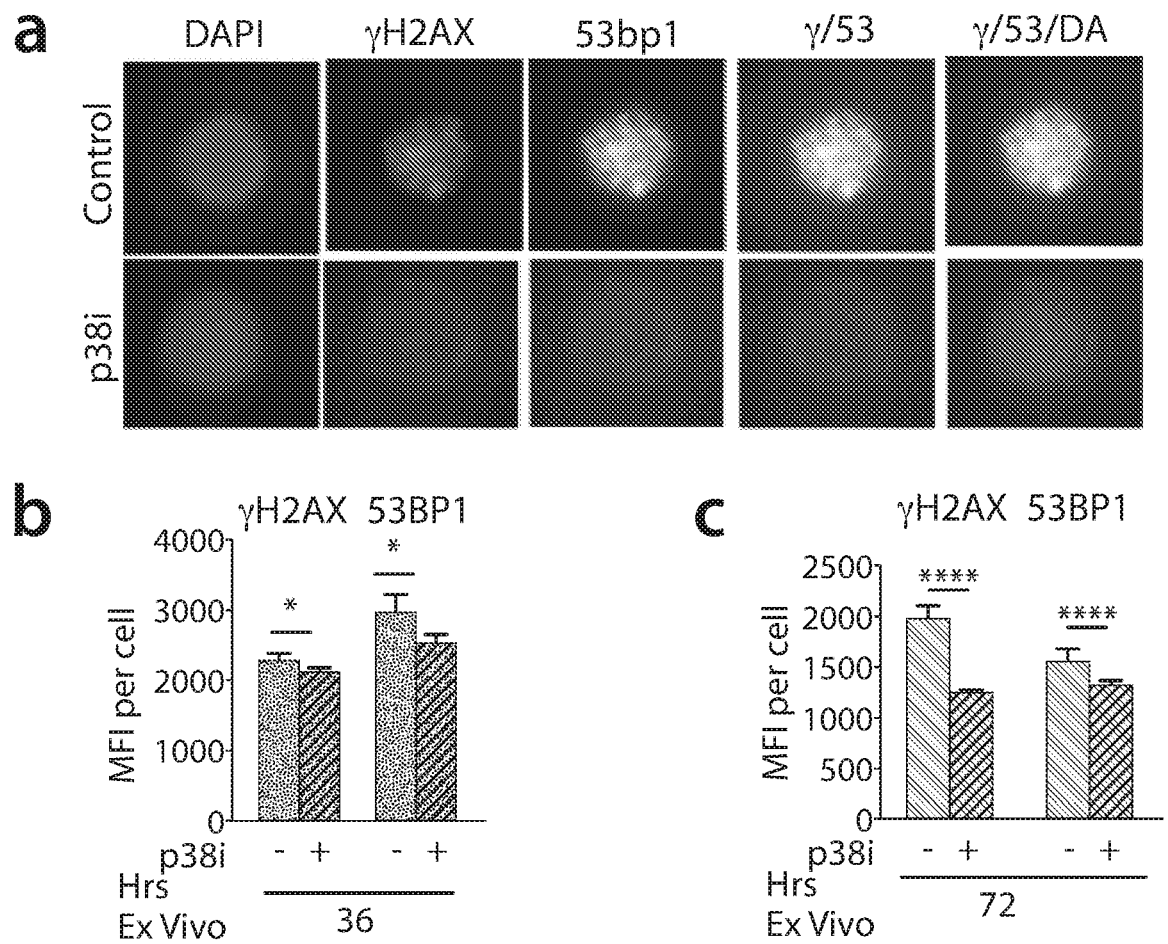
Figure 13:
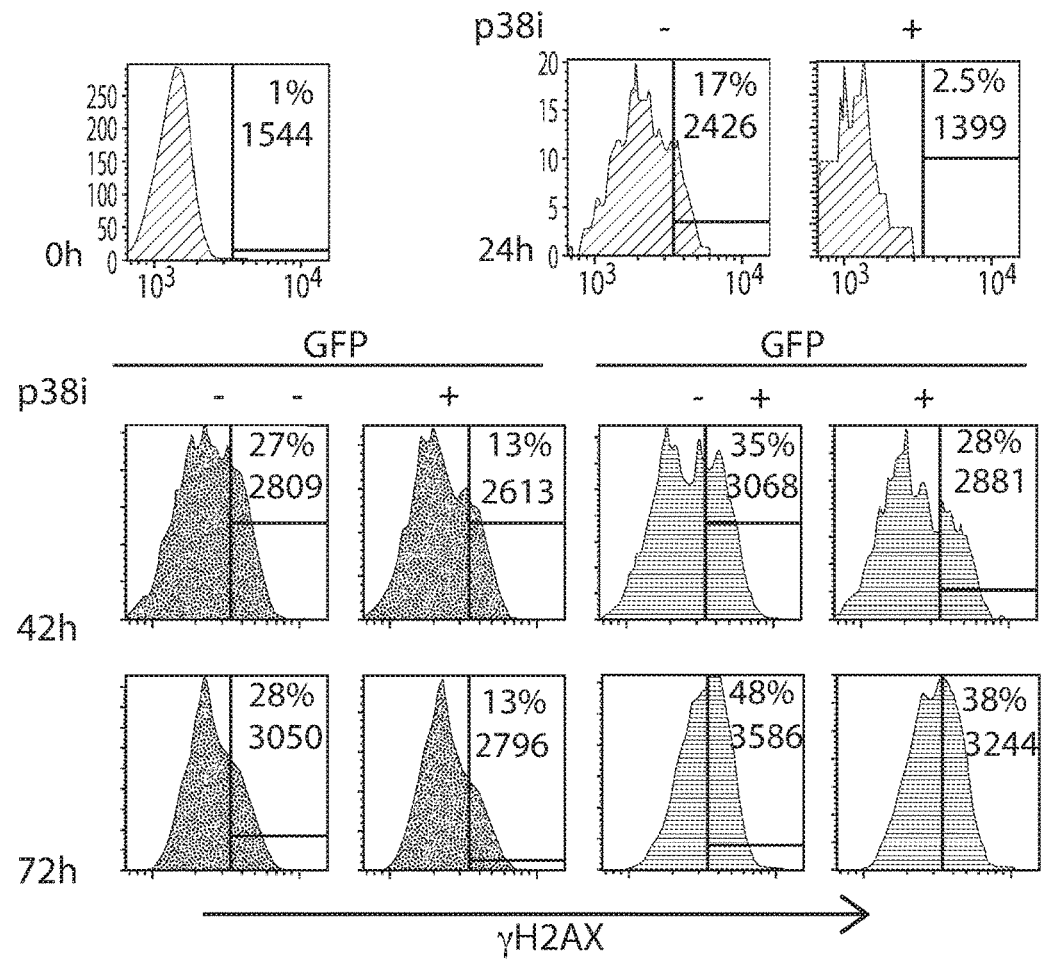
Figure 13:
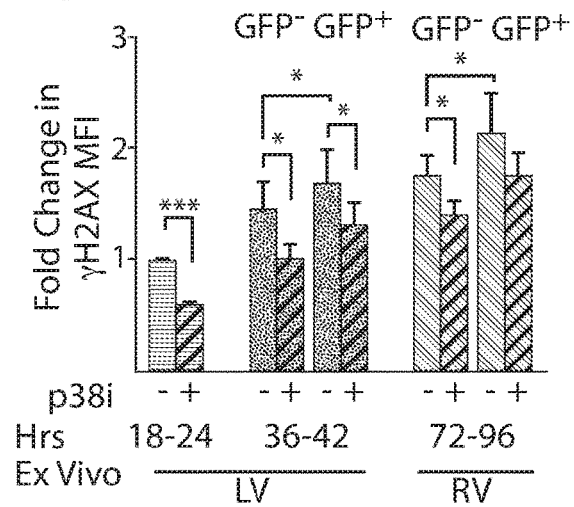
Figure 13:
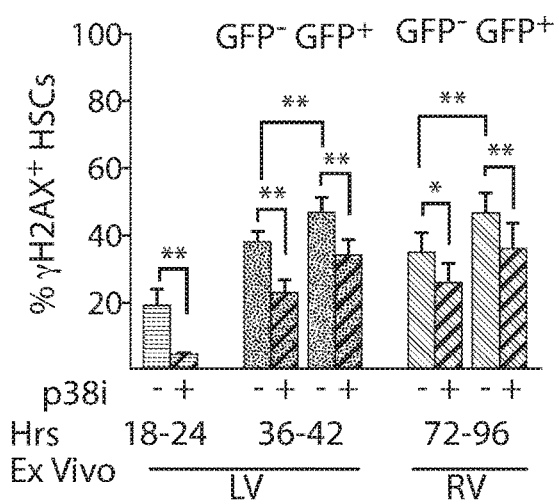

FIG. 13 shows that p38MAPK inhibition reduces DNA Damage Response (DDR) during ex vivo culture. Human CD34$^+$ cells were cultured and transduced with lentiviral vector (LV) or γ-retroviral vector (RV) expressing green fluorescent protein (GFP) for the indicated time points. Representative Immunofluorescence images of sorted human (CD34$^+$38$^-$90$^+$) HSCs treated with or without p38i for 72 hours stained with anti-γH2AX and 53BP1 (Panel A), and quantification of γ-H2AX and 53BP1 as MFI/cell in HSCs transduced with LV for 36 hours (Panel B), and with RV for 72 hours (Panel C). Representative histogram plot from flow cytometric analysis of HSCs stained for γ-H2AX with or without p38 inhibitor (p38i) (Panel D), and quantification of fold change in mean fluorescence intensity (MFI) of γ-H2AX (Panel E) and percent γH2AX$^+$ HSCs (Panel F), at the indicated time periods. Percentage shown in histograms are cells positive for γH2AX and the numbers below are mean fluorescent intensity (MFI) (n=5 independent experiments). Statistics: Mann Whitney U test and paired t test, *P<0.05, P<0.01, *P<0.001.

Figure 14:
Figure 14:
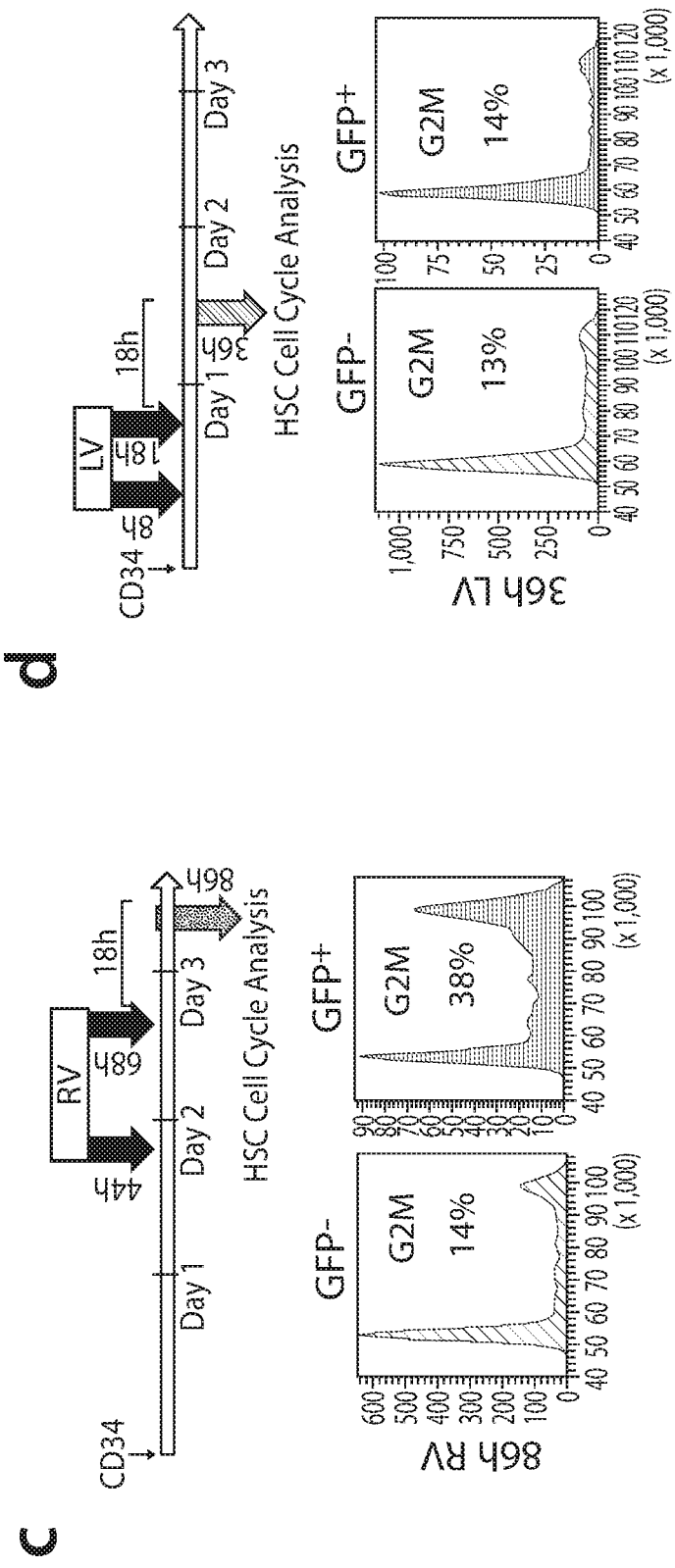
Figure 14:
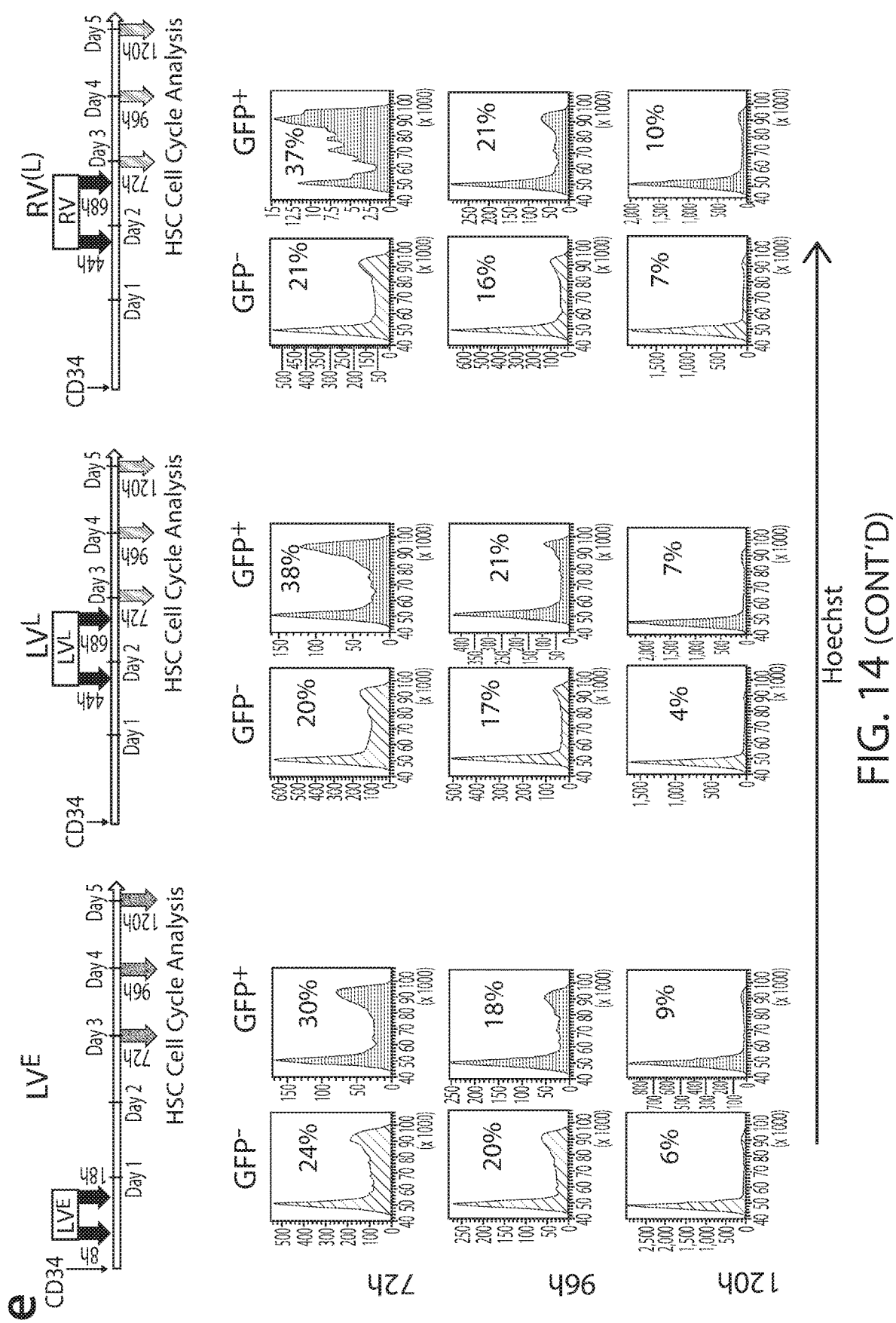
Figure 14:
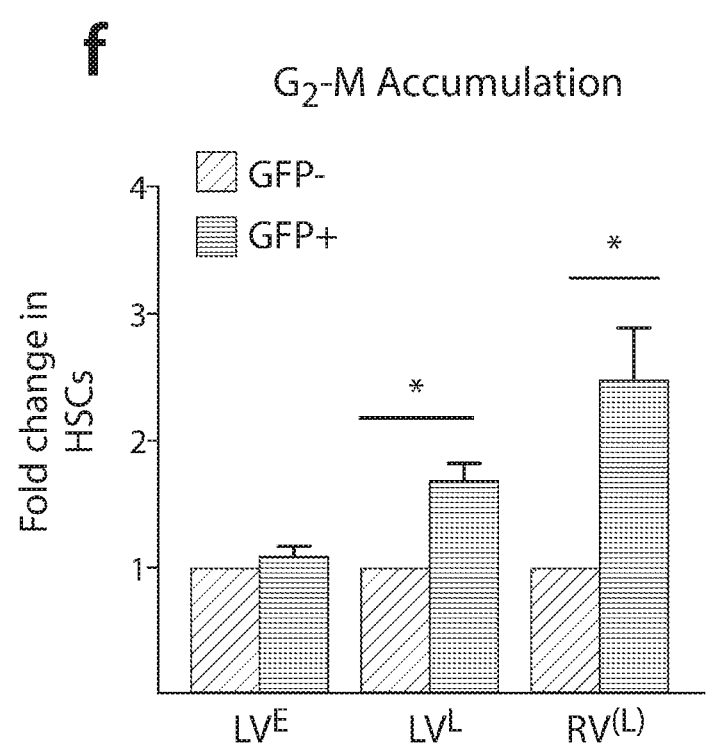

FIG. 14 shows that p38 MAPK inhibition retains HSCs in $G_0$ quiescent phase during early time period of ex vivo culture and transduction of human HSC enriched cells after longer ex vivo pre-stimulation time shows increased $G_2M$ phase accumulation. Human MPB derived CD34$^+$ cells were cultured and transduced as described in FIG. 13, Panel A. FACS plot representing (CD34$^+$38$^-$90$^+$) HSCs in $G_0$ (quiescent), $G_1$, and S-$G_2M$ phase of cell cycle with or without p38i at indicated time in culture (Panel A) and the quantification (Panel B) is shown. (Φ=no treatment) Percentage of (±SEM) HSCs in $G_0$, $G_1$ and S-$G_2M$ phase of cell cycle is depicted on the y-axis. (n=4 independent experiments for 24 h LV and n=7 for 42 h LV and n=5 for 72 h RV)). Panels C and D: Histogram plot representing the analysis of $G_2M$ phase accumulation in HSCs either with $LV^E$ (LV Early) (Panel C) or RV (Panel D) and analyzed 18 hours after the last transduction (n=1). Histogram plot representing time course analysis of $G_2$-M phase accumulation in HSCs transduced with LV either at early ($LV^E$) or late time period ($LV^L$) or with γ-retrovirus vector (RV) (Panel E). Quantification of fold change in GFP$^-$ (untransduced) versus GFP$^+$ (transduced) cells at $G_2M$ phase at 72 h of culture is shown (Panel F) (n=3 independent experiments). Statistics: paired Student's t test, *P<0.05, P<0.01, *P<0.001.

Figure 15:
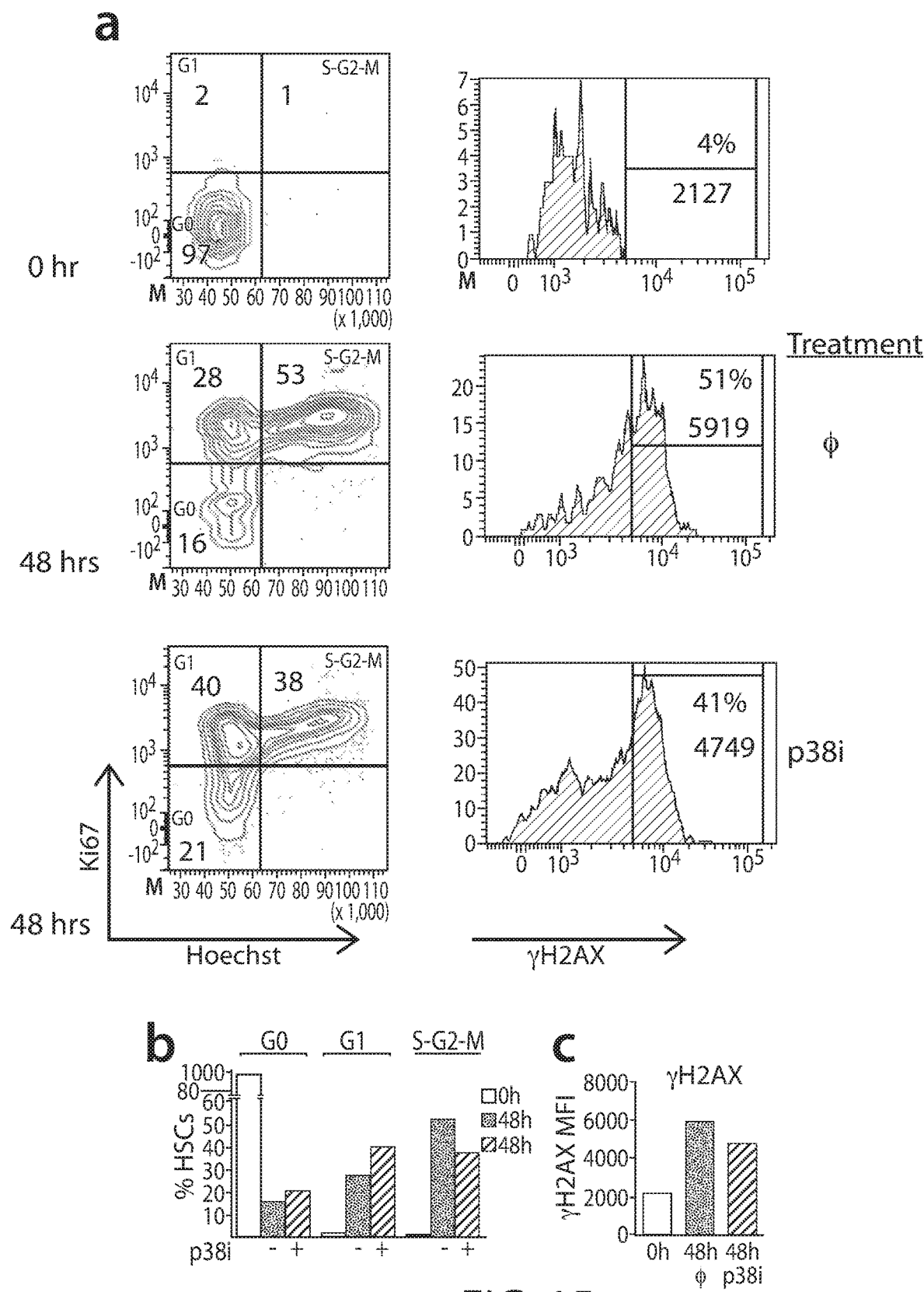

FIG. 15 shows that p38MAPK inhibition also reduces DNA Damage Response (DDR) in human CD34$^+$38$^-$90$^+$ cells derived from bone marrow (BM). Human BM derived CD34$^+$ cells were cultured and transduced with lentivirus (LV) for 48 hours. Panel A: Representative FACS plot representing bone marrow derived (CD34$^+$38$^-$90$^+$) HSCs in $G_0$ (Quiescent), $G_1$, and S-$G_2$-M phase of cell cycle with or without p38i (left) and the corresponding representative histogram plot of γH2AX at indicated time and treatment (right). Percentages shown in histogram are cells positive for γH2AX and the numbers below is mean fluorescent intensity (MFI). Quantitative plots of HSCs in various cell cycle phases (Panel B) and its corresponding γH2AX MFI (Panel C) are shown. n=1 experiment.

Figure 16:
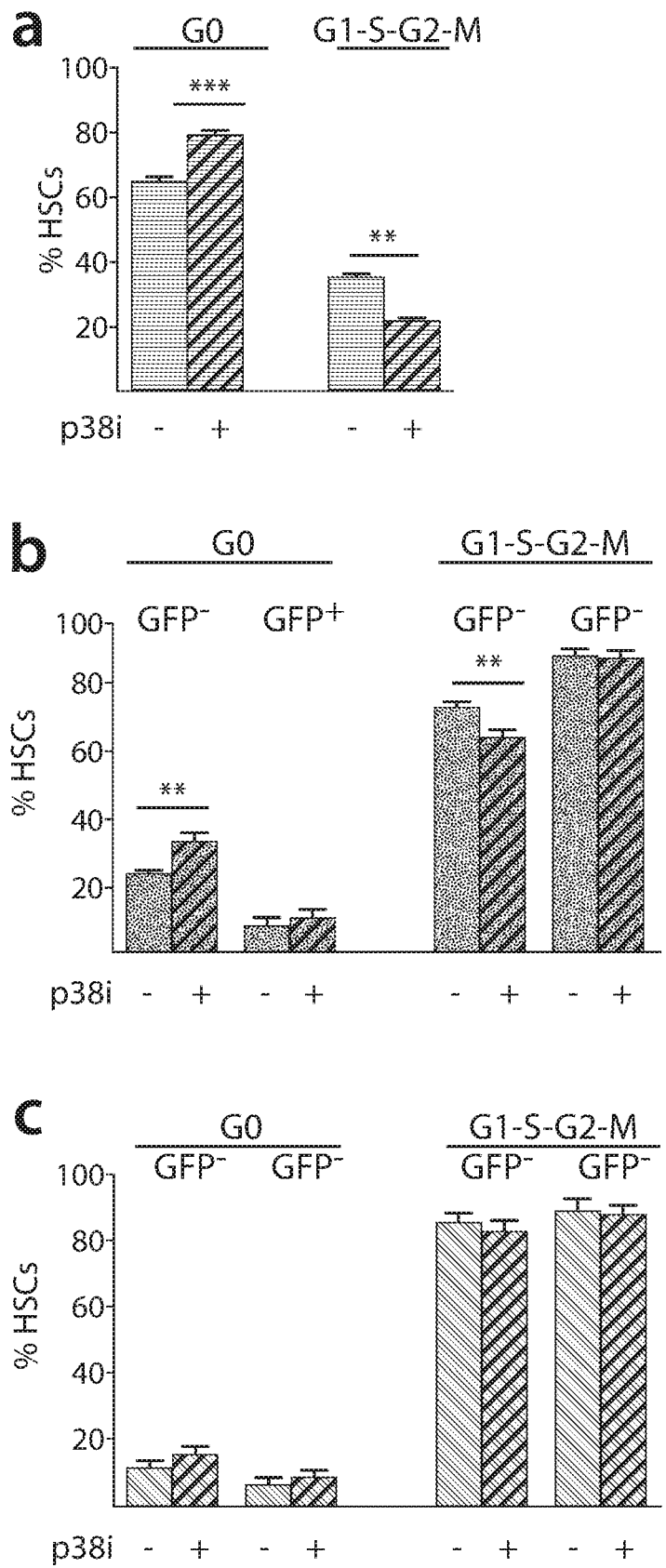

FIG. 16 shows that p38MAPK inhibition retains HSCs in $G_0$ quiescent phase during early time period of ex vivo culture and gene transfer. Human MPB derived CD34$^+$ cells were cultured and transduced as described in FIG. 13. Quantitative plot representing (CD34$^+$38$^-$90$^+$) HSCs in $G_0$ and $G_1$-S-$G_2$-M phase of cell cycle with or without p38i at 24 hours (LV) (Panel A), 42 hours (LV) (Panel B), and 72 hours (RV) (Panel C) of ex vivo culture. (n=4 independent experiments for 24 h LV, n=7 for 42 h LV and n=5 for 72 h RV). Statistics: paired t test, *p<0.05, p<0.01, *p<0.001.

Figure 17:
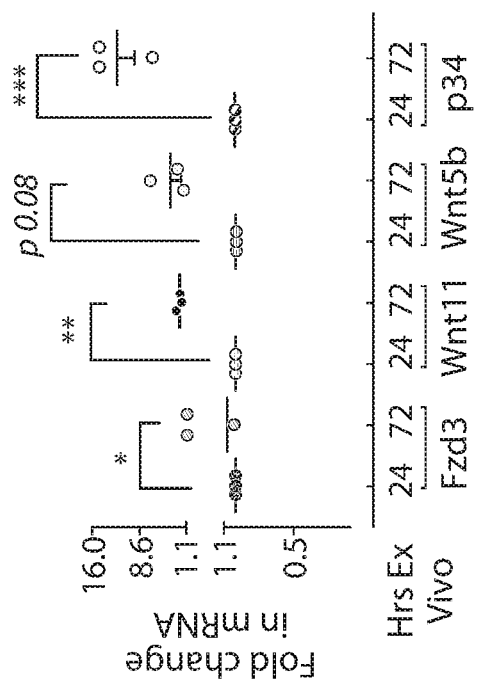
Figure 17:
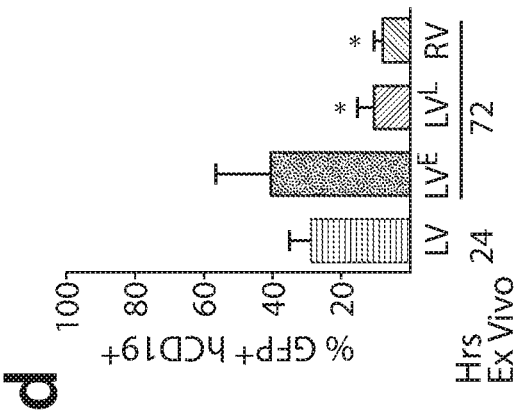
Figure 17:
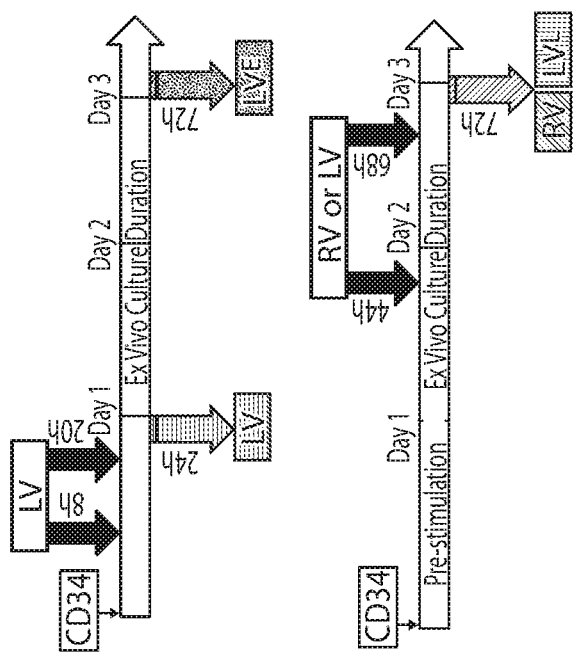
Figure 17:
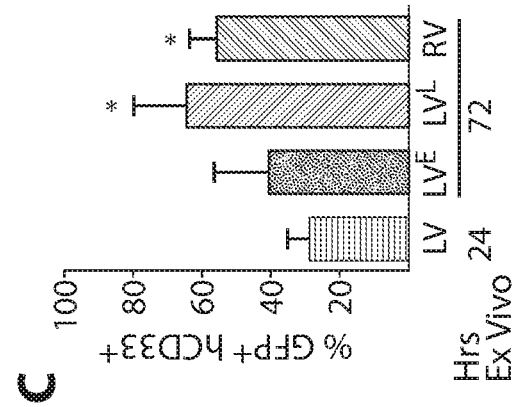
Figure 17:
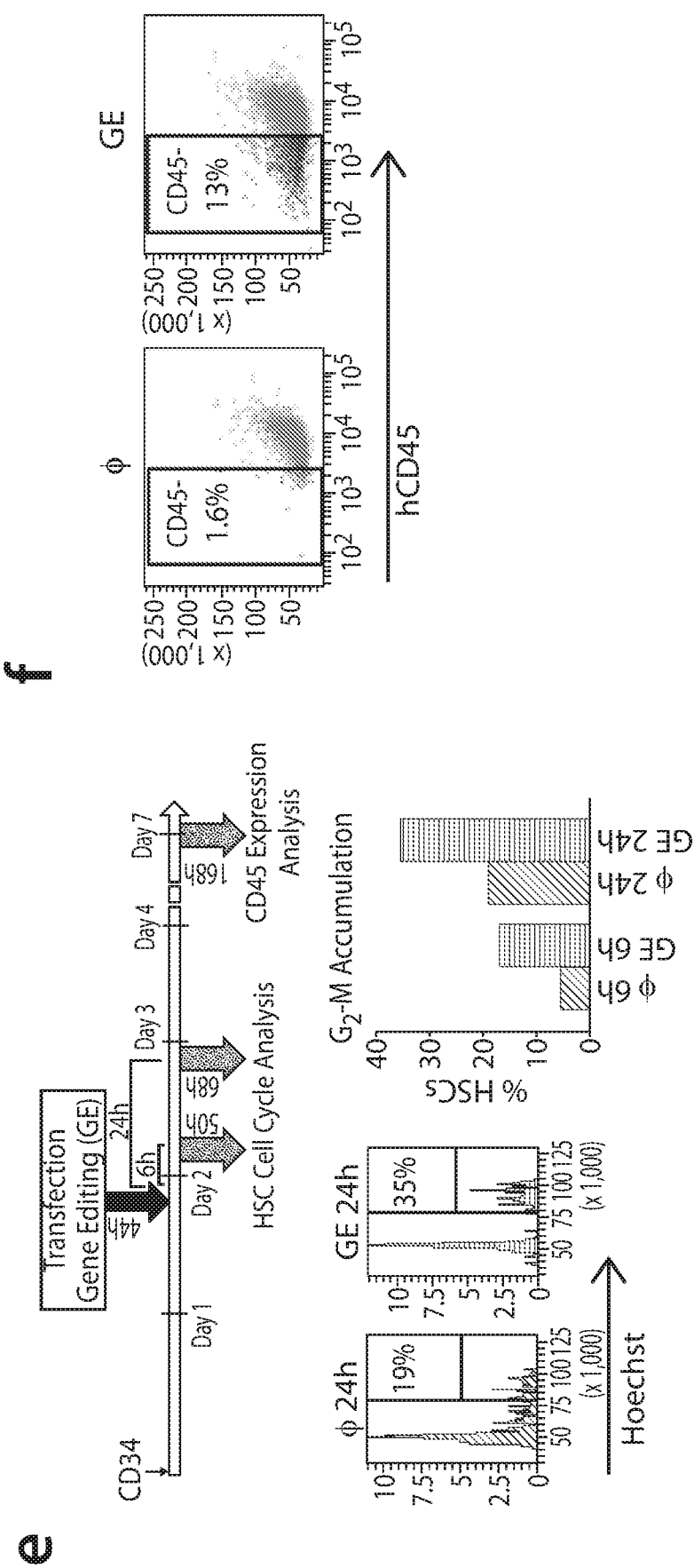

FIG. 17 shows that transduction of non-cycling HSCs (6 and 18 h with LV; $LV^E$) retains HSC lineage fate, but transduction of cycling HSCs (at 44 h and 68 h with RV or LV [LV$^L$]) results in a myeloid biased HSC fate. Panel A: Ex vivo culture and transduction schema. Panel B: mRNA expression of genes associated with aging in 24 h versus 72 h cultured (CD34$^+$38$^-$90$^+$) HSCs analyzed by qPCR. GAPDH was used as a reference gene. n=3 MPB donors. Data mean±SEM. Unpaired t test. *p<0.05, p<0.01, *p<0.001. CD33$^+$ Myeloid (Panel C) and CD19$^+$ B lymphoid (Panel D) lineage proportions within transduced (GFP$^+$) CD45$^+$ cells in BM of NSG mice 24 weeks after 1 T. Data expressed as mean±SEM (n=5 mice for 24 LV and 72 LV$^E$, n=4 mice for 72 LV$^L$ or 72 RV). Statistics: Mann Whitney U test, *p<0.05. Panel E: Transfection Schema (top) G$_2$M accumulation in φ (no transfection control) versus gene edited (GE) (transfected) (CD34$^+$38$^-$90$^+$) HSCs (below: left). GE was performed by transfection of RNPs containing Cas9 and gRNA after 44 hours of pre-stimulation and cell cycle analyzed either at 6 hours or 24 hours post transfection. Quantitative plot showing time course of G$_2$-M accumulation 6 hours versus 24 hours after transfection (below: right). Panel F: % hCD45 expression in total CD34$^+$ cells with or without GE on day 7.

Figure 18:
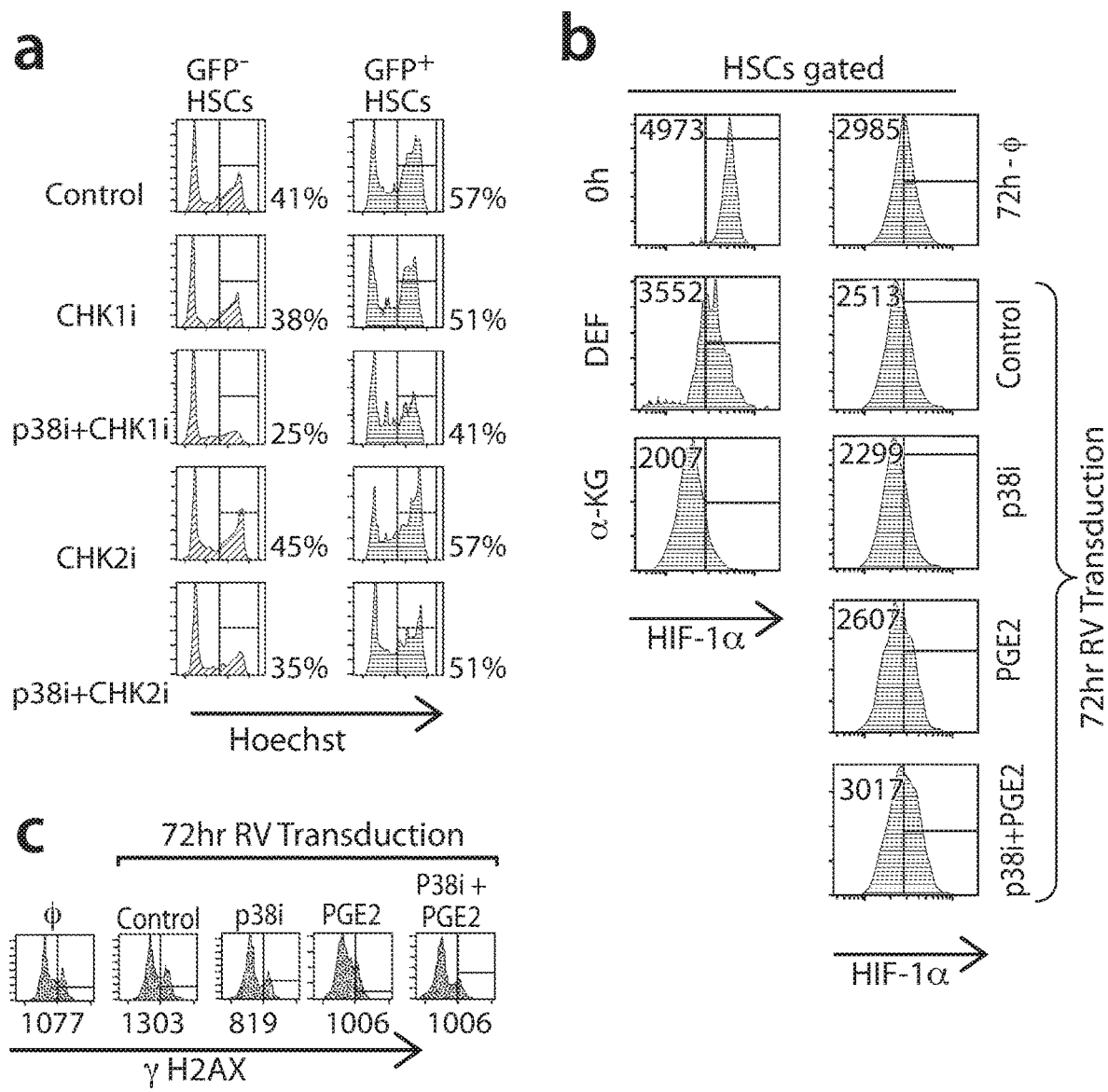

FIG. 18 shows that increased HSC enriched cells at G$_2$-M phase is specific to CHK1, not CHK2 and transduction during ex vivo culture decreased HIF1α and increased γH2AX which are reversed by the combination of p38 inhibitor (p38i) and prostaglandin E2 (PGE2). Panel A: Representative histogram plot of G$_2$-M phase accumulation (% shown) in (CD34$^+$38$^-$90$^+$) HSCs transduced with RV for 72 hours with indicated compounds. Panel B: Representative histogram plot of HSCs stained for HIF-1α; DEF (Diethyl Fumarate) and u-KG (α-Keto Glutarate) used as a positive and negative control for HIF-1α staining. n=1. Panel C: Representative histogram plot of γH2AX in (CD34$^+$38$^-$90$^+$) HSCs after 72 hours of culture and RV transduction with indicated compounds. Numbers represents mean fluorescent intensity (MFI). φ=No transduction, Control=no treatment.

Figure 19:
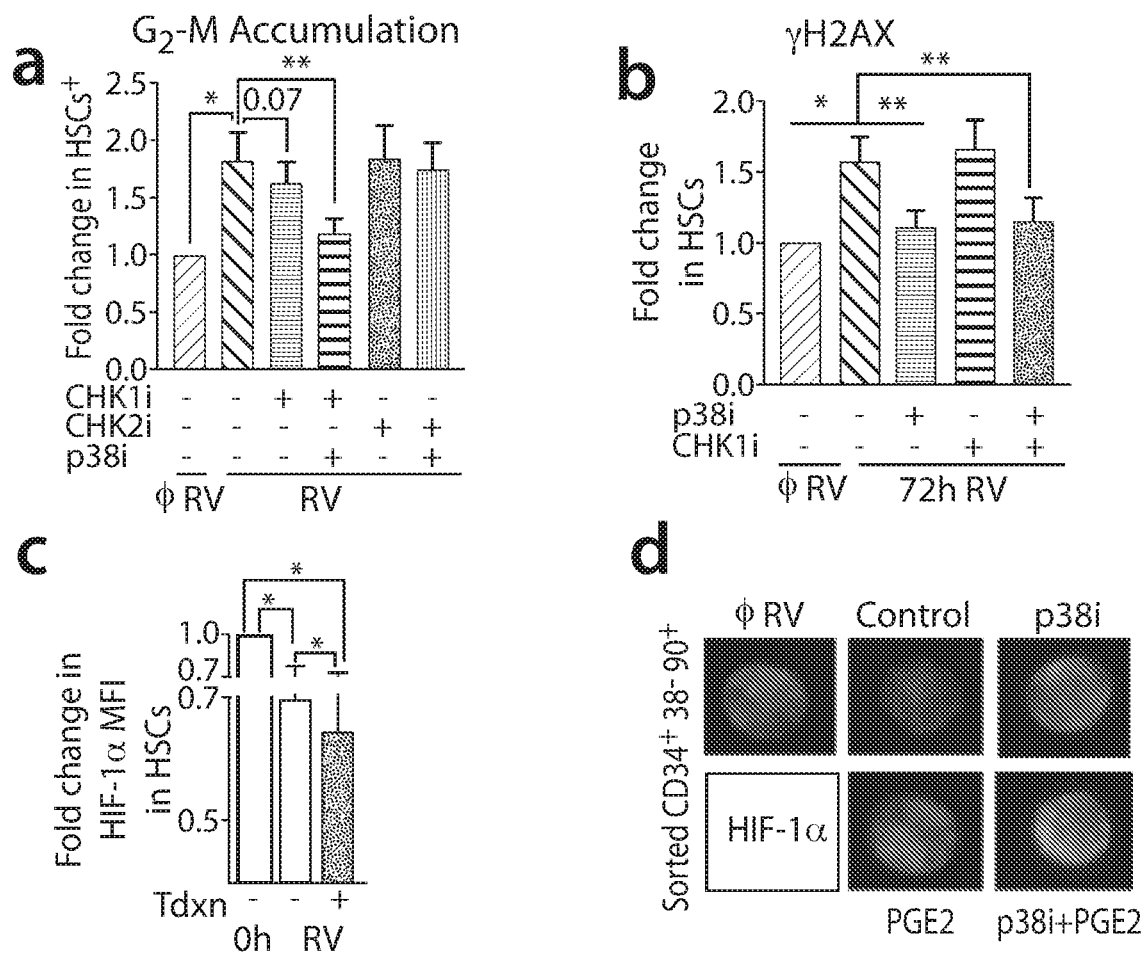
Figure 19:
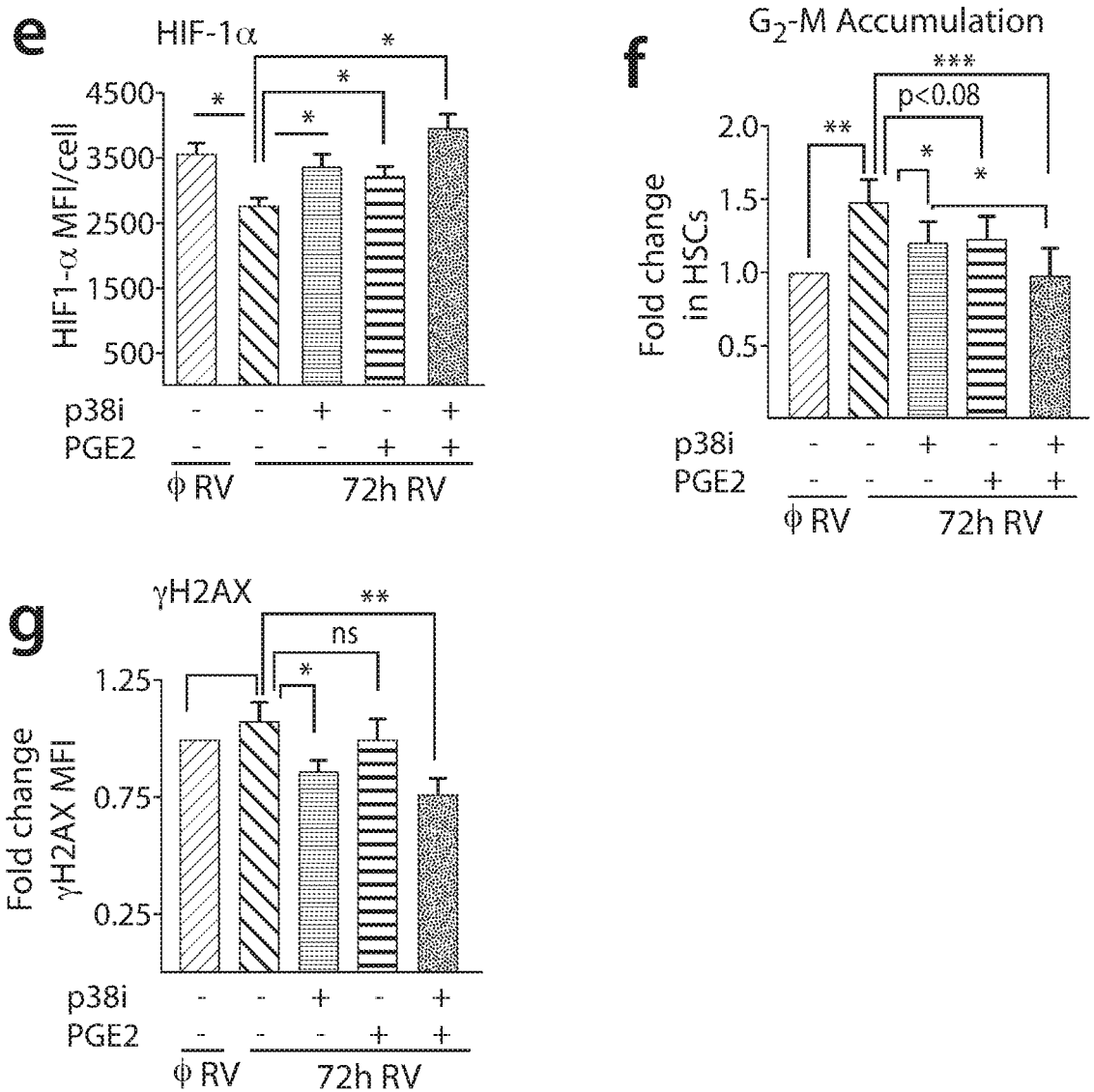

FIG. 19 shows that increased G$_2$M phase accumulation and decreased HIF-1α in late transduced HSCs is reversed by p38 inhibitor (p38i) in combination with either Chk1 kinase inhibitor (Chk1i) or prostaglandin E2 (PGE2). Quantification of fold change in GFP$^-$ (untransduced) versus GFP$^+$ (transduced) HSCs (CD34$^+$38$^-$90$^+$) in G$_2$M phase by flow cytometry after 72 hours of RV transduction (Panel A) (n=6, statistics: paired student's t test, *P<0.05. **P<0.01), and quantification of fold change in γ-H2AX mean fluorescent intensity (MFI) (Panel B) (n=9 independent experiments; statistics: Paired wilcoxon test, *P<0.05. **P<0.01). Panel C: Quantitative fold change in HIF-1α MFI in HSCs (n=3 independent experiments using 3 different MPB donors; paired student's t test). Representative immunofluorescence image of HSCs stained for HIF-1α (Panel D) and quantitative MFI of HIF-1α per cell are shown (Panel E) (statistics: paired wilcoxon test, * P<0.05). Quantitative fold Change in HSC enriched cells at G$_2$-M phase (Panel F) (n=8) and fold change in γ-H2AX MFI of HSCs (Panel G) with indicated treatments are shown (n=9 independent experiments; statistics: paired student t test, * P<0.05. P<0.01, *P<0.001).

Figure 20:
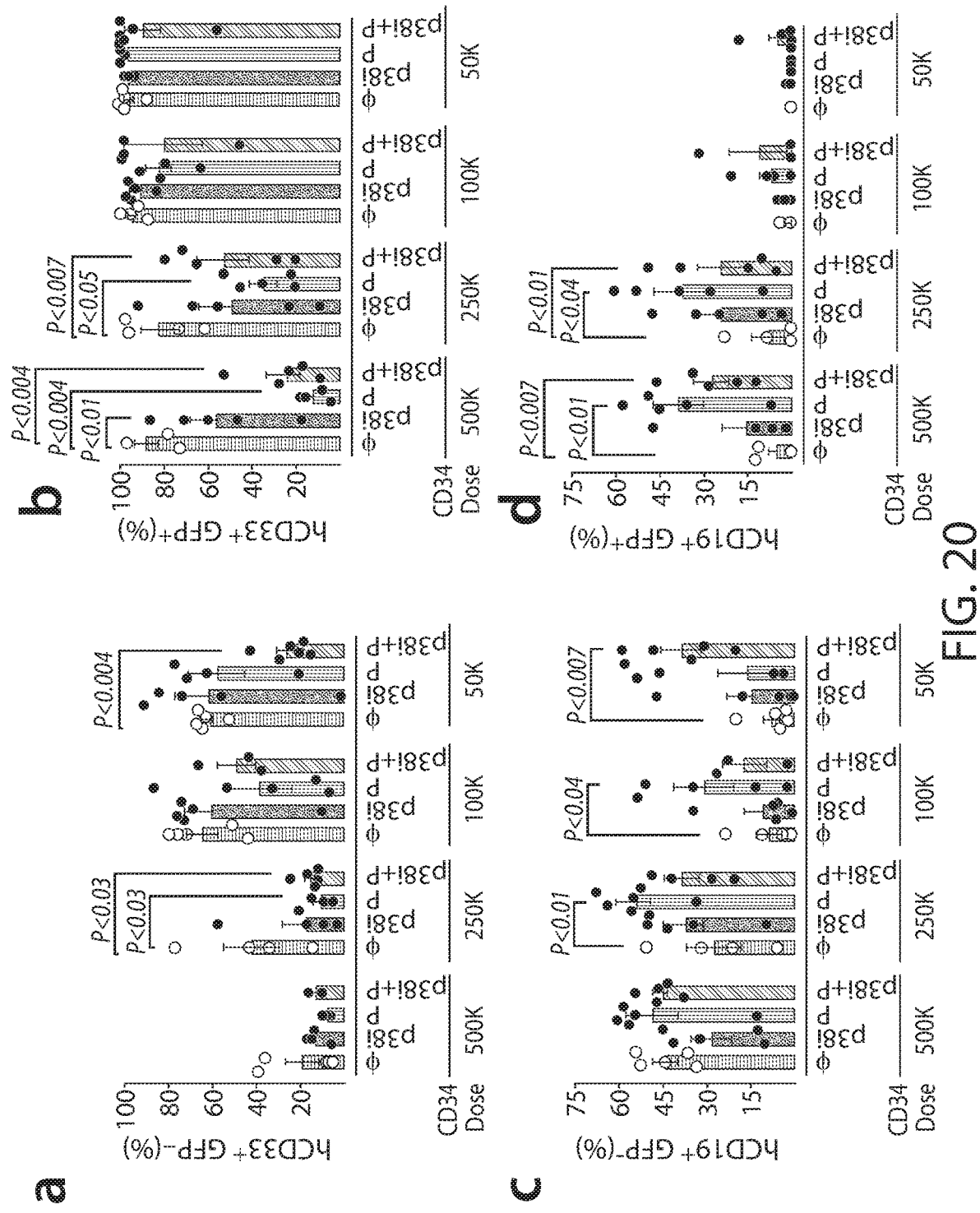
Figure 20:
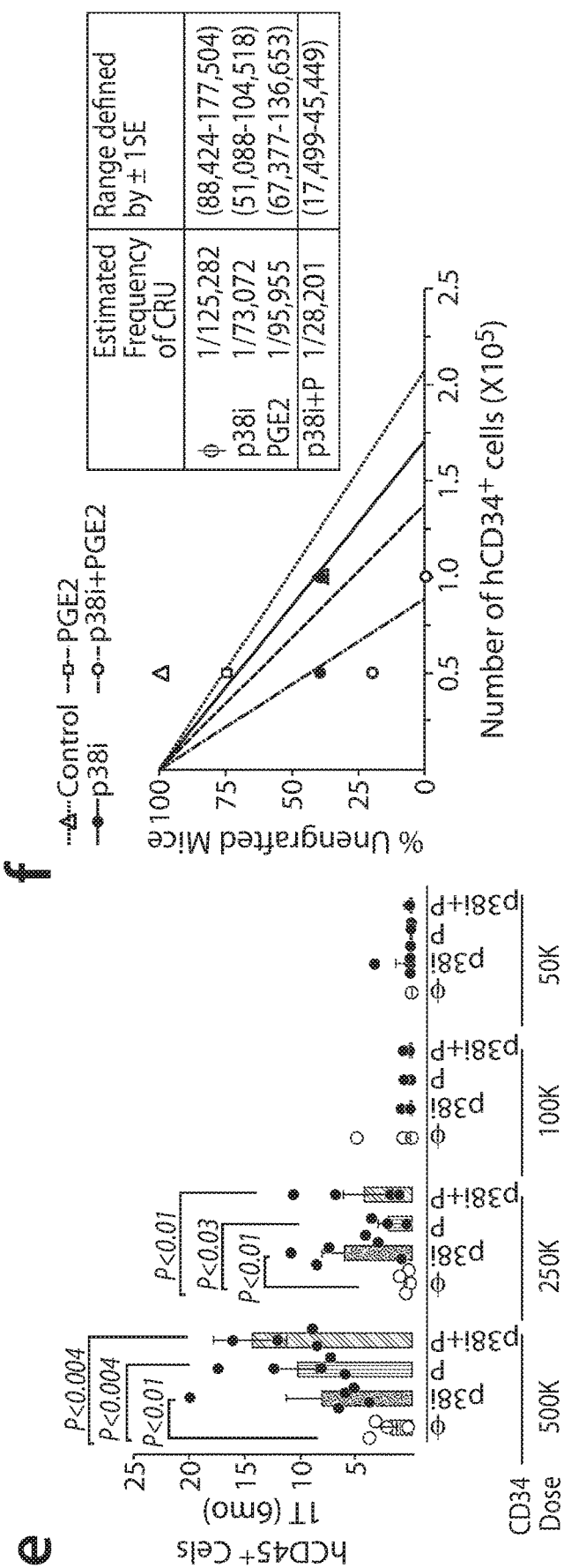
Figure 20:
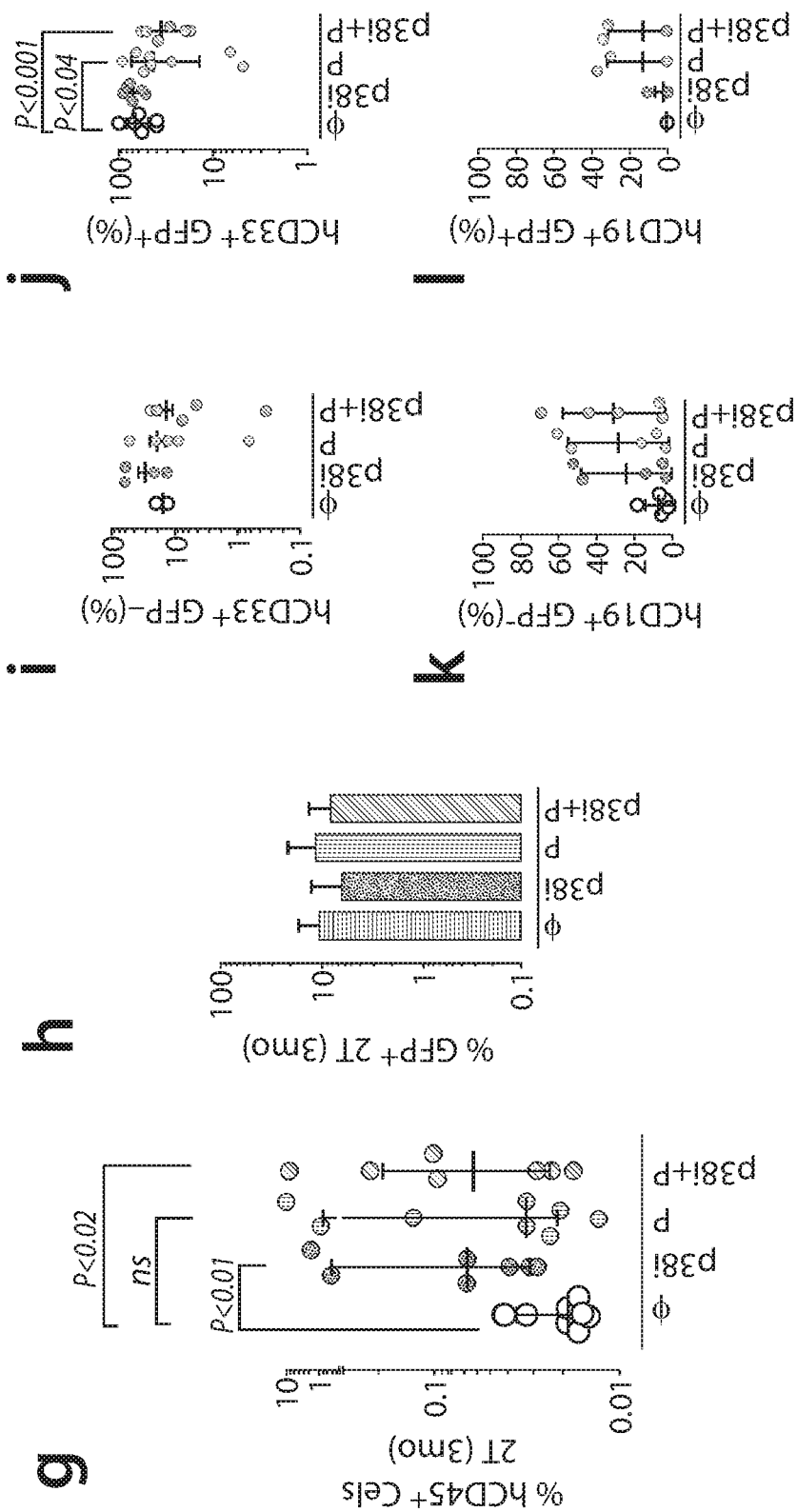

FIG. 20 shows that combined treatment of p38i and PGE2 increased human engraftment and a complete reversal of myeloid skewing phenotype in CD34$^+$ cells transplanted mice at limiting doses. Limiting Dilution transplant was performed as described in methods. Mice were injected with the indicated number of starting CD34$^+$ cells after 42 hours of lentiviral (LV) transduction and culture with no treatment (#: open green circles), p38 inhibitor (p38i: filled blue circles) or PGE2 (P: filled purple circles) or p38i+PGE2 (p38i+P: filled red circles). The percentage of human CD33$^+$ myeloid cells (untransduced; GFP$^-$: Panel A and transduced GFP$^+$: Panel B) and CD19$^+$ B-lymphoid cells (untransduced; GFP$^-$: Panel C and transduced GFP$^+$: Panel D) in the bone marrow (BM) at 6 months post 1 T are shown (n=5 mice/treatment for each of the CD34 input doses, except for P: 500K dose n=4, p38i+P: 50K dose n=3, and #: 250K dose n=4, for a total of 76 NSG mice). % Human CD45$^+$ cells in the bone marrow at 6 months (6 mo) post primary transplant (1 T) (y axis) and equivalent number of starting CD34$^+$ cells (X-axis) are shown (Panel E). Plotted are the percentages of negative or unengrafted mice containing less than 0.1% human CD45$^+$ cells at 6 months post-primary transplant (Panel F). Frequency of functional HSCs (Competitive repopulation units: CRU) is shown on the side in the table. As described in methods, secondary transplants were performed after 24 weeks post primary limiting dilution transplant from the highest input doses used in 1 T. % Human CD45$^+$ cells (Panel G), GFP$^+$ hCD45$^+$ cells (Panel H), and % Human CD33$^+$ myeloid cells (untransduced; GFP$^-$: Panel I and transduced GFP$^+$: Panel J), CD19$^+$ B-lymphoid cells (untransduced; GFP$^-$: Panel K and transduced GFP$^+$: Panel L) in the BM at 12 weeks post-secondary transplant (2 T) are shown. For φn=9, for p38i n=7, for P n=8, and for p38i+P: n=8 for a total of 32 NSG mice. Data expressed as mean±SEM. Statistics: Mann Whitney U test, exact P values shown.

DETAILED DESCRIPTION OF THE INVENTION

Hematopoietic stem cells (HSCs) are desirable targets for gene therapy for various inherited hematological diseases including, e.g., hemoglobinopathies. They have the ability to differentiate into hematopoietic progenitor cells (HPCs) to regenerate the hematopoietic system. However, gene transfer into HSCs or gene editing in HSCs typically involves ex vivo manipulation and culture, which results in a large amount of HSC loss, making these cells less competent at engraftment in vivo. Currently, the limited number of HSCs that repopulate after autologous transplant is a major limitation to effective gene transfer. Thus, large transduced HSCs at myeloablative conditioning to destroy resident HSCs are currently required to provide an engraftment advantage. However, the source of HSCs is limited and myeloablative conditioning could induce adverse effects or complications in patients who are sensitive to such procedure. Accordingly, there is a need to develop methods and compositions for preparing hematopoietic stem cells (HSCs) for increased engraftment in subjects who are in need of a HSC transplantation.

While a p38 MAPK inhibitor alone effectively maintained the stemness of hematopoietic stem cells (HSCs) before their first cell division by effectively reducing DNA damage response (DDR) associated with ex vivo manipulation stress (e.g., extended ex vivo culture and/or gene manipulation), such effects of the p38 MAPK inhibitor in HSCs became less effective after the HSCs progressed through the cell cycle. The present disclosure is based, at least in part, on the unexpected discovery that a combination of a p38 MAPK inhibitor and a HIF-1α stabilizer displayed a synergistic effect on enhancing the engraftment capacity of the stem cells (e.g., HSCs such as cycling or dividing HSCs), but the absence of either agent failed to do so. In particular, it was discovered that when a DNA double strand break (e.g., due to genetic manipulation) occurred in cycling or dividing HSCs, there was an accumulation of HSCS in the late S and $G_2M$ phases, the phenomenon of which was not observed in non-cycling HSCs. Such HSC population with $G_2M$ accumulation produced a myeloid-biased progeny that was not effectively rescued by a p38 MAPK inhibitor alone. However, it was surprisingly discovered that a combination of a p38 MAPK inhibitor and a HIF-1α stabilizer effectively reduced both DDR and $G_2M$ accumulation in HSCs including cycling or dividing HSCs, thereby reversing the myeloid skewing in HSCs, maintaining long term repopulating potential of HSCs, and/or increasing engraftment of HSCs transplanted in vivo. Thus, a combination of a p38 MAPK inhibitor and a HIF-1α stabilizer can synergistically enhance in vivo engraftment capacity of HSCs (including cycling HSCs, e.g., which are subjected to ex vivo manipulation such as extended culture and/or genetic manipulation) via blocking the p38 MAPK stress signaling in conjunction with stabilizing HIF-1α.

Accordingly, in some aspects, the present disclosure provides ex vivo cell culture methods for preserving the stemness of stem cells such as HSCs in the presence of one or more p38 MAPK inhibitors and one or more HIF-1α stabilizers. The combination of the p38 MAPK inhibitor and HIF-1α stabilizer not only suppresses at least DNA damage response due to extended ex vivo culture and/or genetic manipulation, but also reduces accumulation of HSCs in the GM2 phase of the cell cycle when the HSCs are genetically modified during cell division. In some instances, the stem cells may have undergone a manipulation that induces a DNA double-strand break, for example, transduction by a vector that is capable of integrating into the genome of the stem cells, or genome editing. Genome editing methods are generally classified based on the type of endonuclease that is involved in generating double stranded breaks in the target nucleic acid. Without wishing to be bound by any particular theory, ex vivo manipulation of HSCs may activate stress signaling, resulting in their commitment to hematopoietic progenitor cells (HPCs) at the expense of HSC self-renewal. Events that involve DNA double-strand breaks, (e.g., vector integration or gene editing events) may exacerbate HSC loss and particularly when the DNA double strand breaks occur in cycling cells. The present discovery showed that blocking the p38 MAPK signaling pathway in conjunction with stabilizing HIF-1α would rescue such HSC loss in ex vivo culturing and genetic manipulation. Accordingly, described herein are also ex vivo methods and compositions for preparing stem cells such as HSCs (including cycling or dividing HSCs) having enhanced engraftment activity using one or more p38 MAPK inhibitors in combination with one or more HIF-1α stabilizers. The methods and compositions described herein promote engraftment of HSCs in a subject (e.g., a human patient) after HSC transplantation. Enhancing HSC engraftment activity may include increasing the level of recovery of hematopoietic and/or immunologic function of the bone marrow (upon HSC transplantation). Alternatively or in addition, it may include increasing the rate at which this recovery occurs (e.g., time to achieve a particular milestone of engraftment).

I. p38 Mitogen-Activated Protein Kinases (MAPK) Inhibitors p38 mitogen-activated protein kinases (MAPKs) are a class of mitogen-activated protein kinases that are responsive to stress stimuli, such as cytokines, ultraviolet irradiation, heat shock, and/or osmotic shock. The p38 MAPK family includes four members, p38-α (MAPK14), p38-β (MAPK11), p38-γ (MAPK12/ERK6), and p38-δ (MAPK13/SAPK4), which are involved in a signaling cascade that controls cellular response to cytokine and stress. Inhibitors for any of the p38 MAPK members can be used in the ex vivo culturing methods described herein. In some examples, the inhibitors used herein are specific to one of the members, for example, specific to p38-α, p38-β, p38-γ, or p38-δ. In other examples, the p38 MAPK inhibitors are universal to two or more members of the p38 MAPK family. In one example, the inhibitors used herein are specific or selective to p38-α (MAPK14).

Wild-type p38 MAPK sequences (e.g., sequences of p38-α (MAPK14), p38-β (MAPK11), p38-γ (MAPK12/ERK6), and p38-δ (MAPK13/SAPK4)) of various species are available on the world wide web from the NCBI, including human, mouse, and rat. For example, the nucleotide sequence encoding an isoform of human p38-α (MAPK14) is available at NCBI under GenBank Accession No. NM_001315 and its corresponding amino acid sequence is provided under GenBank Accession No. NP_001306.

As used herein, the term "p38 MAPK inhibitor" refers to a molecule that partially or fully blocks, inhibits, or neutralizes a biological activity of a p38 MAPK protein. Suitable inhibitor molecules specifically include antagonist antibodies (e.g., full length antibodies or antibody fragments), fragments or amino acid sequence variants of native polypeptides, peptides, antisense oligonucleotides, small organic molecules, recombinant proteins or peptides, etc. Methods for identifying inhibitors of a polypeptide can comprise contacting a polypeptide with a candidate p38 MAPK inhibitor molecule and measuring a detectable change in one or more biological activities normally associated with the polypeptide.

A p38 MAPK inhibitor can be a molecule of any type that interferes with the signaling associated with at least one or more p38 MAPK family members (e.g., p38-α (MAPK14), p38-β (MAPK11), p38-γ (MAPK12/ERK6), and p38-δ (MAPK13/SAPK4)) in a cell, for example, either by decreasing transcription or translation of p38 MAPK-encoding nucleic acid, or by inhibiting or blocking p38 MAPK polypeptide activity, or both. In some examples, a p38 MAPK inhibitor is an agent that interferes with the signaling associated with p38-α (MAPK). Examples of p38 MAPK inhibitors include, but are not limited to, antisense polynucleotides, interfering RNAs, catalytic RNAs, RNA-DNA chimeras, p38 MAPK-specific aptamers, anti-p38 MAPK antibodies, p38 MAPK-binding fragments of anti-p38 MAPK antibodies, p38 MAPK-binding small molecules, p38 MAPK-binding peptides, and other polypeptides that specifically bind p38 MAPK (including, but not limited to, p38 MAPK-binding fragments of one or more p38 MAPK ligands, optionally fused to one or more additional domains), such that the interaction between the p38 MAPK inhibitor and p38 MAPK results in a reduction or cessation of P38 MAPK activity or expression. It will be understood by one of ordinary skill in the art that in some instances, a p38 MAPK inhibitor can antagonize or neutralize one p38 MAPK activity without affecting another p38 MAPK activity. For example, a desirable p38 MAPK inhibitor for use in certain of the methods herein is a p38 MAPK inhibitor that binds p38-α and blocks p38 MAPK signaling, e.g., without affecting or minimally affecting any of the other p38 MAPK interactions, for example, binding p38-β, p38-γ, and/or p38-δ.

In some embodiments, p38 MAPK inhibitors used for the methods described herein are cell-permeable.

In some embodiments, a p38 MAPK inhibitor is an agent that directly or indirectly inhibits or reduces DNA double strand breaks and/or DNA damage response in genetically manipulated stem cells such as HSCs, for example, wherein the DNA double strand breaks and/or DNA damage response are mediated by one or more family members of p38 MAPK (e.g., p38-α, p38-β, p38-γ, p38-α, and any combinations thereof). Accordingly, a p38 MAPK inhibitor can target the p38 MAPK (e.g., p38-α, p38-β, p38-γ, p38-δ, and any combinations thereof) or any of p38 MAPK's upstream molecules. Examples of p38 MAPK inhibitors include, without limitations, anti-p38-α molecules, anti-p38-β molecules, anti-p38-γ molecules, anti-p38-α molecules, and any combinations thereof. A p38 MAPK inhibitor can be a protein, a peptide, a peptidomimetic, an aptamer, a nucleic acid, an antibody, a small molecule, or any combinations thereof.

A p38 MAPK inhibitor can be a molecule (e.g., an antibody, an aptamer, or a small molecule) that interferes with the binding of one or more family members of p38 MAPK (e.g., p38-α, p38-β, p38-γ, p38-α, and any combinations thereof). Alternatively, the p38 MAPK inhibitor can be a molecule (e.g., a inhibitory polynucleotide or oligonucleotide such as interfering RNA or antisense oligonucleotide) that suppresses transcription and/or translation of one or more family members of p38 MAPK (e.g., p38-α, p38-β, p38-γ, p38-α, and any combinations thereof), thereby reducing the mRNA/protein level of this enzyme. The p38 MAPK inhibitor as described herein may reduce the P38 MAPK signaling in stem cells or HSCs (e.g., during ex vivo culture after genetic manipulation) by at least 20% or more, e.g., 30%, 40%, 50%, 60%, 70%, 80%, 90%, 95% or above. The inhibitory activity of such an inhibitor against p38 MAPK can be determined by conventional methods, e.g., measuring the phosphorylation level of p-p38, for example, using protein assays such as ELISA or Western blot.

In some embodiments, the p38 MAPK inhibitor is an antibody that specifically binds to one or more family members of p38 MAPK (e.g., p38-α, p38-β, p38-γ, p38-α, and any combinations thereof) and neutralizes its activity to activate p38 MAPK signaling pathway. As used herein, the term "antibody" as includes but is not limited to polyclonal, monoclonal, humanized, chimeric, Fab fragments, Fv fragments, F(ab') fragments and F(ab')2 fragments, as well as single chain antibodies (scFv), fusion proteins and other synthetic proteins which comprise the antigen-binding site of the antibody.

Antibodies can be made by the skilled person using methods and commercially available services and kits known in the art. Methods of preparation of monoclonal antibodies are well known in the art and include hybridoma technology and phage display technology. Further antibodies suitable for use in the present disclosure are described, for example, in the following publications: Antibodies A Laboratory Manual, Second edition. Edward A. Greenfield. Cold Spring Harbor Laboratory Press (Sep. 30, 2013); Making and Using Antibodies: A Practical Handbook, Second Edition. Eds. Gary C. Howard and Matthew R. Kaser. CRC Press (Jul. 29, 2013); Antibody Engineering: Methods and Protocols, Second Edition (Methods in Molecular Biology). Patrick Chames. Humana Press (Aug. 21, 2012); Monoclonal Antibodies: Methods and Protocols (Methods in Molecular Biology). Eds. Vincent Ossipow and Nicolas Fischer. Humana Press (Feb. 12, 2014); and Human Monoclonal Antibodies: Methods and Protocols (Methods in Molecular Biology). Michael Steinitz. Humana Press (Sep. 30, 2013)).

Antibodies may be produced by standard techniques, for example by immunization with the appropriate polypeptide or portion(s) thereof, or by using a phage display library. If polyclonal antibodies are desired, a selected mammal (e.g., mouse, rabbit, goat, horse, etc.) is immunized with an immunogenic polypeptide bearing a desired epitope(s), optionally haptenized to another polypeptide. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Serum from the immunized animal is collected and treated according to known procedures. If serum containing polyclonal antibodies to the desired epitope contains antibodies to other antigens, the polyclonal antibodies can be purified by immunoaffinity chromatography or any other method known in the art. Techniques for producing and processing polyclonal antisera are well known in the art.

A p38 MAPK inhibitor specifically binds to one member of p38 MAPK (e.g., p38-α, p38-β, p38-γ, or p38-δ) if the inhibitor binds to the specific member of p38 MAPK with a greater affinity than for an irrelevant polypeptide. In some embodiments, the inhibitor binds to one member of p38 MAPK (e.g., p38-α, p38-β, p38-γ, or p38-δ) with at least 5, or at least 10 or at least 50 times greater affinity than for the irrelevant polypeptide. In some embodiments, the inhibitor binds to one member of p38 MAPK (e.g., p38-α, p38-β, p38-γ, or p38-δ) with at least 100, or at least 1,000, or at least 10,000 times greater affinity than for the irrelevant polypeptide. Such binding may be determined by methods well known in the art, such surface plasmon resonance such as a BIACORE system. In some embodiments, the inhibitor has an affinity (as measured by a dissociation constant, $K_D$) for a specific member of p38 MAPK (e.g., p38-α, p38-β, p38-γ, or p38-δ) of at least $10^{-7}$ M, $10^{-1}$ M, $10^{-9}$ M, $10^{-10}$ M, or $10^{-11}$ M.

In some embodiments, the p38 MAPK inhibitor is a small molecule, such as a small organic molecule, which typically has a molecular weight less than 5,000 kDa. Suitable small molecules include those that bind to one or more family members of p38 MAPK (e.g., p38-α, p38-β, p38-γ, or p38-α) or a fragment thereof, and may be identified by methods such as screening large libraries of compounds (Beck-Sickinger & Weber (2001) Combinational Strategies in Biology and Chemistry (John Wiley & Sons, Chichester, Sussex); by structure-activity relationship by nuclear magnetic resonance (Shuker et al (1996) "Discovering high-affinity ligands for proteins: SAR by NMR. Science 274: 1531-1534); encoded self-assembling chemical libraries Melkko et al (2004) "Encoded self-assembling chemical libraries." Nature Biotechnol. 22: 568-574); DNA-templated chemistry (Gartner et al (2004) "DNA-tem plated organic synthesis and selection of a library of macrocycles. Science 305: 1601-1605); dynamic combinatorial chemistry (Ramstrom & Lehn (2002) "Drug discovery by dynamic combinatorial libraries." Nature Rev. Drug Discov. 1: 26-36); tethering (Arkin & Wells (2004) "Small-molecule inhibitors of protein-protein interactions: progressing towards the dream. Nature Rev. Drug Discov. 3: 301-317); and speed screen (Muckenschnabel et al (2004) "SpeedScreen: label-free liquid chromatography-mass spectrometry-based high-throughput screening for the discovery of orphan protein ligands." Anal. Biochem. 324: 241-249). Typically, small molecules will have a dissociation constant for P38 MAPK in the nanomolar range.

Examples of small molecule p38 MAPK inhibitors for use in the ex vivo culturing method described herein are provided in Table 1 below:

TABLE 1

Exemplary p38 MAPK Inhibitors

| Type | Inhibitor | Chemical Name |
|---|---|---|
| Prototypical pyridinyl imidazoles | SB203580 | 4-[5-(4-Fluorophenyl)-2-[4-(methylsulfonyl)phenyl]-1H-imidazol-4-yl]pyridine |
| | SKF-86002 | 6-(4-Fluorophenyl)-2,3-dihydro-5-(4-pyridinyl)imidazo[2,1-b]thiazole dihydrochloride |
| Aryl-pyridyl heterocycles | SB-242235 | 1-(4-piperidinyl)-4-(4-fluorophenyl)-5-(2-methoxy-4-pyrimidinyl) imidazole |
| | RWJ-67657 | 4-[4-(4-Fluorophenyl)-1-(3-phenylpropyl)-5-(4-pyridinyl)-1H-imidazol-2-yl]-3-butyn-1-ol |
| | SB 239065 | Not Available |
| Non-aryl-pyridyl heterocycles | RO3201195 | S-[5-amino-1-(4-fluorophenyl)-1H-pyrazol-4-yl]-[3-(2,3-dihydroxypropoxy)phenyl]methanone |
| | BIRB-796 | 1-[5-tert-butyl-2-(4-methylphenyl)pyrazol-3-yl]-3-[4-(2-morpholin-4-ylethoxy)naphthalen-1-yl]urea), |
| | VX-745 | 5-(2,6-dichlorophenyl)-2-(2,4-difluorophenylthio)-6H-pyrimido[1,6-b]pyridazin-6-one |
| Other | SB202190 | 4-[4-(4-fluorophenyl)-5-pyridin-4-yl-1,3-dihydroimidazol-2-ylidene]cyclohexa-2,5-dien-1-one, VX-702 6-(N-carbamoyl-2,6-difluoroanilino)-2-(2,4-difluorophenyl)pyridine-3-carboxamide |
| | LY2228820 | 5-[2-tert-butyl-4-(4-fluorophenyl)-1H-imidazol-5-yl]-3-(2,2-dimethylpropyl)imidazo[4,5-b]pyridin-2-amine; methanesulfonic acid |
| | PH-797804 | 3-[3-bromo-4-[(2,4-difluorophenyl)methoxy]-6-methyl-2-oxopyridin-1-yl]-N,4-dimethylbenzamide |
| | VX-702 | 6-(N-carbamoyl-2,6-difluoroanilino)-2-(2,4-difluorophenyl)pyridine-3-carboxamide) |
| | LY2228820 | 5-[2-tert-butyl-4-(4-fluorophenyl)-1H-imidazol-5-yl]-3-(2,2-dimethylpropyl)imidazo[4,5-b]pyridin-2-amine; methanesulfonic acid |
| | L-167307 (Selective imidazole) | 4-[2-(4-Fluorophenyl)-5-[4-(methylsulfinyl)phenyl]-1Hpyrrol-3-yl]pyridine |
| | Pyridinyl-oxazole inhibitor | Not Available |
| | RPR-200765A | ((2r,5r)-2-(4-(4-fluorophenyl)-5-(pyridin-4-yl)-1H-imidazol-2-yl)-5-methyl-1,3-dioxan-5-yl)(morpholino)methanone methanesulfonate |
| | RPR-238677 | Not Available |
| | FR167653 | 1-(7-(4-fluorophenyl)-1,2,3,4-tetrahydro-8-(4-pyridyl)pyrazolo(5,1-c)(1,2,4)triazin-2-yl)-2-phenylethanedione sulphate monohydrate |
| | SB-239063 | trans-1-(4-hydroxycyclohexyl)-4-(4-fluorophenyl)-5-(2-methoxypyridimidin-4-yl)imidazole |

Exemplary p38 MAPK inhibitors also include doramapimod (e.g., BIRB-796), ralimetinib (e.g., LY2228820 dimesylate), aminopyridine-based, ATP-competitive inhibitors of p38 MAPK (e.g., Vx702), pyridinyl imidazole inhibitors (e.g., SB203580), and any combinations thereof.

Other p38 MAPK inhibitors are well known in the art, for example, those described in U.S. Pat. Nos. 7,169,779, 6,635,644, 6,608,060, 6,632,945, 6,528,508, 6,509,363 (Heterocyclic inhibitors of p38), 6,147,080, 6,800,626, 6,093,742, 6,949,560 (Imidazo-substituted compounds), 6,852,740 (Pyrazole derivatives), 6,630,485, 6,759,410 (3,4-dihydro-(1 h)-quinazolin-2ones), 6,696,471 (Aminopyrrole compounds), 6,696,443 (Piperidine/piperazine-type inhibitors), 6,509,361 (1,5-diaryl substituted pyrazoles), 6,444,696 (pyrazole derivatives), and PCT patent publications WO2000017175, WO2000017204, WO1996021654, WO1999000357, WO1999064400, the relevant teachings of each of which is incorporated by reference herein. Other p38 MAPK inhibitors as described in Xing "Clinical candidates of small molecule p38 MAPK inhibitors for inflammatory diseases" (2015) MAP Kinase 4: 5508 may also be used for the ex vivo methods and compositions described herein.

In some embodiments, the p38 MAPK inhibitor is an interfering RNA such as a small interfering RNA (siRNA) short hairpin RNA (shRNA). In some embodiments, the p38 MAPK inhibitor is a small interfering RNA (siRNA) that binds to the mRNA of one or more family members of p38 MAPK (e.g., p38-α, p38-β, p38-γ, or p38-δ) and blocks its translation or degrades the mRNA via RNA interference. Exemplary small interfering RNAs are described by Hannon et al. Nature, 418 (6894): 244-51 (2002); Brummelkamp et al., Science 21, 21 (2002); and Sui et al., Proc. Natl Acad. Sci. USA 99, 5515-5520 (2002). RNA interference (RNAi) is the process of sequence-specific post-transcriptional gene silencing in animals initiated by double-stranded (dsRNA) that is homologous in sequence to the silenced gene. siRNAs are generally RNA duplexes with each strand being 20-25 (such as 19-21) base pairs in length. In some embodiments, the p38 MAPK inhibitor is a short hairpin RNA (shRNA) that is complementary to a p38 MAPK nucleic acid (e.g., a p38 MAPK mRNA). An shRNA typically contains of a stem of 19-29 base pairs, a loop of at least 4 nucleotides (nt), and optionally a dinucleotide overhang at the 3' end. Expression of shRNA in a subject can be obtained by delivery of a vector (e.g., a plasmid or viral or bacterial vectors) encoding the shRNA. siRNAs and shRNAs may be designed using any method known in the art or commercially available (see, e.g., products available from Dharmacon and Life Technologies). An siRNA may also comprise one or more chemical modifications, such as a base modification and/or a bond modification to at least improve its stability and binding affinity to the target mRNA.

In some embodiments, the p38 MAPK inhibitor is an antisense oligonucleotide that is complementary to a p38 MAPK nucleic acid (e.g., a p38 MAPK mRNA). Antisense oligonucleotides are generally single-stranded nucleic acids (either a DNA, RNA, or hybrid RNA-DNA molecule), which are complementary to a target nucleic acid sequence, such as a portion of a p38 MAPK mRNA. By binding to the target sequence, an RNA-RNA, a DNA-DNA, or RNA-DNA duplex is formed, thereby inhibiting the function or level of the target nucleic acid, such as by blocking the transcription, processing, poly(A) addition, replication, translation, or promoting inhibitory mechanisms of the cells, such as promoting mRNA degradation. In some embodiments, an antisense oligonucleotide is 10 to 40, 12 to 35, or 15 to 35 bases in length, or any integer in between. An antisense oligonucleotide can comprise one or more modified bases, such as 2-Aminopurine, 2,6-Diaminopurine (2-Amino-dA), 5-Bromo dU, 5-Methyl dC, deoxyInosine, Locked Nucleic Acid (LNA), 5-Nitroindole, 2'-O-Methyl bases, Hydroxymethyl dC, 2' Fluoro bases. An antisense oligonucleotide can comprise one or more modified bonds, such as a phosphorothioate bond.

In some embodiments, the p38 MAPK inhibitor is a ribozyme that is complementary to a p38 MAPK nucleic acid (e.g., a p38 MAPK mRNA) and cleaves the p38 MAPK nucleic acid. Ribozymes are RNA or RNA-protein complexes that cleave nucleic acids in a site-specific fashion.

Ribozymes have specific catalytic domains that possess endonuclease activity. The ribozymes of the present disclosure may be synthetic ribozymes, such as those described in U.S. Pat. No. 5,254,678. These synthetic ribozymes have separate hybridizing regions and catalytic regions; therefore, the hybridizing regions can be designed to recognize a target sequence, such as a p38 MAPK sequence.

siRNAs, shRNAs, ribozymes, and antisense oligonucleotides as described herein may be complementary to a p38 MAPK nucleic acid (e.g., a p38 MAPK mRNA), or a portion thereof. It is to be understood that complementarity includes 100% complementarity but does not necessarily exclude mismatches at one or more locations, resulting in, e.g., at least 80%, at least 90%, at least 95%, at least 98%, or at least 99% complementarity.

In some embodiments, the p38 MAPK inhibitor is a non-antibody peptide or protein. The peptide or protein may comprise an amino acid sequence that interferes with the p38 MAPK signaling. Proteins and peptides may be designed using any method known in the art, e.g., by screening libraries of proteins or peptides for binding to p38 MAPK or inhibition of p38 MAPK binding to a ligand, such as p38 MAPK.

The capability of a candidate compound, such as a small molecule, protein, or peptide, to bind to or interact with a p38 MAPK polypeptide or fragment thereof may be measured by any method of detecting/measuring a protein/protein interaction or other compound/protein interaction. Suitable methods include methods such as, for example, yeast two-hybrid interactions, co-purification, ELISA, co-immunoprecipitation and surface plasmon resonance methods. Thus, the candidate compound may be considered capable of binding to the polypeptide or fragment thereof if an interaction may be detected between the candidate compound and the polypeptide or fragment thereof by ELISA, co-immunoprecipitation or surface plasmon resonance methods or by a yeast two-hybrid interaction or co-purification method, all of which are known in the art. Screening assays which are capable of high throughput operation are also contemplated. Examples may include cell based assays and protein-protein binding assays.

Other examples of MAPK inhibitors suitable for use to reduce loss of stem cells (e.g., hematopoietic stem cells) during ex vivo culture and/or genetic manipulation for increasing in vivo engraftment of the stem cells are described in International Patent Publication No. WO 2017/075274, the relevant disclosures of which are incorporated by reference for the purposes or subject matter referenced herein.

II. Hypoxia Inducible Factor-1α (HIF-1α) Stabilizers

Hypoxia inducible factor-1α (HIF-1α) is an alpha subunit of transcription factor hypoxia inducible factor-1 (HIF-1), which is a heterodimer composed of an alpha and a beta subunit. HIF-1 functions as a master regulator of cellular and systemic homeostatic response to hypoxia by activating transcription of many genes, including those involved in energy metabolism, angiogenesis, apoptosis, and other genes whose protein products increase oxygen delivery or facilitate metabolic adaptation to hypoxia. HIF-1 thus plays an essential role in embryonic vascularization, tumor angiogenesis and pathophysiology of ischemic disease. In HEK cells and in microglial cells, HIF-1α regulates CXCR4 by interacting with hypoxia response elements (HREs) within the CXCR4 promotor. See, e.g., Staller et al. *Nature.* 2003; 425 (6955): 307-311; and Wang et al. *Biochem Biophys Res Commun.* 2008; 371(2): 283-288. Stabilizers for HIF-1α can be used in the ex vivo culturing methods described herein. In some examples, the stabilizers used herein are specific or selective to HIF-1α.

The stability and activity of the a subunit of HIF-1 can be regulated by its post-translational modifications such as hydroxylation, ubiquitination, acetylation, and phosphorylation. For example, in normoxia, hydroxylation of two proline residues and acetylation of a lysine residue at the oxygen-dependent degradation (ODD) domain of HIF-1a trigger its association with pVHL E3 ligase complex, leading to HIF-1α degradation via ubiquitin-proteasome pathway. In hypoxia, the HIF-1α subunit becomes stable and interacts with coactivators such as cAMP response element-binding protein binding protein/p300 and regulates the expression of target genes.

Wild-type HIF-1α sequences of various species and isoforms thereof are available on the world wide web from the NCBI, including human, mouse, and rat. For example, the nucleotide sequence encoding an isoform of human HIF-1α is available at NCBI under Accession No. NM_001530 and its corresponding amino acid sequence is under Accession No. NP_001521.

As used herein, the term "HIF-1α stabilizer" refers to a molecule that directly or indirectly stabilizes HIF-1α protein and/or its biological activity, e.g., stabilizes the HIF-1α protein level with minimal or no effect on HIF-1α mRNA expression; increases HIF-1α mRNA expression; or partially or fully blocks or inhibits degradation of HIF-1α protein or mRNA. Suitable stabilizer molecules specifically include agonistic antibodies (e.g., full length antibodies or antibody fragments), fragments or amino acid sequence variants of native polypeptides, peptides, small organic molecules, recombinant proteins or peptides, etc. Methods for identifying stabilizers of a polypeptide can comprise contacting a polypeptide with a candidate HIF-1α stabilizer molecule and measuring a detectable change in its level and/or one or more biological activities normally associated with the polypeptide.

A HIF-1α stabilizer can be a molecule of any type that inhibits hydroxylation of amino acid residues in the HIF-1α protein, e.g., as described in the U.S. Pat. App. No. US 2006/0270699, the relevant content of which is incorporated by reference for the purposes or subject matter referenced herein. In some embodiments, a HIF-1α stabilizer may be a molecule of any type that inhibits hydroxylation of one or two proline residues (e.g., Pro402 and Pro564 located within the ODD domain) in the HIF-1α protein.

In some embodiments, a HIF-1α stabilizer may be an inhibitor of a HIF-specific prolyl hydroxylase that initiates the degradation of HIF-1α. Examples of such inhibitors include, but are not limited to dimethyloxalylglycine (DMOG; also known as N-(methoxyoxoacetyl)-glycine), or 2-oxoglutarate (2-OG) or its analog thereof (e.g., Roxadustat, also known as FG-4592), or a derivative or analog thereof.

In some embodiments, a HIF-1α stabilizer may be a molecule of any type that inhibits acetylation of a lysine residue (e.g., Lys532 located in the ODD domain) in the HIF-1α protein.

In some embodiments, a HIF-1α stabilizer may be a molecule of any type that binds and activates the prostaglandin E2 receptor. Non-limiting examples of such HIF-1α stabilizers include prostaglandin E2 (PGE2) and its analogs or derivatives thereof, including, e.g., 16-16 dimethyl prostaglandin E2 (dmPGE2).

Other examples of HIF-1α stabilizers include dimethyl-2-ketoglutarate (DKG), desferrioxamine (DFO), an iron chelator, and any combinations thereof.

In some embodiments, a HIF-1α stabilizer may be diethyl fumarate (DEF) or a derivative or analog thereof.

In some embodiments, HIF-1α stabilizers used for the methods described herein are cell-permeable.

A HIF-1α stabilizer can be a molecule (e.g., an activating polynucleotide or oligonucleotide) that induces transcription and/or translation of HIF-1α, thereby increasing the mRNA/protein level of this protein. The HIF-1α stabilizers as described herein may increase the transcription and/or translation of HIF-1α in stem cells or HSCs (e.g., during ex vivo culture and/or genetic manipulation) by at least 20% or more, e.g., 30%, 40%, 50%, 60%, 70%, 80%, 90%, 95% or above. The activity of such a HIF-1α stabilizer can be determined by conventional methods, e.g., measuring the protein or mRNA level of HIF-1α, for example, using protein assays such as ELISA or Western blot.

In some embodiments, a HIF-1α stabilizer may be a HIF-1α protein or fragment thereof or a HIF-1α peptidomimetic. For example, mutation of one or two proline residues (e.g., Pro402 and/or Pro 564 located within the ODD domain) of HIF-1α disrupts the interaction of HIF-1α with pVHL and thus increases its stability in the presence of normal oxygen levels (e.g., during cell culture). As another example, mutation of Lys 532 (located in the ODD domain) of HIF-1α to arginine may result in increased stability of HIF-1α. See, e.g., Tanimoto et al. 2000. *EMBO (Eur Mol Biol Organ) J* 19: 4298-4309.

In some embodiments, a HIF-1α stabilizer is a small molecule, such as a small organic molecule, which typically has a molecular weight less than 5,000 kDa. Suitable small molecules include those that bind to one or more enzymes that initiate degradation pathway of HIF-1α or a fragment thereof, and may be identified by methods such as screening large libraries of compounds (Beck-Sickinger & Weber (2001) Combinational Strategies in Biology and Chemistry (John Wiley & Sons, Chichester, Sussex); by structure-activity relationship by nuclear magnetic resonance (Shuker et al (1996) "Discovering high-affinity ligands for proteins: SAR by NMR. Science 274: 1531-1534); encoded self-assembling chemical libraries Melkko et al (2004) "Encoded self-assembling chemical libraries." Nature Biotechnol. 22: 568-574); DNA-templated chemistry (Gartner et al (2004) "DNA-tem plated organic synthesis and selection of a library of macrocycles. Science 305: 1601-1605); dynamic combinatorial chemistry (Ramstrom & Lehn (2002) "Drug discovery by dynamic combinatorial libraries." Nature Rev. Drug Discov. 1: 26-36); tethering (Arkin & Wells (2004) "Small-molecule inhibitors of protein-protein interactions: progressing towards the dream. Nature Rev. Drug Discov. 3: 301-317); and speed screen (Muckenschnabel et al (2004) "SpeedScreen: label-free liquid chromatography-mass spectrometry-based high-throughput screening for the discovery of orphan protein ligands." Anal. Biochem. 324: 241-249). Typically, small molecules will have a dissociation constant for P38 MAPK in the nanomolar range.

III. Methods for Preserving Stemness of Stem Cells in Ex Vivo Culture

Any combination of the p38 MAPK inhibitors and HIF-1α stabilizers, e.g., those described herein, can be used for preserving stemness of stem cells (e.g., hematopoietic stem cells) in ex vivo or in vitro culture. Stemness refers to the ability of unspecialized cells to renew themselves as unspecialized cells but still retain this ability to specialize to produce specific types of cells. The stem cell potential, or "stemness" of stem cells (e.g., hematopoietic stem cells) relies upon a combination of properties: quiescence, repopulation potential, self-renewal potential, and multi-lineage differentiation potential. Cell-cycle quiescence in stem cells (e.g., HSCs) maintains stemness by protecting cells from differentiation or senescence.

The present disclosure features ex vivo culturing methods for preserving the stemness of stem cells in cell cultures by culturing stem cells (e.g., HSCs) in the presence of one or more p38 MAPK inhibitors and one or more HIF-1α stabilizers. The stem cell thus prepared can be used in treating suitable diseases via stem cell transplantation.

To perform the ex vivo culturing methods described herein, a suitable population of stem cells (e.g., pluripotent stem cells) can be obtained from a suitable source. In some instances the population of stem cells (e.g., HSCs) can be derived from a human subject, e.g., from the bone marrow cells, peripheral blood cells, and/or umbilical cord blood cells of the human subject, via a convention method. In some examples, the stem cells are adult stem cells (e.g., HSCs), which can be derived from the bone marrow or peripheral blood cells of a human adult. In some examples, the stem cell population is substantially free of umbilical stem cells.

In some embodiments, any of the stem cell populations described herein have undergone a genetic manipulation that causes a DNA damage, e.g., double strand breaks, dimerization or cross-linking, unpaired bases, modified bases, conversion of one base into another resulting in unpaired bases, chromatin unwinding or other modifications, etc. In some embodiments, any of the stem cell populations described herein has undergone a genetic manipulation that a double strand break. The double strand break and/or DNA damage response may be mediated by one or more family members of p38 MAPK (e.g., p38-α, p38-β, p38-γ, p38-α, and any combinations thereof). A genetic manipulation includes modifying, inserting, or deleting at least one of the genes in the stem cells (e.g., HSCs). Genetic manipulation may include transduction with a vector that is capable of being integrated into the cell genome or genome editing, including, e.g., non-homologous end joining (NHEJ)-mediated gene disruption by genome editing techniques and homology directed repair (HDR)-mediated genome editing techniques.

A "vector", as used herein is any nucleic acid vehicle (DNA or RNA) capable of facilitating the transfer of a nucleic acid molecule into stem cells (e.g., HSCs). In general, vectors include, but are not limited to, plasmids, phagemids, viral vectors, and other vehicles derived from viral or bacterial sources that have been manipulated by the insertion or incorporation of a target nucleotide sequence. Viral vectors include, but are not limited to vectors comprising nucleotide sequences derived from the genome of the following viruses: retrovirus; lentivirus; adenovirus; adeno-associated virus; SV40-type viruses; polyoma viruses; Epstein-Barr viruses; papilloma viruses; herpes virus; vaccinia virus; polio virus. One can readily employ other vectors not named but known to the art.

Viral vectors may be based on non-cytopathic eukaryotic viruses in which nonessential genes have been replaced with a target nucleotide sequence. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are known in the art. Other viral vectors include adenoviruses and adeno-associated viruses, which are double-stranded DNA viruses that have also been approved for human use in gene therapy. The adeno-associated virus can be engineered to be replication deficient and is capable of infecting a wide range of cell types and species. Lentiviral vectors are a type of retrovirus that can infect both dividing and non-dividing cells because their preintegration complex (virus "shell") can get through the intact membrane of the nucleus of the target cell. Exemplar lentiviral vectors include, but are not limited to those derived from HIV.

Other vectors include non-viral plasmid vectors, which have been extensively described in the art and are well known to those of skill in the art. See, e.g., Sambrook et al. Molecular Cloning: A Laboratory Manual. Cold Spring Harbor Laboratory Press; 4th edition (Jun. 15, 2012). Exemplary plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA.

Various genome editing techniques that are known in the art can be used to manipulate the stem cells (e.g., HSCs) that are involved in the methods described herein. For example, genome editing may involve uses of zinc finger nucleases (ZFN), transcription activator-like effector-based nuclease (TALEN), meganucleases, homing endonucleases, and/or CRISPR/Cas systems (e.g., CRISPR/Cas9 systems).

In some embodiments, the stem cells involved in the methods and/or compositions described herein (e.g., HSCs) have been genetically manipulated using a viral vector such as a retroviral vector or a lentiviral vector, or by gene editing methods as described herein. Accordingly, in some embodiments, the stem cells involved in the methods and/or compositions described herein are gene-modified stem cells (e.g., HSCs).

The genetic manipulation of the stem cells may be performed when the stem cells are resting cells (non-cycling), i.e., cells that are not dividing, or when the stem cells are cycling, i.e., cells that are dividing. For example, cell-cycle independent genetic manipulation methods (e.g., lentiviral transduction or non-homologous end joining (NHEJ)-mediated genome editing methods such as using zinc finger nucleases, homing endonucleases, TALENS or Cas9 nucleases) may utilize non-cycling and/or cycling cells, while cell-cycle dependent genetic manipulation methods (e.g., retroviral vector transduction or homology directed repair (HDR)-mediated genome editing methods) require cycling HSCs.

Resting cells may be in the quiescent G0 phase. Phenotypes of resting HSCs are known in the art and can be used to identify such HSCs for the methods and/or compositions described herein. For example, HSC-enriched population is at least CD34+ CD38-CD90+. Like all somatic cells, stem cells (e.g., HSCs) progress through the cell cycle, which is characterized by four phases: G1 (interphase), S (DNA synthesis phase), G2 (interphase) and M (mitosis phase). Stem cells (e.g., HSCs) that proceed past the restriction point in the G1 phase enter the S phase, whereas those that do not pass the restriction point remain undivided. These undivided cells can withdraw from the cell cycle and enter the G0 phase: a state in which cells are termed quiescent or dormant. Such resting cells in the G0 phase can either reversibly re-enter the cell cycle and divide or remain dormant, losing the potential to cycle and, in some cases, becoming senescent. Quiescence is thus a property that characterizes stem cells (e.g., HSCs) and allows them to maintain stemness of the cells.

Without wishing to be bound by theory, when the stem cells (e.g., HSCs) are genetically manipulated or modified before they enter a cell cycle (e.g., when the cells are non-cycling) and are subsequently cultured in the presence of a p38 MAPK inhibitor and optionally a HIF-1α stabilizer, the p38 MAPK inhibitor delays the transition of the stem cells (e.g., HSCs) to S phase, which may likely allow for stem cells (e.g., HSCs) to repair any DNA damage, e.g., induced by the genetic manipulation, and the optional HIF-1α stabilizer may help maintain lineage fate of the HSCs, thus retaining the stemness of the stem cells (e.g., HSCs). This may be characterized by retained long term repopulating potential and/or a balanced lineage production. Accordingly, in some embodiments of the stem cells involved in the methods and/or compositions described herein, the stem cells (e.g., HSCs) are non-cycling or non-dividing cells, e.g., the stem cells are in the quiescent G0 phase.

When the genetic manipulation-induced DNA double strand break occurs in cycling or dividing stem cells (e.g., HSCs), it was discovered that there was an accumulation of HSCs in the G2M phase, which was not observed otherwise when non-cycling stem cells (e.g., HSCs) were genetically modified. Without wishing to be bound by theory, when a DNA double strand break is induced in cycling HSCs, e.g., via genetic manipulation, the DNA damage response stalls the HSC in the G2M phase, and this delay results in HSCs that primarily produce a myeloid-biased progeny, with a concomitant increased number of HSCs showing phenotypes associated with exhaustion or aging (e.g., increased expression of Fzd3 and/or Wnt5b). However, when the dividing HSCs are cultured and/or genetically modified in the co-presence of a p38 MAPK inhibitor and a HIF-1α stabilizer, the combined treatment reduces G2M accumulation as well as DNA damage response in the HSCs and restores the HSC lineage fate, thus retaining the stemness of the stem cells (e.g., HSCs). This may be characterized by retained long term repopulating potential and/or a balanced lineage production. Accordingly, in some embodiments of the stem cells involved in the methods and/or compositions described herein, the stem cells (e.g., HSCs) are cycling or dividing stem cells (e.g., HSCs). The non-cycling and cycling stem cells (e.g., HSCs) can be identified, for example, by measuring p34 (Cdk2) mRNA expression in the cells. Cycling stem cells (e.g., HSCs) generally have a higher level of p34 (Cdk2) mRNA expression than that of non-cycling stem cells (e.g., HSCs). See, for example, FIG. 17, Panel B.

Any of the stem cell populations described herein can be cultured in a suitable medium (e.g., cell culture medium) in the presence of an effective amount of one or more p38 MAPK inhibitors as those described herein in conjunction with an effective amount of one or more HIF-1α stabilizers as those described herein for a suitable period of time, e.g., at least 18 hours, at least about 24 hour, at least 36 hours, at least 48 hours, at least 60 hours, at least 72 hours, at least 84 hours, at least 96 hours, at least about 5 days, at least about 6 days, at least about 7 days, or longer. In some embodiments, any of the stem cell populations described herein can be cultured in a suitable medium (e.g., cell culture medium) in the presence of an effective amount of one or more p38 MAPK inhibitors as those described herein in conjunction with an effective amount of one or more HIF-1α stabilizers as those described herein for about 18 hours to about 7 days, or about 1 day to about 7 days, or about 2 days to about 7 days, or about 3 days to about 7 days, or longer.

In any of the methods described herein, the stem cells may be cultured in the simultaneous presence of one or more p38 MAPK inhibitors as those described herein and one or more HIF-1α stabilizers as those described herein. For example, the p38 MAPK inhibitor(s) and the HIF-1α stabilizer(s) may be simultaneously added to the stem cell culture. Alternatively, the p38 MAPK inhibitor(s) and the HIF-1α stabilizer(s) may be added to the stem cell culture in a sequential manner such that the stem cells are ultimately cultured in the simultaneous presence of both the p38 MAPK inhibitor(s) and the HIF-1α stabilizer(s).

In some embodiments, the stem cells involved in the methods described herein may be first cultured in the presence of one or more p38 MAPK inhibitors as those described herein for a an appropriate period of time, and then cultured in the presence of one or more HIF-1α stabilizers as those described herein (with substantially no p38 MAPK inhibitors present or with one or more p38 MAPK inhibitors in concentrations that are lower than that used in the prior culture), or vice versa.

An "effective amount" or an "amount effective to", as used herein, refers to an individual amount of a p38 MAPK inhibitor and a HIF-1α stabilizer as described herein such that when both the p38 MAPK inhibitor and the HIF-1α stabilizer are present, the combination is effective in preserving at least one characteristic of the stemness (quiescence, repopulation potential, self-renewal potential, and multi-lineage differentiation potential) of stem cells, e.g., HSCS, and/or results in a desired clinical effect, such as increased engraftment of HSCs in a subject after HSC transplantation. This can be monitored by routine methods or can be monitored according to the method for assessing engraftment of HSCs described herein. Effective amounts of a p38 MAPK inhibitor and a HIF-1α stabilizer can be determined separately and/or in combination. Effective amounts vary, as recognized by those skilled in the art, depending on, for example, the potency of the p38 MAPK inhibitor and HIF-1α stabilizer used, and/also the cell cycle status (e.g., cycling vs. non-cycling) of the stem cells (e.g., HSCs) during which the cells are cultured and/or genetically modified.

For example, the effective amount of a p38 MAPK inhibitor for culturing the stem cells (e.g., HSCs) in the methods described herein results in an increase in the proportion of stem cells (e.g., HSCs) in the G0 quiescent phase by at least about 10% or more, including, e.g., at least about 20%, at least about 30%, at least about 40%, at least about 50%, at least about 60%, at least about 70%, at least about 80%, at least about 90% or more, as compared to the proportion of stem cells (e.g., HSCs) in the G0 quiescent phase without culturing in the presence of a p38 MAPK inhibitor. In some embodiments, the effective amount of a p38 MAPK inhibitor results in an increase in the proportion of stem cells (e.g., HSCs) in the G0 quiescent phase by at least about 1.1-fold or more, including, e.g., at least about 2-fold at least about 3-fold, at least about 4-fold, at least about 5-fold, at least about 6-fold, at least about 7-fold, at least about 8-fold, at least about 9-fold, at least about 10-fold or more, as compared to the proportion of stem cells (e.g., HSCs) in the G0 quiescent phase without culturing in the presence of a p38 MAPK inhibitor.

In some embodiments, the effective amount of a p38 MAPK inhibitor used in the methods described herein results in a decrease in the proportion of the stem cells (e.g., HSCs) in the S-G2-M phase before the first cell division cycle (e.g., 24 hours) by at least about 10% or more, including, e.g., at least about 20%, at least about 30%, at least about 40%, at least about 50%, at least about 60%, at least about 70%, at least about 80%, at least about 90% or more, as compared to the proportion of stem cells (e.g., HSCs) in the S-G2-M phase before the first cell division cycle without culturing in the presence of a p38 MAPK inhibitor.

In some embodiments of the methods described herein, the stem cells (e.g., HSCs) are cultured in the presence of a p38 MAPK inhibitor in an amount effective to reduce DNA damage or DNA double strand break (e.g., as measured by the expression of γH2AX foci or 53bp1) in the stem cells (e.g., HSCs) by at least about 20% or more, including, at least about 30%, at least about 40%, at least about 50%, at least about 60%, at least about 70%, at least about 80%, at least about 90% or more, as compared to the level of DNA damage or DNA double strand break measured in stem cells without culturing in the presence of a p38 MAPK inhibitor.

In some embodiments of the methods described herein, the effective amount of a p38 MAPK inhibitor for culturing the stem cells (e.g., HSCs) results in a decrease in the phosphorylation level of at least one or more (including, e.g., at least two, or at least three) members of p38 MAPK (e.g., p38-α, p38-β, p38-γ, or p38-δ) in the stem cells (e.g., HSCs), for example, by at least about 20%, including, for example, at least about 30%, at least about 40%, at least about 50%, at least about 60%, at least about 70%, at least about 80%, or more, as compared to the phosphorylation level of the corresponding member of p38 MAPK in the stem cells (e.g., HSCs) without the treatment of the p38 MAPK inhibitor.

In some embodiments of the methods described herein, the effective amount of a p38 MAPK inhibitor does not substantially increase the phosphorylation level of ERK or JNK in the stem cells (e.g., HSCs), for example, by no more than 20%, including, for example, no more than 10%, no more than 5%, no more than 3%, or lower, as compared to the phosphorylation level of ERK or JNK in the stem cells (e.g., HSCs) without the treatment of the p38 MAPK inhibitor.

An effective dose of a p38 MAPK inhibitor for the methods described herein can be at least about 10 nM, at least about 20 nM, at least about 30 nM, at least about 40 nM, at least about 50 nM, at least about 100 nM, at least about 200 nM, at least about 300 nM, at least about 400 nM, at least about 500 nM, at least about 600 nM, at least about 700 nM, at least about 800 nM, at least about 900 nM, at least about 1 μM, at least about 2 μM, at least 3 μM, at least about 4 μM, at least about 5 μM, at least about 6 μM, at least about 7 μM, at least about 8 μM, at least about 9 μM, or at least about 10 μM. In some embodiments, the effective dose of a p38 MAPK inhibitor for the methods described herein can be no more than 10 μM, no more than 9 μM, no more than 8 μM, no more than 7 μM, no more than 6 μM, no more than 5 μM, no more than 4 μM, no more than 3 μM, no more than 2 μM, no more than 1 μM, no more than 900 nM, no more than 800 nM, no more than 700 nM, no more than 600 nM, no more than 500 nM, no more than 400 nM, no more than 300 nM, no more than 200 nM, no more than 100 nM, no more than 50 nM, no more than 40 nM, no more than 30 nM, no more than 20 nM, or no more than 10 nM. Combinations of the above-referenced ranges are also possible. For example, an effective dose of a p38 MAPK inhibitor for the methods described herein can be about 30 nM to about 10 µM, or about 100 nM to about 5 µM, or about 400 nM to about 800 nM.

In some embodiments of the methods and/or compositions described herein, the effective amount of HIF-1α is selected such that it is effective to stabilize HIF-1α protein and/or transcriptional activity in the stem cells (e.g., HSCs) by at least about 20% or more, including, at least about 30%, at least about 40%, at least about 50%, at least about 60%, at least about 70%, at least about 80%, at least about 90% or more, as compared to the HIF-1α protein and/or transcriptional activity level measured in stem cells without culturing in the presence of a HIF-1α stabilizer. The HIF-1α protein level can be measured, e.g., by protein assay such as ELISA or western blot. The transcriptional activity of HIF-1α can be detected, e.g., by measuring activity and/or level of HIF-1α downstream responsive gene(s).

In some embodiments, the effective amount of a HIF-1α stabilizer selected for use in the methods and/or compositions described herein results in upregulation of CXCR4 expression and/or activity level in the stem cells (e.g., HSCs) by at least about 10% or more, including, e.g., at least about 20%, at least about 30%, at least about 40%, at least about 50%, at least about 60%, at least about 70%, at least about 80%, at least about 90% or more, as compared to the CXCR4 expression and/or activity level in HSCs without culturing in the presence of a HIF-1α stabilizer. In some embodiments, the effective amount of a HIF-1α stabilizer results in in upregulation of CXCR4 expression and/or activity level in the stem cells (e.g., HSCs) by at least about 1.1-fold or more, including, e.g., at least about 2-fold at least about 3-fold, at least about 4-fold, at least about 5-fold, at least about 6-fold, at least about 7-fold, at least about 8-fold, at least about 9-fold, at least about 10-fold or more, as compared to the CXCR4 expression and/or activity level in HSCs without culturing in the presence of a HIF-1α stabilizer.

An effective dose of a HIF-1α stabilizer for the methods described herein can be at least about 10 nM, at least about 20 nM, at least about 30 nM, at least about 40 nM, at least about 50 nM, at least about 100 nM, at least about 200 nM, at least about 300 nM, at least about 400 nM, at least about 500 nM, at least about 600 nM, at least about 700 nM, at least about 800 nM, at least about 900 nM, at least about 1 µM, at least about 2 µM, at least about 3 µM, at least about 4 µM, at least about 5 µM, at least about 6 µM, at least about 7 µM, at least about 8 µM, at least about 9 µM, at least about 10 µM, at least about 20 µM, or more. In some embodiments, the effective dose of a HIF-1α stabilizer for the methods described herein can be no more than 20 µM, no more than 10 µM, no more than 9 µM, no more than 8 µM, no more than 7 µM, no more than 6 µM, no more than 5 µM, no more than 4 µM, no more than 3 µM, no more than 2 µM, no more than 1 µM, no more than 900 nM, no more than 800 nM, no more than 700 nM, no more than 600 nM, no more than 500 nM, no more than 400 nM, no more than 300 nM, no more than 200 nM, no more than 100 nM, no more than 50 nM, no more than 40 nM, no more than 30 nM, no more than 20 nM, or no more than 10 nM. Combinations of the above-referenced ranges are also possible. For example, an effective dose of a HIF-1α stabilizer for the methods described herein can be about 30 nM to about 20 µM, or about 100 nM to about 10 µM, or about 500 nM to about 10 µM.

In some embodiments of the methods described herein, the stem cells (e.g., dividing or cycling HSCs) are cultured in the presence of a p38 MAPK inhibitor and a HIF-1α stabilizer in amounts, when combined, effective to reduce accumulation of the stem cells (e.g., HSCs) in the G2M phase of the cell cycle, for example, as assessed by cell immunostaining with anti-Ki-67 antibody and Hoechst stains, by at least about 20% or more, including, at least about 30%, at least about 40%, at least about 50%, at least about 60%, at least about 70%, at least about 80%, at least about 90% or more, as compared to the $G_2M$ accumulation in stem cells (e.g., dividing or cycling HSCs) cultured without a p38 MAPK inhibitor or a HIF-1α stabilizer. Example 1 including FIG. 14 describes an exemplary method to perform cell cycle analysis.

In some embodiments of the methods described herein, the stem cells (e.g., dividing or cycling HSCs) are cultured in the presence of a p38 MAPK inhibitor and a HIF-1α stabilizer in amounts, when combined, effective to reduce loss of long term repopulating potential (LTRP) (e.g., as assessed in secondary transplant (2 T)) by at least about 20% or more, including, at least about 30%, at least about 40%, at least about 50%, at least about 60%, at least about 70%, at least about 80%, at least about 90% or more, as compared to the LTRP when the cells are cultured without a p38 MAPK inhibitor or a HIF-1α stabilizer. Example 1 including FIG. 2 (Panel B) describes an exemplary method to determine LTRP in 2 T xenografts.

In some embodiments of the methods described herein, the stem cells (e.g., dividing or cycling HSCs) are cultured in the presence of a p38 MAPK inhibitor and a HIF-1α stabilizer in amounts, when combined, effective to reduce myeloid skewing bias in the stem cells by at least about 20% or more, including, at least about 30%, at least about 40%, at least about 50%, at least about 60%, at least about 70%, at least about 80%, at least about 90% or more, as compared to the myeloid skewing bias when the cells are cultured without a p38 MAPK inhibitor or a HIF-1α stabilizer. Example 1, including FIG. 2 (Panel B) and FIG. 3, describes an exemplary method for multi-lineage reconstitution to assess myeloid skewing bias.

In some embodiments, the stem cells (e.g., HSCs), prior to transplantation in vivo, are cultured in a medium comprising an effective amount of a p38 inhibitor as described herein and an effective amount of a HIF-1α stabilizer as described herein, wherein the combination results in an increase in subsequent engraftment of stem cells (e.g., HSCs) in vivo by at least about 10% or more, including, e.g., at least about 20%, at least about 30%, at least about 40%, at least about 50%, at least about 60%, at least about 70%, at least about 80%, at least about 90% or more, as compared to engraftment of stem cells (e.g., HSCs) without culturing the cells with a p38 MAPK inhibitor or a HIF-1α stabilizer prior to transplantation. In some embodiments, the combined effective amounts of a p38 MAPK inhibitor and a HIF-1α stabilizer result in an increase in subsequent engraftment of stem cells (e.g., HSCs) by at least about 1.1-fold or more, including, e.g., at least about 2-fold at least about 3-fold, at least about 4-fold, at least about 5-fold, at least about 6-fold, at least about 7-fold, at least about 8-fold, at least about 9-fold, at least about 10-fold or more, as compared to engraftment of stem cells (e.g., HSCs) without culturing the cells with a p38 MAPK inhibitor or a HIF-1α stabilizer prior to transplantation.

Combinations of the above-referenced effective amounts of a p38 MAPK inhibitor and a HIF-1α stabilizer are possible. For example, in some embodiments, the stem cells (e.g., HSCs) are cultured in the presence of a p38 MAPK inhibitor and a HIF-1α stabilizer, wherein the effective amount of the p38 MAPK inhibitor is sufficient to reduce DNA damage or DNA double strand break (e.g., as measured by the expression of γH2AX foci or 53bp1) in the stem cells (e.g., HSCs) by at least about 20% or more, including, at least about 30%, at least about 40%, at least about 50%, at least about 60%, at least about 70%, at least about 80%, at least about 90% or more, as compared to the level of DNA damage or DNA double strand break measured in stem cells without culturing in the presence of a p38 MAPK inhibitor; while the effective amount of the HIF-1α stabilizer is sufficient to stabilize HIF-1α protein and/or transcriptional activity in the stem cells (e.g., HSCs) by at least about 20% or more, including, at least about 30%, at least about 40%, at least about 50%, at least about 60%, at least about 70%, at least about 80%, at least about 90% or more, as compared to the HIF-1α protein and/or transcriptional activity level measured in stem cells without culturing in the presence of a HIF-1α stabilizer.

In some embodiments, the stem cells (e.g., HSCs) are cultured, prior to in vivo transplantation, in the presence of a p38 MAPK inhibitor and a HIF-1α stabilizer, wherein the effective amount of the p38 MAPK inhibitor is sufficient to reduce DNA damage or DNA double strand break (e.g., as measured by the expression of γH2AX foci or 53bp1) in the stem cells (e.g., HSCs) by at least about 20% or more, including, at least about 30%, at least about 40%, at least about 50%, at least about 60%, at least about 70%, at least about 80%, at least about 90% or more, as compared to the level of DNA damage or DNA double strand break measured in stem cells without culturing in the presence of a p38 MAPK inhibitor; while the amount of the HIF-1α stabilizer is selected such that when combined with the selected amount of the p38 MAPK inhibitor, the combined effective amount of the p38 MAPK inhibitor and the HIF-1α stabilizer results in an increase in subsequent engraftment of stem cells (e.g., HSCs) in vivo by at least about 10% or more, including, e.g., at least about 20%, at least about 30%, at least about 40%, at least about 50%, at least about 60%, at least about 70%, at least about 80%, at least about 90% or more, as compared to engraftment of stem cells (e.g., HSCs) without culturing the cells with a p38 MAPK inhibitor or a HIF-1α stabilizer prior to transplantation. In some embodiments, the combined effective amount of a p38 MAPK inhibitor and a HIF-1α stabilizer results in an increase in subsequent engraftment of stem cells (e.g., HSCs) by at least about 1.1-fold or more, including, e.g., at least about 2-fold at least about 3-fold, at least about 4-fold, at least about 5-fold, at least about 6-fold, at least about 7-fold, at least about 8-fold, at least about 9-fold, at least about 10-fold or more, as compared to engraftment of stem cells (e.g., HSCs) without culturing the cells with a p38 MAPK inhibitor or a HIF-1α stabilizer prior to transplantation.

In some instances, the combination of a p38 MAPK inhibitor and a HIF-1α stabilizer may display a synergistic effect on the stem cells (e.g., HSCs such as cycling or dividing HSCs). As used herein, the term "synergistic effect" as used herein, refers to action of two agents such as, for example, a p38 MAPK inhibitor and a HIF-1α stabilizer, producing an effect, for example, maintaining the stemness of stem cells (e.g., HSCs) and/or increasing the engraftment efficiency of transplanted stem cells (e.g., HSCs), which is greater than the simple addition of the effects of each agent administered by themselves. For example, the combination of a p38 MAPK inhibitor and a HIF-1α stabilizer enhances in vivo engraftment of cycling or dividing stem cells that have undergone in vitro or ex vivo manipulation (e.g., cell culture and/or genetic manipulation), but absence of either agent fails to do so. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the combination of a p38 MAPK inhibitor and a HIF-1α stabilizer. The corresponding graphs associated with the equations referred to above are the concentration-effect curve, isobologram curve and combination index curve, respectively.

The stem cells can preserve their stemness when they are cultured in the presence of a p38 MAPK inhibitor and a HIF-1α stabilizer according to the methods described herein. In some embodiments, the percentage of pluripotent stem cells after the ex vivo culturing process is at least 70% (e.g., 80%, 90%, 95%, 97%, or above) of that before the ex vivo culture. In other embodiments, less than 30% (e.g., less than 25%, 20%, 15%, 10%, or 5% or less) of the stem cells would differentiate, e.g., from pluripotent stem cells to multipotent stem cells, or from multipotent cells to specialized cells, during the ex vivo culture process described herein. The presence of different types of stem cells, e.g., pluripotent stem cells and multipotent cells, and specialized cells in the ex vivo culture can be monitored via a routine method, for example monitored by the presence of cell surface markers specific to a specific type of stem cells or specific to a specialized cell.

In some embodiments, adult HSCs are subjected to the ex vivo culturing process described herein, which involves the use of one or more p38 MAPK inhibitors and one or more HIF-1α stabilizers. The percentage of HSCs after the culturing may be at least 70% (e.g., 80%, 90%, 95%, or higher) of that of HSCs prior to the culturing. Alternatively or in addition, the percentage of hematopoietic progenitor cells (HPCs) in the cells after the ex vivo culture may be lower than 30% (e.g., lower than 25%, 20%, 15%, 10%, or 5%).

IV. Stem Cell Therapy

The stem cells prepared by the ex vivo culturing methods described herein can be used in stem-cell therapy, which is the use of stem cells to treat or prevent a disease or condition, including, for example, neurodegenerative diseases and conditions, diabetes, heart disease, and other conditions. Examples of suitable conditions to be treated by stem cell therapy include, but are not limited to, acute myeloid leukemia (AML), chronic myeloid leukemia (CML), acute lymphoblastic leukemia (ALL), Hodgkin lymphoma, Non-Hodgkin lymphoma, neuroblastoma, Ewing sarcoma, Myelodysplastic syndromes, Gliomas, and other solid tumors. Stem cell therapy can also be applied to non-malignant conditions such as thalassemia, aplastic anemia, Fanconi anemia, immune deficiency syndromes, or inborn errors of metabolism. In some embodiments, the HSCs prepared by the ex vivo culturing methods described herein can be used for transplantation in treatment of hematopoietic disorders, including, but not limited to, acute myeloid leukemia (AML), chronic myeloid leukemia (CML), acute lymphoblastic leukemia (ALL), chronic lymphocytic leukemia (CLL), juvenile myelomonocytic leukemia, Hodgkin lymphoma, and Non-Hodgkin lymphoma.

Hematopoietic stem cell transplantation (HSCT) is the transplantation of multipotent hematopoietic stem cells, usually derived from bone marrow, peripheral blood, or umbilical cord blood. In some instances, the HSCs can be autologous (the patient's own stem cells are cultured by the ex vivo culturing methods described herein and used for treating a disease). In other examples, the HSCs cay be allogeneic (the stem cells come from a donor and is then cultured by the ex vivo culturing methods described herein). Such HSCs can be used for treating certain cancers of the blood or bone marrow, such as multiple myeloma or leukemia. In these cases, the recipient's immune system is usually destroyed with radiation or chemotherapy before the transplantation.

In some examples, the HSCs described herein (e.g., human adult HSCs) can be genetically engineered to express a γ globin for use in treating anemia, such as sickle cell anemia and thalassemia. See, e.g., US20110294114 and WO2015/117027, the relevant teachings of each of which are incorporated by reference for the purposes or subject matter referenced herein.

In any of the stem cell therapy described herein, suitable stem cells can be collected from the ex vivo culturing method described herein and mixed with a pharmaceutically acceptable carrier to form a pharmaceutical composition, which is also within the scope of the present disclosure.

To perform the treatment methods described herein, an effective amount or dose of the stem cells can be administered into a subject in need of the treatment. The dose of HSCs that have been cultured in the presence of a p38 MAPK inhibitor and a HIF-1α stabilizer for administration or transplantation may vary with individual subjects in need thereof. The HSCs that have been cultured in the presence of a p38 MAPK inhibitor and a HIF-1α stabilizer may be administered or transplanted at a dose that is lower than that of HSCs that are treated with none or either one of the p38 MAPK inhibitor and the HIF-1α stabilizer. For example, a dose of about 50,000 to about 500,000 HSCs that have been cultured in the presence of a p38 MAPK inhibitor and a HIF-1α stabilizer may be administered to the subject. As another example, a dose of about 50,000 to about 100,000 HSCs that have been cultured in the presence of a p38 MAPK inhibitor and a HIF-1α stabilizer may be administered to the subject. In some instances, a dose of about 50,000, about 60,000, about 70,000, about 80,000, about 90,000, about 100,000, about 200,000, about 300,000, about 400,000, or about 500,000 HSCs that have been cultured in the presence of a p38 MAPK inhibitor and a HIF-1α stabilizer may be administered to the subject. A dose of lower than 50,000 HSCs prepared by any of the methods described herein is also possible.

The stem cells may be autologous to the subject. Administration of autologous cells to a subject may result in reduced rejection of the stem cells as compared to administration of non-autologous cells. Alternatively, the stem cells are allogeneic cells. For example, allogeneic stem cells may be derived from a human donor and administered to a human recipient who is different from the donor.

In some embodiments, the stem cells can be co-used with a therapeutic agent for a target disease, such as those described herein. The efficacy of the stem cell therapy described herein may be assessed by any method known in the art and would be evident to a skilled medical professional. Determination of whether an amount of the cells or compositions described herein achieved the therapeutic effect would be evident to one of skill in the art. Effective amounts may vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. In some embodiments, the effective amount alleviates, relieves, ameliorates, improves, reduces the symptoms, or delays the progression of any disease or disorder in the subject.

V. Evaluation of Stem Cell Engraftment Capacity

To assess engraftment of human hematopoietic stem cells (HSCs), such as the human HSCs prepared by any of the ex vivo culturing methods described herein, HSCs can be obtained or derived from a human subject who is need of a HSC transplantation and transplanted into a suitable immune deficient animal, such as an immune deficient mouse (e.g., an NSG mouse). Other suitable immune deficient animals are also known in the art, for example, those provided by Charles River Laboratories (see Table 2 below):

TABLE 2

Exemplary Immune Deficient Animals

| Strain | Hair | T-Cell Deficient | B-Cell Deficient | NK Cell Deficient |
|---|---|---|---|---|
| Athymic Nude Mouse | No | Yes | No | No |
| CD-1 Nude Mouse | No | Yes | No | No |
| NU/NU Nude Mouse | No | Yes | No | No |
| BALB/c Nude Mouse | No | Yes | No | No |
| NIH-III Mouse | No | Yes | Yes | Impaired |
| RNU Nude Rat | No | Yes | No | No |
| SCID Hairless Outbred (SHO) Mouse | No | Yes | Yes | No |
| SCID Hairless Congenic (SHC ™) Mouse | No | Yes | Yes | No |
| Fox Chase SCID Mouse | Yes | Yes | Yes | No |
| Fox Chase SCID Beige Mouse | Yes | Yes | Yes | Impaired |
| NOD SCID Mouse | Yes | Yes | Yes | Impaired |

After a suitable period of time, the mobilized peripheral blood of the recipient animal can be collected and the level of CD45$^+$ cells therein can be measured by a conventional method, e.g., FACS. The level of CD45$^+$ cells is in a reverse correlation to the rate of human HSC engraftment.

VI. Kits for Use in Preserving the Stemness of Stem Cells

The present disclosure also provides kits or compositions for use in preserving the stemness of stem cells (e.g., HSCs) or increasing stem cell engraftment in a subject need thereof. Such kits or compositions can include one or more containers comprising a p38 MAPK inhibitor and a HIF-1α stabilizer, and optionally, one or populations of stem cells (e.g., HSCs). The kits or compositions may further comprise a cell culture medium suitable for culturing stem cells (e.g., HSCs).

In some embodiments, the kit can comprise instructions for use in accordance with any of the methods described herein. The included instructions can comprise a description of culturing stem cells (e.g., HSCs) in a medium comprising an effective amount of a p38 MAPK inhibitor as described herein and an effective amount of a HIF-1α stabilizer. The kit may further comprise a description of selecting specific stem cells, e.g., HSCs, based on identifying surface markers associated with specific stem cells (e.g., CD34+CD38−CD90+ for HSCs). In still other embodiments, the instructions comprise a description of administering the HSCs to an individual in need of the treatment.

The instructions relating to the use of a p38 MAPK inhibitor and/or a HIF-1α stabilizer generally include information as to dosage, and dosing schedule for the intended treatment of stem cells (e.g., HSCs). The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for preserving the stemness of stem cells (e.g., HSCs). Instructions may be provided for practicing any of the methods described herein.

The kits of this invention are in suitable packaging. Suitable packaging includes, but is not limited to, vials, bottles, jars, flexible packaging (e.g., sealed MYLAR® (Biaxially-oriented polyethylene terephthalate) or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Examples: Culturing Hematopoietic Stem Cells (HSCs) in the Presence of a p38 Mitogen-Activated Protein Kinase (MAPK) Inhibitor and a Hypoxia Inducible Factor-1α (HIF-1α) Stabilizer to Maintain Stemness of HSCs Summary Gene therapy (GT) is an attractive alternative to allogenic hematopoietic stem cell transplantation (HSCT) to cure patients with monogenic disorders who lack a suitable transplant donor[1,2,3-15]. Its success depends on the ability of the gene-modified hematopoietic stem cells (HSCs) to differentiate into hematopoietic progenitor cells (HPCs) to regenerate the hematopoietic system, while simultaneously self-renew and regenerate themselves to sustain life-long blood cell production[16-18]. For GT, $CD34^+$ hematopoietic stem and progenitor cells (HSPCs) containing the rare HSCs ($CD34^+38^-90^+45RA^-49f^+$)[19] are cultured for 2-4 days in cytokine-rich medium that enforces HSC division, making them more amenable to genetic manipulation[20], and then transplanted following pre-transplant chemotherapy conditioning.

GT trials using γ-retroviral vectors (RV), which only transduce dividing cells, were largely unsuccessful, or modestly successful only with 5-30 times higher transduced $CD34^+$ HSPCs than that used for HSCT[21], except for treating immune deficiency disorders (IDDs)[1,2] Success in treatment of immune deficiency disorders (IDDs) were reported because a few engrafting gene-modified HSCs are capable of producing the long-lived lymphoid progeny with tremendous amplification potential[1,2]. Gene editing (GE) approaches require conditions similar to RV gene transfer—e.g., cycling HSCs, especially for homology directed repair (HDR)[22-27]. Like RV, with GE, high editing efficiencies in vitro do not translate to high LTRP in vivo[23,28,29]. Lentivirus vectors (LV) that transduce non-dividing cells have had more success, but, other than in IDD[30], success has been achieved with very high HSPC dose, and myeloablative chemotherapy conditioning. LV-transduced HSCs are otherwise unable to compete with the residual HSCs, despite residual HSCs being compromised with the high-dose chemotherapy[31-33]. The tremendous HSC loss, even with LV, is evidenced by presence of a few hundred to thousand common integrants in multiple blood cell lineages in patients, which is 2-3 orders of magnitude less than the number of transduced HSCs transplanted. These reports underscore the tremendous loss of long-term repopulating potential (LTRP) of HSCs with gene transfer/editing. Hence, failure of GT results from the poor understanding of the fundamental mechanisms of HSC loss and pathways which alter human HSC fate and their LTRP with genetic manipulation. If these are identified and targeted, HSCs can be maintained during genetic manipulation (with RV, LV or GE), exploiting the full therapeutic potential of GT.

Attempts to expand cord blood (CB) HSCs in vitro, a readily available source for HSCT, have largely failed[34,35]. Further, most of the test compounds—p38/MAPK inhibitors[36,37], angiopoietin-like proteins[38] prostaglandin E2 (PGE2)[39-42], Stemregenin-1 (SR1)[43-44], UM171[45] and UNC0638[46]—were found not to expand adult HSPCs. CB HSCs, besides being a largely irrelevant source for GT, are distinct from adult bone marrow (BM)- or mobilized peripheral blood (MPB)-derived HSCs. CB HSCs are either cycling, or more rapidly enter cell-cycle[47]. Adult HSCs, on the other hand, are largely quiescent, and protect their genome through quiescence[48]. Removing adult HSCs from their hypoxic BM-niche and manipulation of their genome after enforced cycling could induce HSC genotoxic stress signaling.

In this study, using an adult model of human HSCs, the mechanisms that affect the LTRP of quiescent and cycling HSCs with genetic manipulation were identified. Herein, HSC stress signaling and an excess activation of DNA damage response and repair (DDR) pathway was shown to result from viral vector integrase-/gene editing nuclease-induced DNA double strand break (DSB). Together, they alter HSC cell cycle kinetics to change HSC fate, resulting in loss of LTRP, and HSCs with a predominantly myeloid-biased progeny. Further, targeting these pathways was shown to restore genetically manipulated HSC fate and also to allow long-term maintenance of gene marking in both myeloid and lymphoid lineages. The findings have broad implications for the future success of GT using either viral vectors or gene edited human HSCs.

Results

Figure 2:
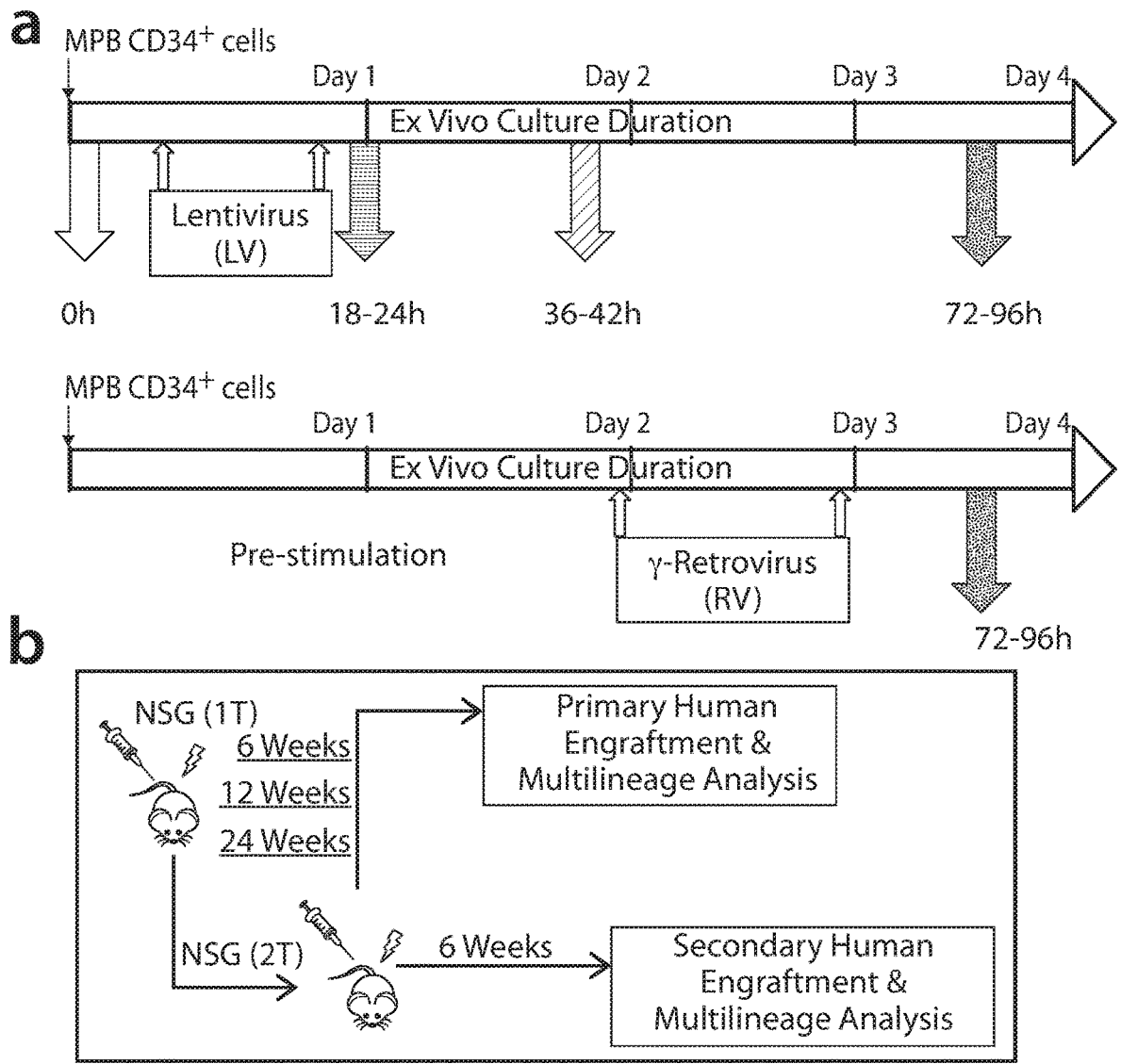
FIG. 2 shows a preclinical model for studying adult human HSC ex vivo manipulation and gene transfer and its effect on LTRP. Panel A: Freshly isolated or thawed mobilized peripheral blood (MPB) derived CD34$^+$ cells were utilized for the study. Two different protocols were utilized for the study where lentiviral vector (LV) or γ-Retroviral vector (RV) mediated gene transfer was performed at indicated time points. 0 h, 18-24 h, 36-42 h, and 72-96 h indicates the total amount of time where cells were exposed in the ex vivo culture after CD34$^+$ cell isolation before injection into NSG mice. Panel B: After indicated time in culture and transduction, 1 million CD34$^+$ starting equivalent cells were transplanted per NSG mouse after total body irradiation intravenously (primary transplant=1 T). Primary human engraftment and multi-lineage reconstitution was analyzed in mice at indicated time periods after bone marrow harvest at 6 and 12 weeks from left and right femurs, and after sacrifice at 24 weeks, from all bones. A portion of cells were analyzed for FACS and the rest were depleted of mouse CD45$^+$ cells and transplanted one to one, into secondary mice (secondary transplant=2 T).

Ex Vivo HSC Division and Gene Transfer Results in Loss of LTRP and a Myeloid Skewed Gene-Modified Progeny The NOD.Cg-Prkdcscid Il2rgtm1Wjl/SzJ (NSG) mouse xenograft model was first adapted to an adult (BM/MPB-derived) HSC model. One million MPB CD34$^+$ cells were transplanted in lethally irradiated NSG mice, and serial engraftment in bone marrow (BM) was assessed at 6, 12 and 24-weeks (circulating human cells do not correlate with engraftment in BM; FIG. 1, Panels A and B A multi-potential graft, composed of B-, T- and myeloid cells was only evident by 24-weeks (FIG. 1, Panels C and D), when 1:1 secondary transplants (2 T) yielded successful human secondary engraftment (>0.01% human CD45+cells). Multi-potential engraftment was assessed at 24-weeks in primary (1 T) mice, and LTRP at 1.5-3 months in 2 T mice (FIG. 2).

Two commonly clinically utilized protocols for LV and RV transductions were utilized. These protocols were specifically chosen to encompass viral vector-mediated gene transfer or gene editing (GE): The LV gene transfer is similar to that used for inducing non-homologous end joining (NHEJ)-mediated gene disruption by gene editing (GE) nucleases (zinc finger nucleases, homing endonucleases, TALENs or Cas9 nucleases), since both target HSC in a cell-cycle independent manner. RV gene transfer is similar to homology directed repair (HDR) to correct gene mutations by GE nucleases, as both require cycling HSCs. MPB CD34+ HSPCs were transduced with (a) GFP-LV within 18-24 h and either immediately transplanted, or kept in culture and transplanted at 36-42 h into irradiated NSG mice; (b) Alternatively, CD34+ cells were pre-stimulated for 2 days ex vivo, transduced with a GFP-RV at days 2 and 3 (44 h and 68 h), and transplanted into NSG mice between 72-96 h (FIG. 2, Panels A and B). As a control, NSG mice were transplanted with unmanipulated CD34+HSPCs immediately following their isolation (0 h) (FIG. 2).

Figure 3:
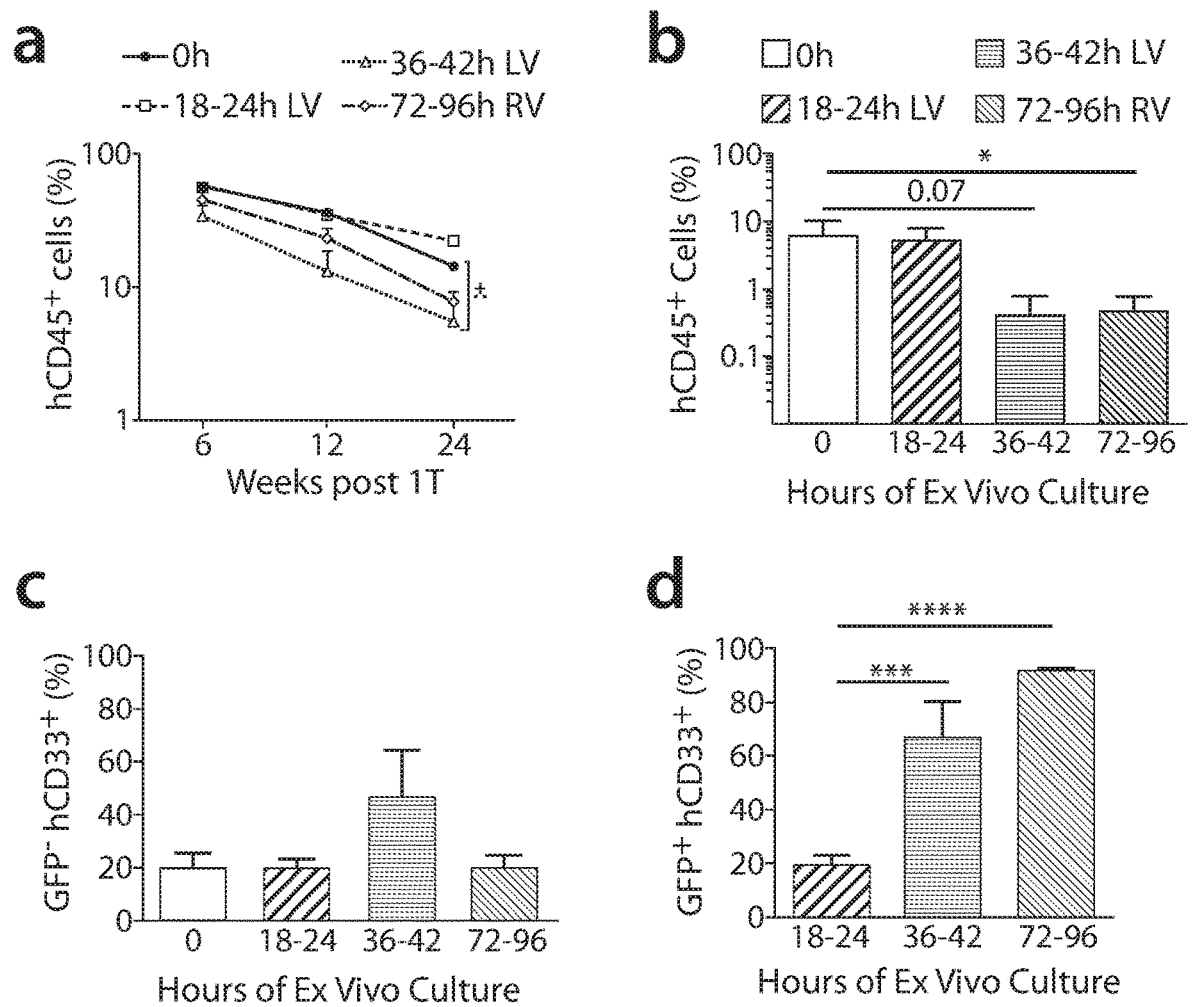
FIG. 3 shows ex vivo manipulation and gene transfer in human CD34$^+$ HSPC for longer than 24 hours results in significant loss of LTRP and a myeloid-skewed gene-modified progeny. Panel A: Freshly isolated or thawed human mobilized peripheral blood derived CD34$^+$ cells were cultured and transduced with lentiviral vector (LV) or γ-retroviral vector (RV) for the indicated time period. An input equivalent to 1 million CD34$^+$ cells was injected per irradiated NSG mouse. The percentage of human CD45$^+$ cells in bone marrow (BM) of primary NSG mice at the indicate time points is shown. The x-axis denotes the number of weeks after primary transplant (1 T). Data are representative of mean±SEM; for 0 h mock n=10, for 18-24 h n=20, for 36-42 h n=9, for 72-96 h n=19 mice for the total of 58 mice. Panel B: Total human cells in BM of primary NSG mice were transplanted one to one into irradiated secondary mice. Human engraftment in bone marrow (Y-axis) 6 weeks after secondary transplantation (2 T) is shown (for 0 h mock n=7, for 18-24 h n=5, for 36-42 h n=14, for 72-96 h n=14 for the total of 40 mice. Multi-lineage reconstitution was analyzed 24 weeks post 1 T. Both untransduced (GFP) and transduced (GFP$^+$) human CD33$^+$ myeloid population (Panels C and D), human CD19$^+$ B-Lymphoid (Panels E and F), human CD3+ T-Lymphoid (Panels G and H), & human CD34$^+$ HSPC population (Panels I and J) are shown. Data expressed as mean±SEM; n=same as FIG. 3, Panel A Statistics: Mann Whitney U test, ** P<0.0001, * P<0.001, **P<0.01, *P<0.05.
Figure 3:
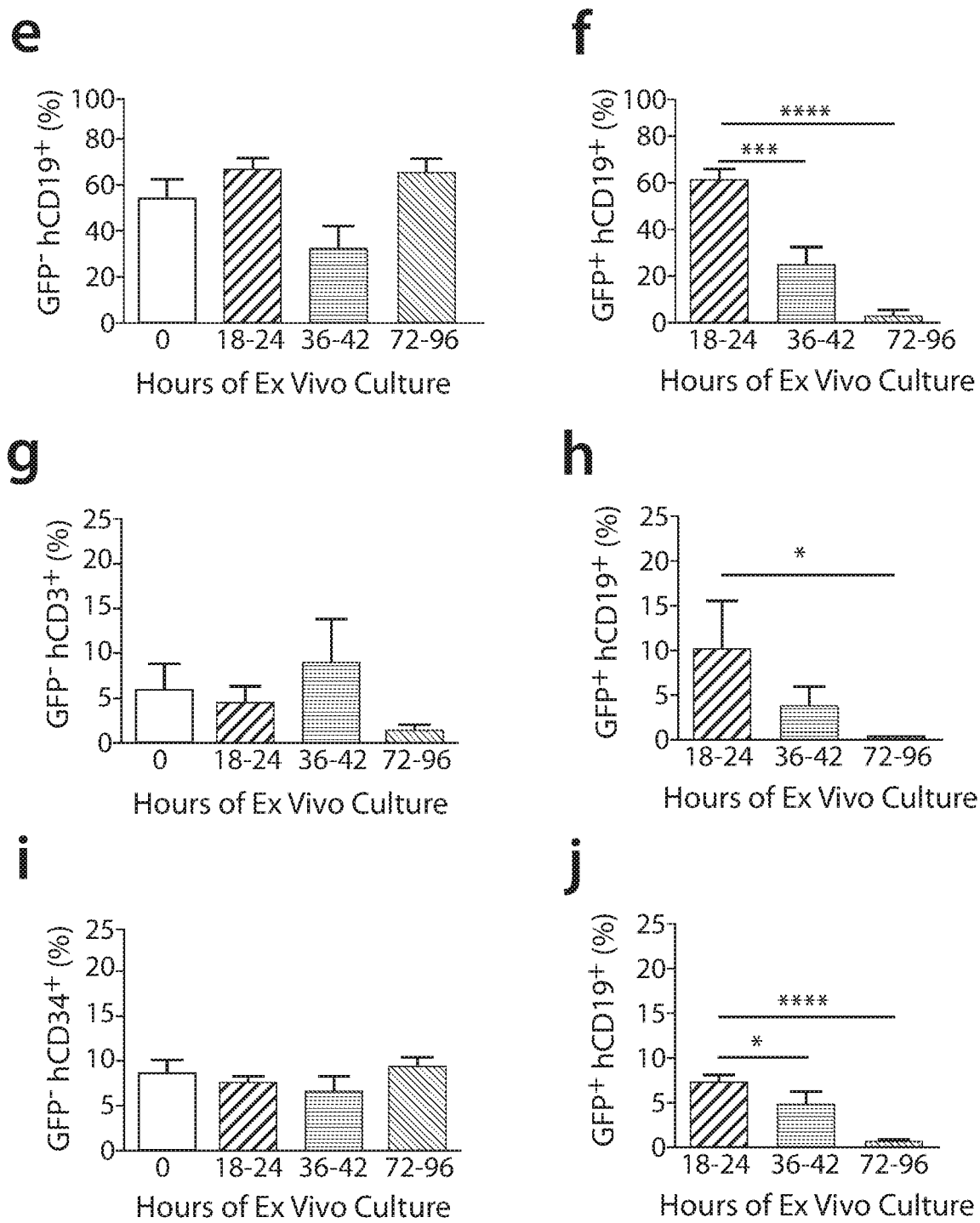
Figure 4:
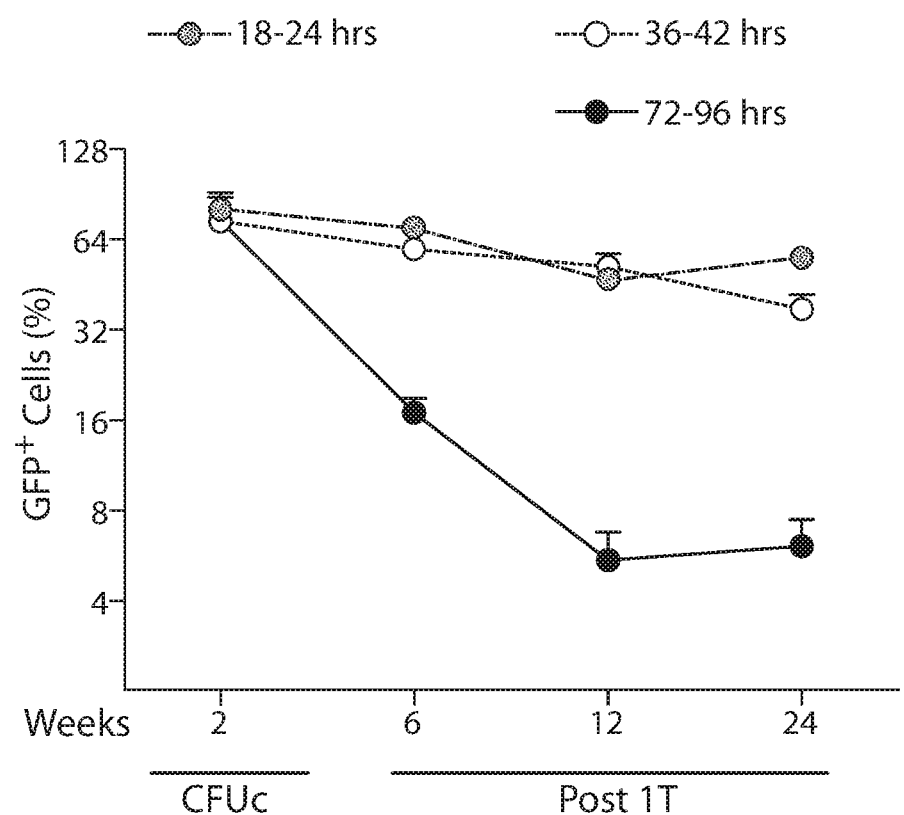
FIG. 4 shows GFP marking in vitro and in vivo. Human MPB CD34$^+$ cells were cultured and transduced with the LV or RV for the indicated hours (hrs) as described in FIG. 2, Panel A and colony forming unit cells (CFUc) plated on a small proportion of CD34$^+$ cells, while the rest (1 million starting equivalent) were transplanted intravenously into NSG mice. BM was aspirated at 6 and 12 weeks from right and left femurs, and mice sacrificed at 24 weeks; BM was analyzed for GFP$^+$ hCD45$^+$ cells at 6, 12 and 24 weeks (for 18-24 hrs n=20, for 36-42 hrs n=9, and for 72-96 hrs n=7 for the total of 36 mice; data presented as mean S.E.M).

Robust human hematopoietic engraftment (human CD45$^+$ cells) was observed in BM under all conditions with no major variations at 24 weeks after 1 T (FIG. 3, Panel A). However, there was a significant loss of LTRP in 2 T animals in conditions where HSPCs were cultured for greater than 24 h and the loss in LTRP was the highest in the RV 72-96 h group (FIG. 3, Panel B). Gene transfer efficiency in CD34$^+$ cells in vitro at 2 weeks (using the conventional colony forming assay) with RV and LV was comparable. While LV-transduced (GFP+) human cells declined from an average of 80% in vitro, to ~50% by 24-weeks in vivo, there was a higher progressive reduction in RV-transduced (GFP$^+$) cells from 80% in vitro to 5-8% in vivo (FIG. 4). Hence, RV-transduced human xenografts were largely lost with time in the NSG mice, while those transduced with LV vectors were better sustained.

Figure 5:
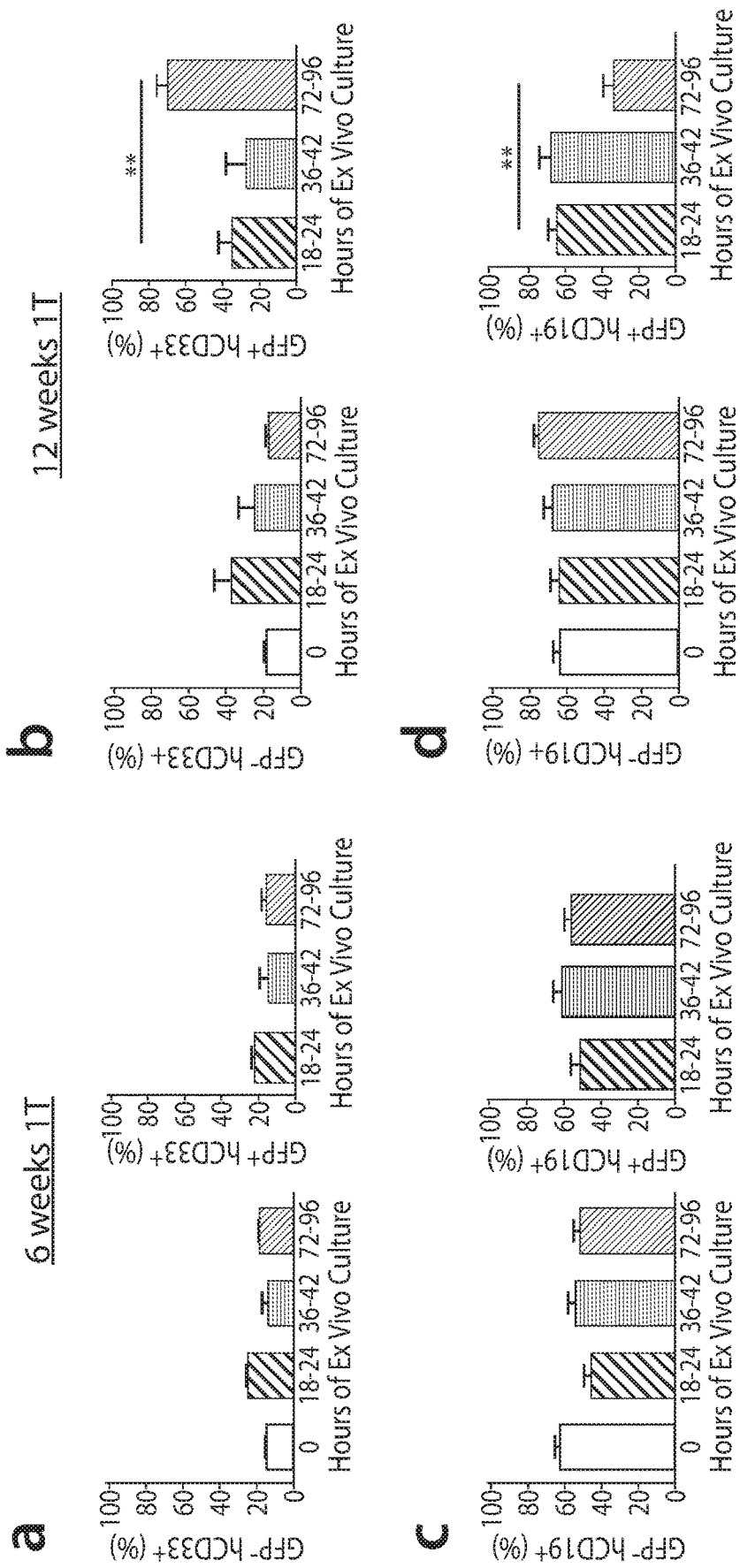
FIG. 5 shows multi-lineage engraftment of ex vivo manipulated and cultured MPB derived hCD34$^+$ cells in NSG mice. Human mobilized peripheral blood (MPB) CD34$^+$ cells were cultured for the indicated hours (X-axes), and transduced with lentiviral vector (LV) or γ-retroviral vector (RV) encoding enhanced green fluorescent protein (GFP) as a marker of transduced cells; an equivalent input of 1 million CD34$^+$ cells were injected per irradiated (280 cGy) NSG mouse thereafter. Bone marrow (BM) was analyzed for multi-lineage reconstitution at 6 weeks (Panels A, C, E and G) and 12 weeks (Panels B, D, F, and H) after primary transplant. Both untransduced (GFP$^-$) and transduced (GFP$^+$) human CD33$^+$ myeloid population (Panels A and B), human CD19$^+$ B-Lymphoid (Panels C and D), human CD3+T-Lymphoid (Panels E and F), and human CD34$^+$ HSPCs population (Panels G and H) are shown. Data expressed as mean±SEM. For 0 h n=12, 18-24 h n=7, 36-42 h n=11, 72-96 h n=20 for the total of 50 NSG mice. Statistics: Mann Whitney test, ** P<0.01.
Figure 5:
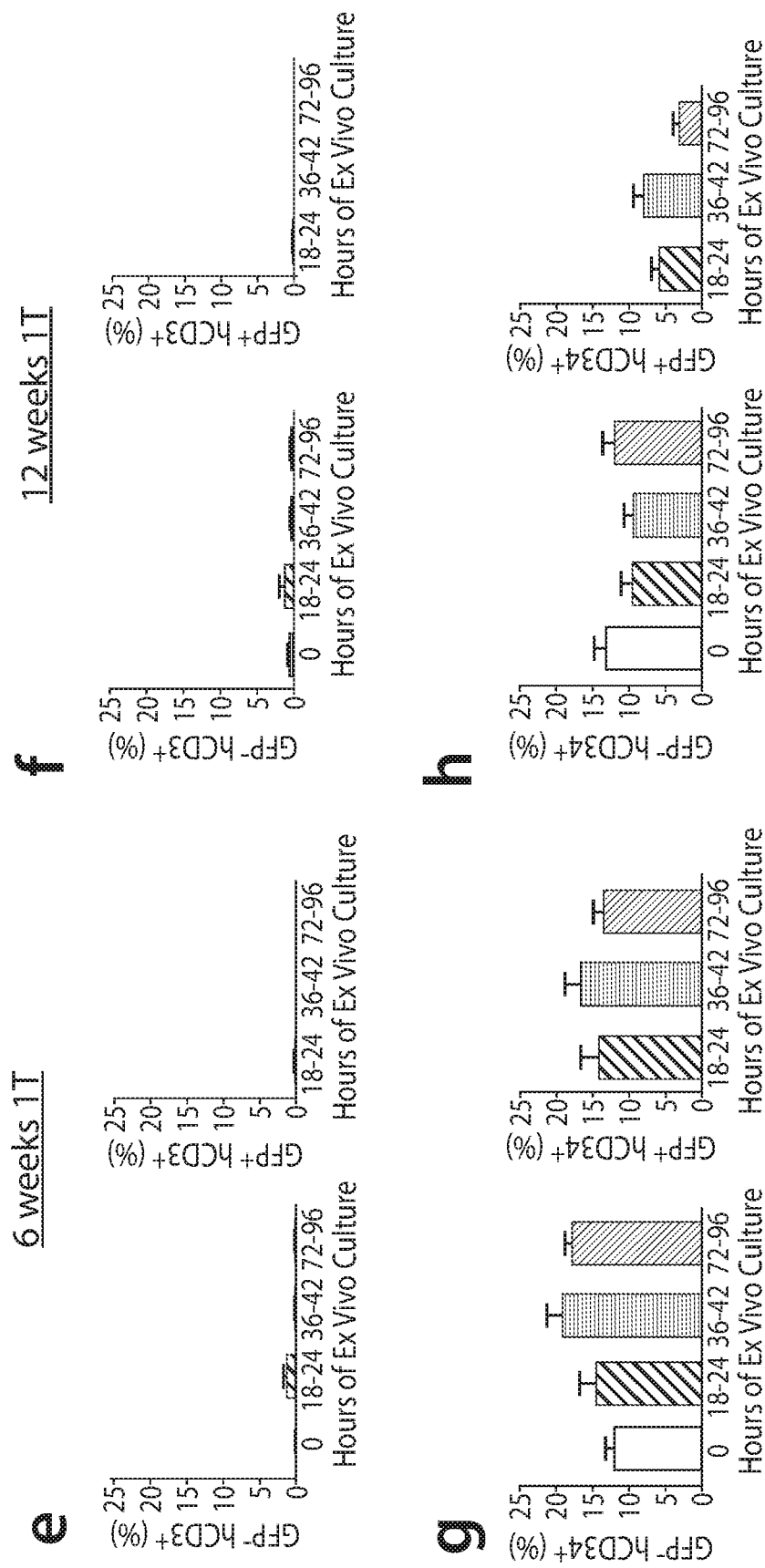

Multi-lineage reconstitution at 6, 12 and 24 weeks in BM in 1 T mice was examined in untransduced (GFP$^-$) and transduced (GFP$^+$) progeny of HSPC. At 6-weeks, lineage output was similar in both the GFP+ and GFP$^-$ populations and comparable to that derived from unmanipulated 0 h controls. However, by 12-weeks, the 72-96 h RV-gene modified population showed a significant increase in myeloid cell progeny, which occurred at the expense of reduced B lymphoid cell progeny (FIG. 5); and by 24 weeks, the myeloid bias was extreme in this group, but also apparent in the 36-42 h LV graft, which occurred at the expense of significantly reduced B and T lymphoid populations; there were also significantly less GFP$^+$ CD34$^+$ cells in both the 36-42 h LV and 72-96 h RV grafts (FIG. 3, Panels C-J). It was noteworthy that there was no such lineage skewing seen in the untransduced progeny in any of the conditions, indicating that this lineage skewing was not an effect of the cytokine/culture conditions; furthermore, the untransduced lineage pattern was similar to the graft derived from 0 h HSPCs. Hence, the myeloid lineage bias was secondary to gene transfer and increased time in culture. It is noteworthy that the self-inactivating RV used herein is devoid of viral enhancers and has not shown the insertional adverse events or lineage-skewing in experimental models[54,55] and human trials[56,57]. Similarly, the LV has also been tested in vitro and in human trials with no adverse events from vector insertion[31,58].

Collectively, gene transfer and ex-vivo culture beyond the first 24 h resulted in a significant loss of LTRP in 2 T mice, and the transduced CD34+ progeny was myeloid-biased, at the expense of the lymphoid progeny. The loss of LTRP mimic results of numerous RV GT trials and gene-edited xenografts[28,29], wherein there was either short-term engraftment (most unpublished,[59]) or modest gene-marked long-term engraftment, despite a high HSPC dose and robust gene transfer/HDR in vitro[21]. In addition, the model also simulates successful LV GT trials that have shown stable gene marking with a short culture protocol[30-33], but modest success/failure in other LV trials where LV transductions were performed similar to the RV protocol[60], collectively validating this model as a preclinical model of gene-manipulated HSC engraftment and LTRP.

Figure 6:
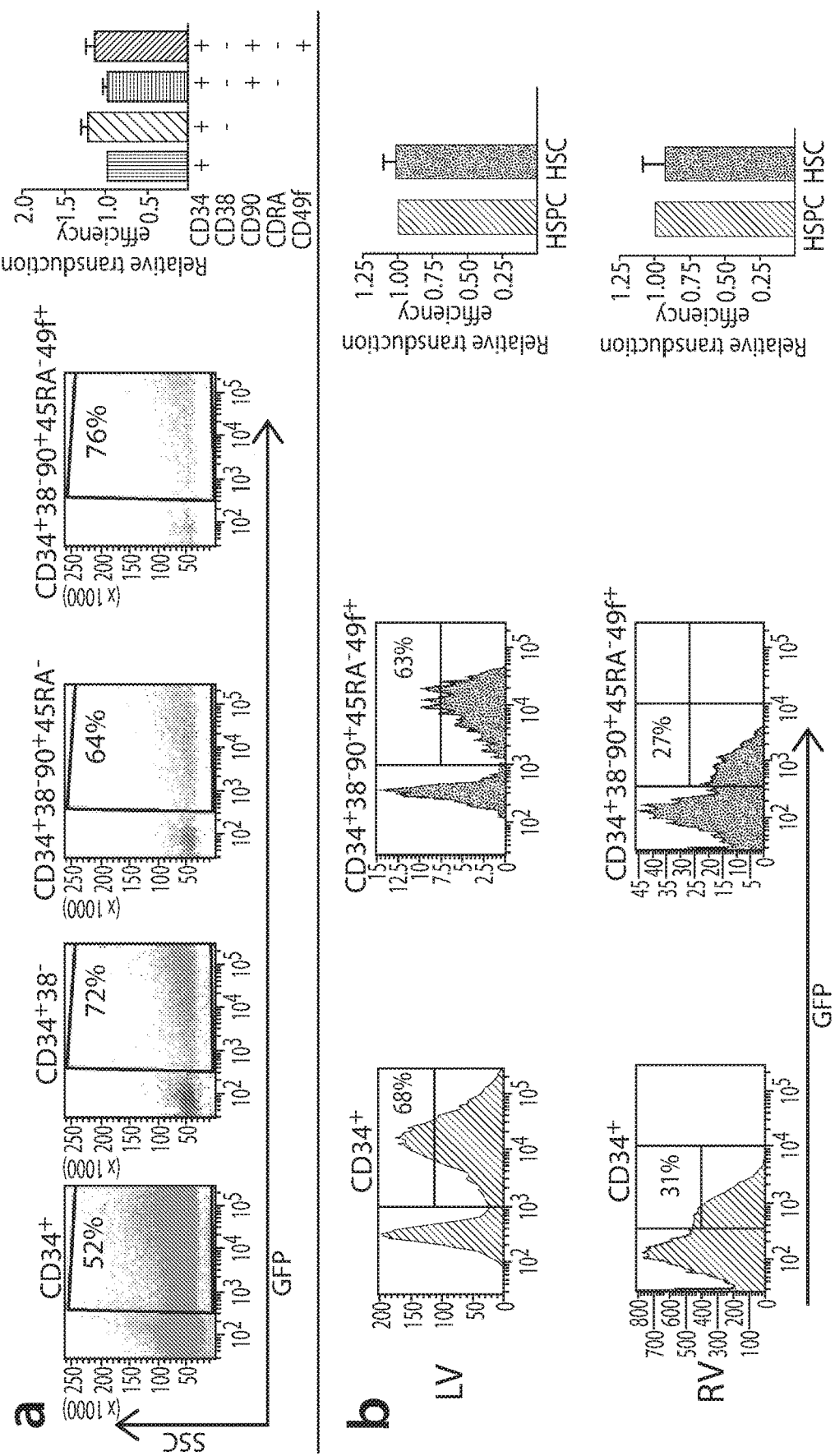
FIG. 6 shows that both LV and RV transduce human HPCs and HSCs comparably. Representative fluorescence-activated cell sorting (FACS) plot showing green fluorescent protein (GFP) marker expression in various hematopoietic stem/progenitor (HSPC) subsets after LV transduction for 42 hours (Panel A, left) and the quantification (Panel A, right) (n=4 independent experiments), in human CD34$^+$ HSPCs versus CD34$^+$38$^-$90$^+$45RA$^-$49f$^+$ HSCs post LV or RV transduction for 72 hours (left) and the quantification (right) (n=3 independent experiments) (Panel B) and in CD34$^+$38$^-$90$^-$45RA$^-$ MPP versus HSCs after LV (Panel C) or RV (Panel E) transduction for 72 hours along with the quantification of the respective groups (Panels D and F) are shown as a bar graph with mean±SEM (n=3 independent experiments).
Figure 6:
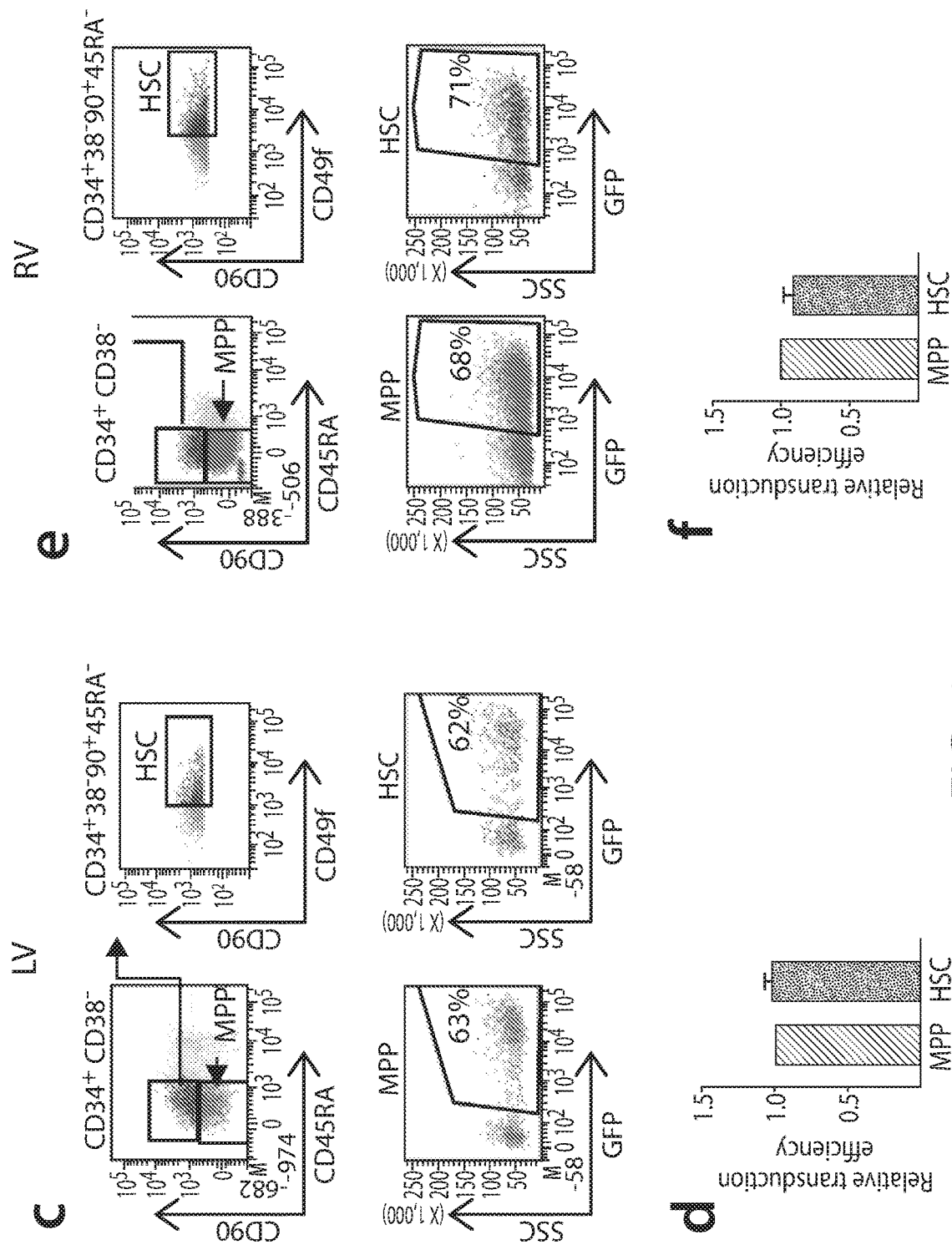

Mechanisms for the loss of LTRP and myeloid-lineage biased progeny were investigated. RV gene transfer and GE-mediated HDR occurs in dividing cells. LV gene transfer and GE-mediated NHEJ can occur independent of the cycling status of cells, although LV also have a preference for dividing cells[61]. It is possible that the failure of RV trials was from preferential integration of transgenes into HPCs or multipotent progenitors (MPPs), that readily cycle and comprise 99% of the CD34$^+$ HSPCs; and poor transduction of the quiescent HSCs, comprising ~1% of CD34$^+$ cells. Using the phenotype of human HSCs identified by Dick and colleagues[19], the clinical transduction conditions utilized herein were found to be indeed optimized to transduce human HSCs (CD34$^+$CD38$^-$CD90$^+$CD45RA$^-$CD49f$^+$), MPP (CD34$^+$ CD38$^-$CD90$^-$CD45RA$^{-19,62}$) and total CD34$^+$ cells comparably both with RV and LV (FIG. 6).

Figure 7:
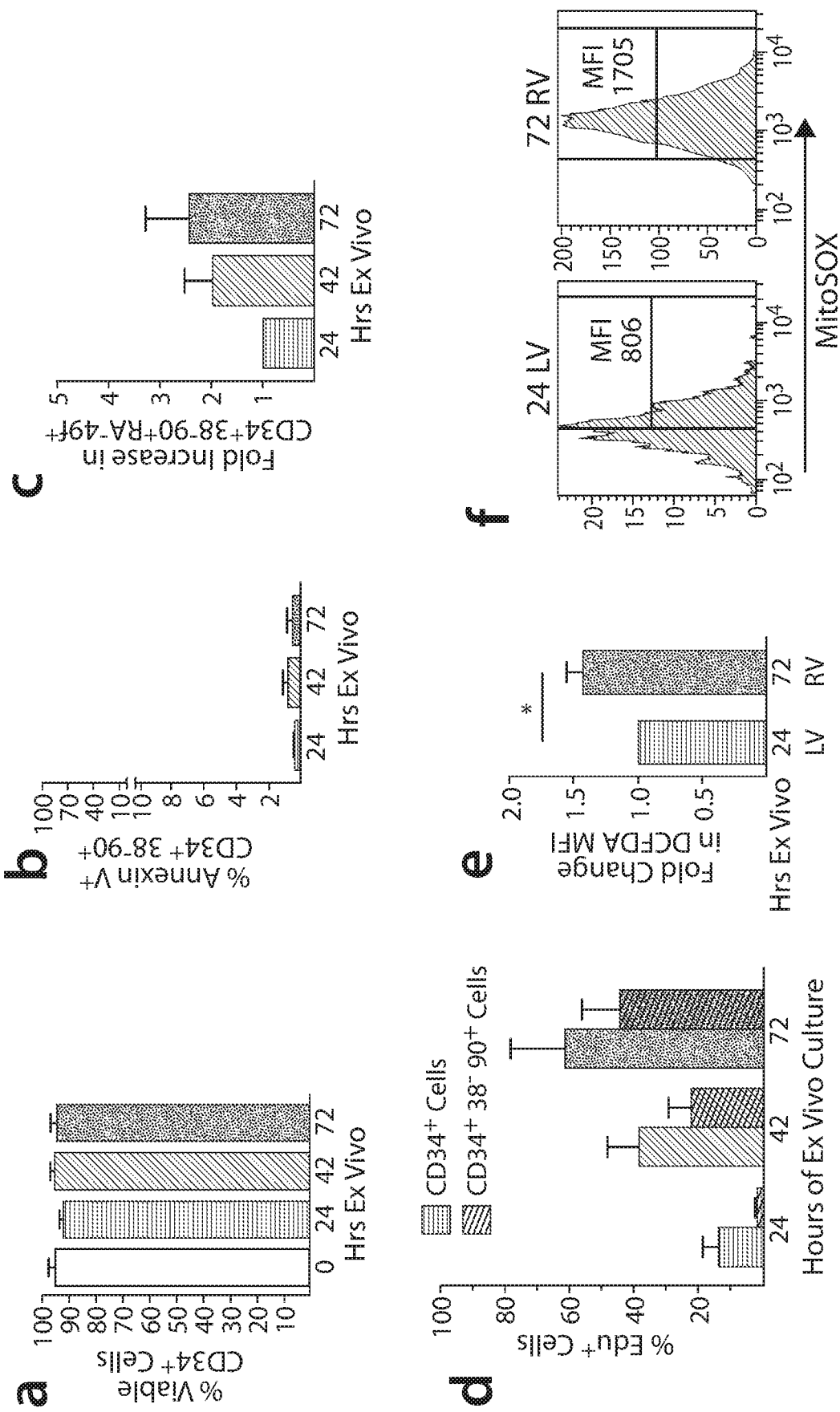
FIG. 7 shows that ex vivo manipulation is not associated with reduced viability or apoptosis of HSCs, but with increased phenotypic HSCs with higher ROS; reducing ROS decreases gene transfer. Human CD34$^+$ cells were cultured and transduced with LV or RV for the indicated time points. Panel A: Total cell viability after harvest was determined by trypan blue exclusion method. Panel B: Annexin V$^+$ (apoptotic) CD34$^+$38$^-$90$^+$ cells after ex vivo culture was detected by flow cytometry. Panel C: Fold increase in phenotypic human HSCs (CD34$^+$38$^-$90$^+$45RA$^-$49f$^+$ cells) was calculated after flow cytometric analysis (n=5). Statistics: paired t test. Panel D: Proliferation status of human CD34$^+$ HSPC versus CD34$^+$38$^-$90$^+$ HSC enriched population during ex vivo culture determined by the proportion of EdU$^+$ HSPCs and HSCs in the EdU incorporation assay (n=3). Panel E: Total intracellular ROS levels were determined using CM-H2DCFDA fluorescence; fold change in DCFDA MFI in LV and RV transduced human (CD34$^+$38$^-$90$^+$) HSCs is shown as mean of±SEM (n=3). Statistics: Student's t test, *p<0.05. Panel F: Representative histogram plots showing MITOSOX™ (Red Mitochondrial Superoxide Indicator) for the measurement of mitochondrial-specific ROS in human CD34$^+$38$^-$90$^+$ HSCs cultured for 24 hours versus 72 hours. The numbers represents MFI. Histogram plots showing MITOSOX™ (Red Mitochondrial Superoxide Indicator) levels (Panel G) and transduction efficiency in terms of % positive cerulean fluorescent protein (CFP) (Panel H) with increasing doses of the anti-oxidant N-acetylcysteine amide (NACA) in CD34$^+$38$^-$90$^+$ HSCs (n=1 experiment).
Figure 7:
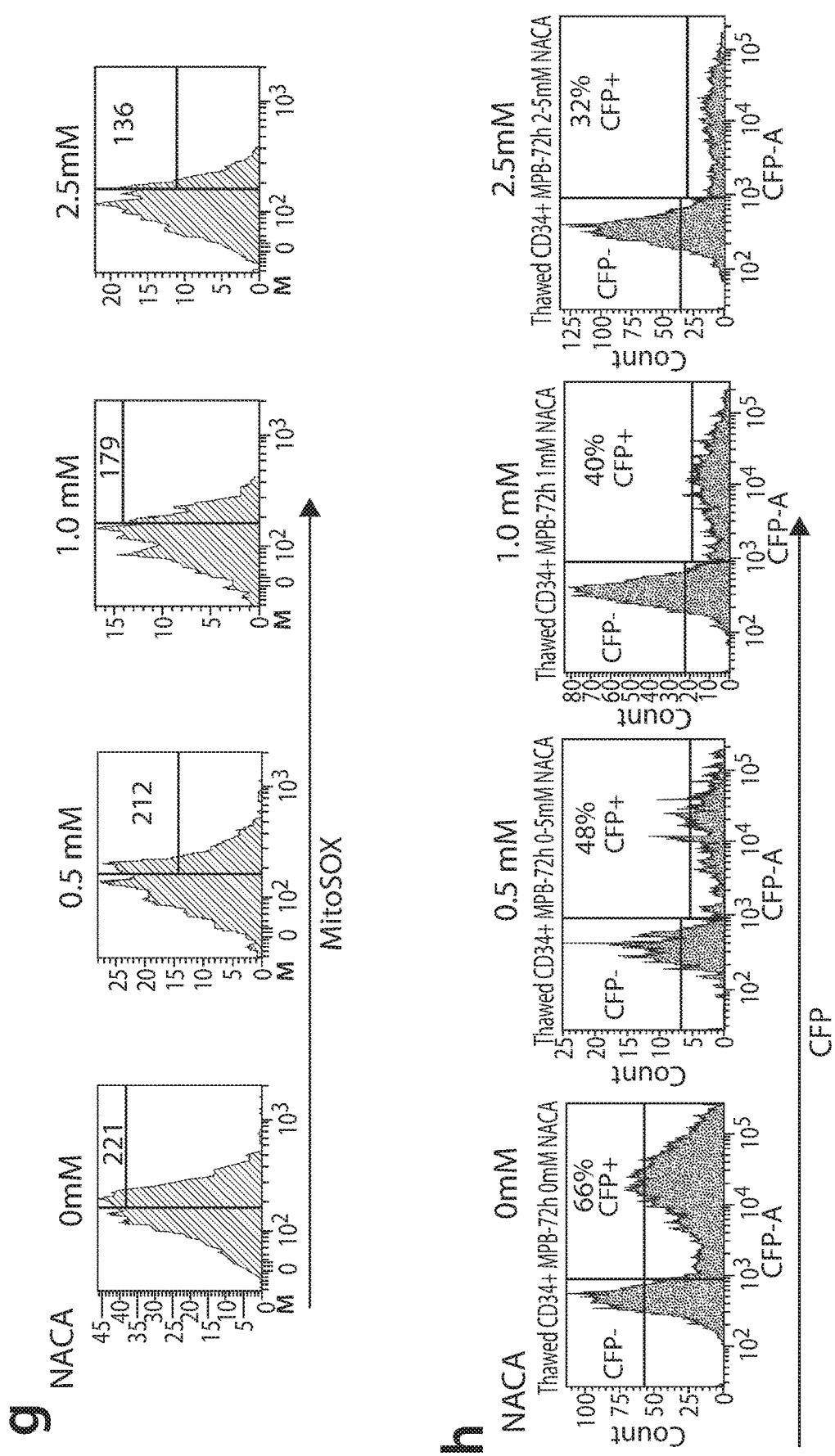

Hence HSC transduced, while cycling, likely change fate to HPC or are lost. A careful assessment of the HSPC compartment showed no cell death of CD34+ cells or apoptosis of the HSCs; in fact there was an increase in the phenotypic HSCs with increased time in culture (FIG. 7, Panels A-C). EdU labeling showed that the highly HSC-enriched CD34+38–90+ cells entered cell-cycle only after 24 h, and majority had undergone at least one cell division by 72 h (FIG. 7, Panels C and D).

It was next sought to determine if HSCs are physiologically maintained in their hypoxic niches[63], and if inducing cell division in cytokine-enriched culture in ambient oxygen conditions likely induces high oxidative stress[64]. Indeed, reactive oxygen species (ROS) were significantly increased in HSCs with 72-96 h of culture, and these ROS were generated from mitochondria (FIG. 7, Panels E and F). N-acetylcysteineamide was able to decrease ROS in the HSCs, but unexpectedly, resulted in a reciprocal decline in gene transfer efficiency (FIG. 7, Panels G and H). Therefore, the downstream pathways activated by increased oxidative stress were next investigated.

Figure 8:
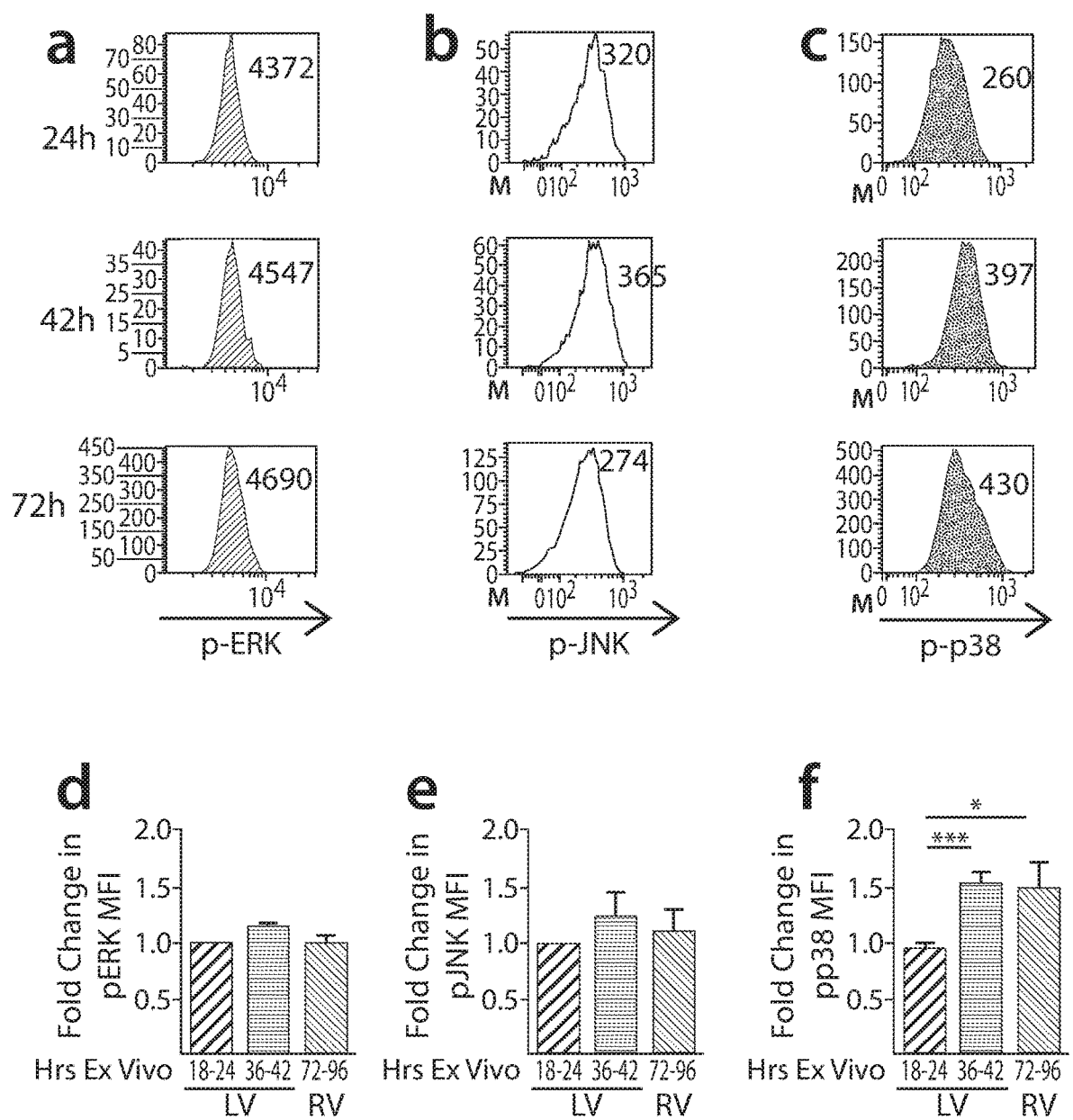
FIG. 8 shows that an increase in time in culture activates p38 MAPK in HSC. Human MPB derived CD34$^+$ cells were cultured and transduced as described in FIG. 4. Representative histograms plots showing phospho-ERK (p-ERK) (Panel A), phospho JNK (p-JNK) (Panel B), and phospho-p38MAPK (p-p38) (Panel C) levels in human (CD34$^+$38$^-$90$^+$) HSC-enriched by flow cytometry. Quantitative fold-change in mean fluorescent intensity (MFI) of p-ERK (Panel D), p-JNK (Panel E) and p-p38 (Panel F) in HSCs at indicated times are shown. Data expressed as mean±SEM from 3 independent experiments using three different MPB donors. Statistics: Student's t test, *p<0.05, p<0.01, *p<0.001. Panel G: Representative histogram plot of p-p38 level in non-cycling (in $G_0$-$G_1$ phase of cell cycle) HSCs versus cycling (in S-$G_2$-M phase of cell cycle) HSCs. Hoechst was used to determine cycle phase. Numbers indicate MFI. Quantitative fold-change in p-p38 MFI in cycling vs non-cycling (Panel H) and untransduced (GFP$^-$) versus transduced (GFP$^+$) HSCs (Panel I) from 3 independent experiments is shown as mean±SEM. Statistics: Student's t test, *p<0.05. Panels J and K: Human MPB derived CD34$^+$ cells were cultured with or without various p38 inhibitors (B=Birb 796, Vx=VX 745, and Ly=Ly2228820) and transduced with retrovirus (RV) for 72 hours. Representative histogram plots of p-p38 levels in human (CD34$^+$38$^-$90$^+$) HSCs are shown (Panel J). Quantitative fold change in p-p38 mean fluorescence intensity (MFI) in 72 h cultured human HSCs compared to unmanipulated (0 h) HSCs is shown (Panel K). Data is expressed as mean±SEM from 7 independent experiments using 7 different MPB donors. Statistics: Student's t test, *p<0.05, p<0.01, *p<0.001.
Figure 8:
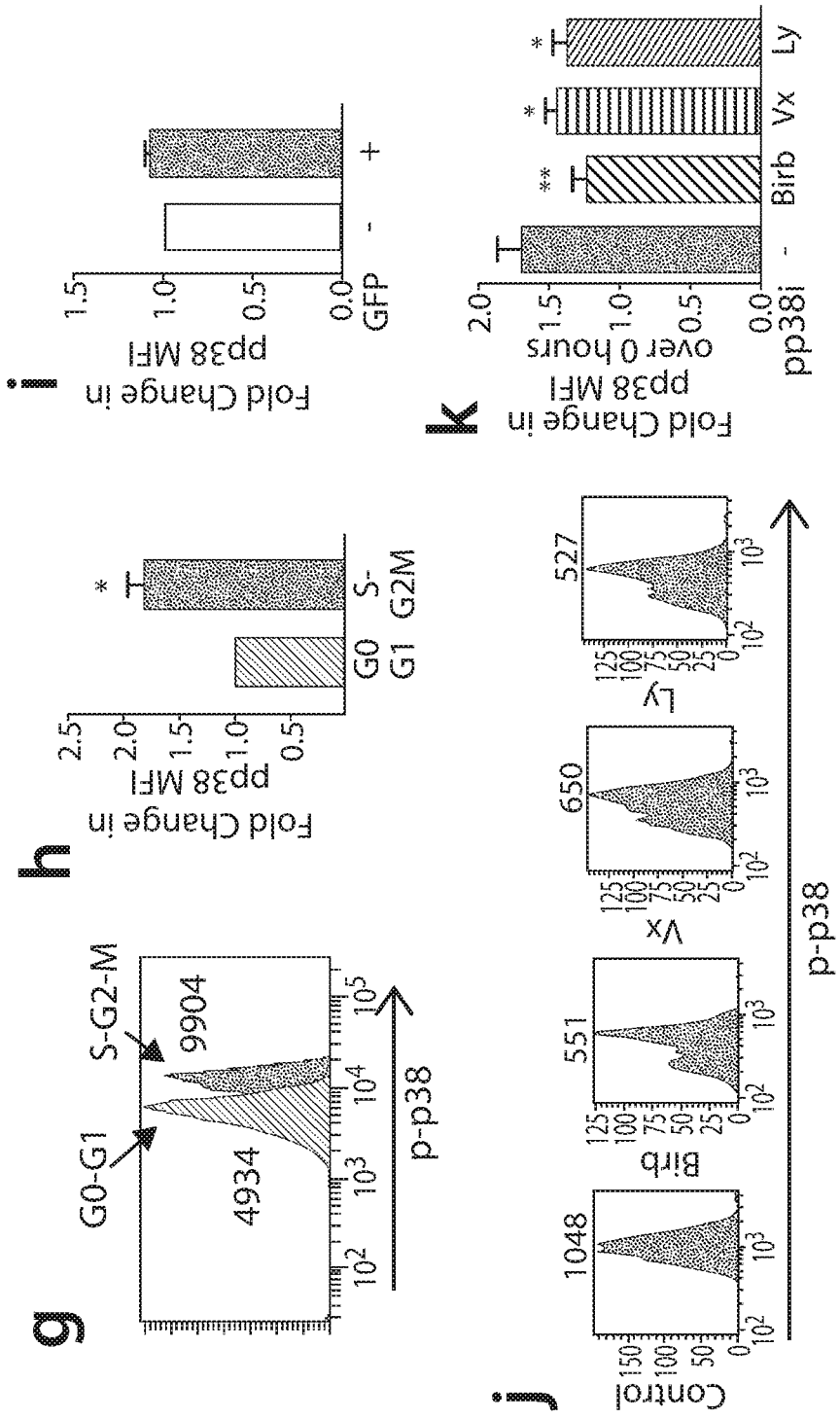

High ROS has been shown to induce stress signaling, especially mitogen-activated protein kinases (MAPKs)[37]. The phosphorylation status of ERK, JNK and p38 MAPKs were analyzed in the different culture protocols and significant activation only of p38 MAPK (p38) with ex vivo culture beyond 24 h was found (FIG. 8, Panels A-F). Interestingly, there was significantly higher p38 activation in cycling HSCs, although not in transduced HSCs (FIG. 8, Panels G-I). All p38 inhibitors (p38i)[65][66] decreased p38 phosphorylation in HSCs, showing specificity of activation of this pathway (FIG. 8, Panels J and K). A previous report has shown that CB CD34+ cells cultured for a week with p38 inhibition have increased human engraftment at 4 months in xenografts[36]. This time-point may still reflect HPC output. Hence, the effect of p38 inhibition on LTRP of adult gene-modified HSCs was explored.

Figure 9:
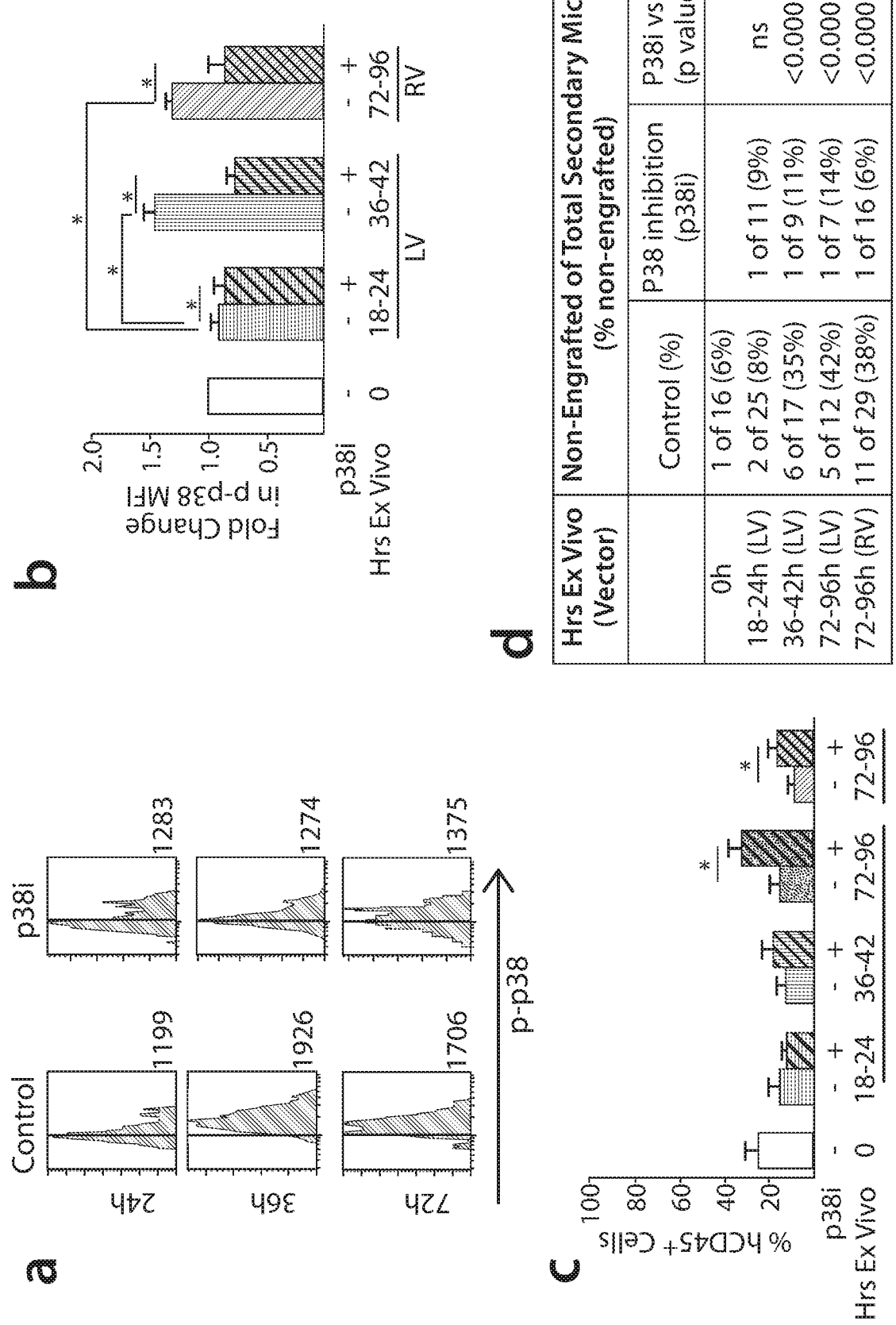
FIG. 9 shows that inhibition of p38 MAPK during ex vivo culture rescues the long term repopulating potential (LTRP) of HSCs and partially reverts the myeloid skewing phenotype. Human CD34$^+$ cells were cultured and transduced with lentiviral vector (LV) or γ-retroviral vector (RV) expressing green fluorescent protein (GFP) for the indicated time points. Representative flow cytometric histogram plot of p-p38 MAPK mean fluorescence intensity (MFI) in CD34$^+$38$^-$90$^+$45RA$^-$49f$^+$ HSCs with or without p38 inhibitor (p38i) (Panel A), and quantitative fold change of p-p38
Figure 9:
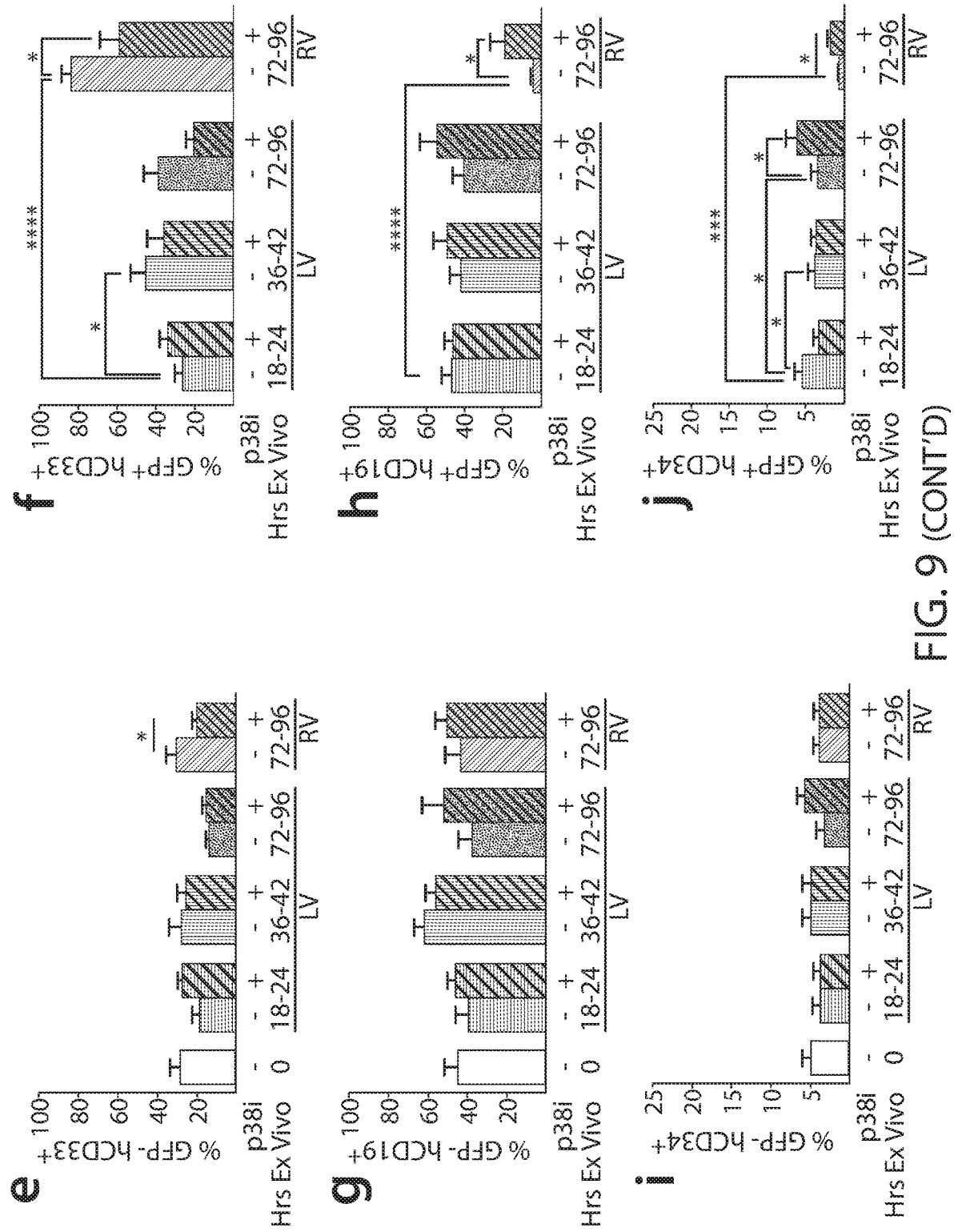

Birb-796, a selective p38α inhibitor[67], was chosen at concentrations far below those causing non-specific inhibition; and significantly lower phospho-p38 (p-p38) was observed, at levels seen in unmanipulated HSCs in all conditions (FIG. 9, Panels A and B). To distinguish the effect of gene transfer into non-cycling HSCs versus cycling HSCs, from the effect of culture duration, serial transplants of human CD34+ HSPCs transduced with LV within 18-24 h (non-cycling HSCs) and transplanted after 24, 36-42 or 72-96 h, or transduced with RV at 44 h and 68 h (cycling HSCs) and transplanted at 72-96 h (FIG. 2) were performed, with or without the p38i. At 24 weeks, human CD45+ cell engraftment in the NSG BM was similar among all the groups with/without p38i, and indeed improved with p38i for the 72-96 h LV and RV groups (FIG. 9, Panel C), similar to results reported in CB CD34+ cells[36].

Interestingly, p38i restored the LTRP in 2 T mice transplanted with 36-42 h and 72-96 h groups to the levels observed in 0 h and 24 h groups (FIG. 9, Panel D and FIG. 10): nearly one-third 2 T mice did not engraft when CD34+ cells were cultured for longer than 24 h without p38i; but addition of a p38i restored the LTRP in 2 T mice to levels seen with unmanipulated HSPCs, regardless of vector type or when they were transduced, suggesting that loss of LTRP occurs with the first HSC division in vitro.

p38i also restored the multi-potentiality of the graft at 24 week (1 T) to levels similar to 0 h controls, if gene transfer into HSCs occurred in the first 24 h (when not in cycle) of culture, even if they were kept in prolonged cultures up to 96 h thereafter, and then transplanted. However, when cycling HSCs were transduced (the RV group), the pronounced myeloid skewing of the transduced progeny was somewhat reduced, but still quite significant, (FIG. 9, Panels E and F), with a corresponding reduction in B cells (FIG. 9, Panels G and H) and CD34+ HSPCs (FIG. 9, Panels I and J). This effect was specific only to genetically manipulated HSC progeny (FIG. 9, Panels E-J). Taken together, p38i during gene transfer maintained transduced HSC LTRP during prolonged ex vivo culture conditions, but the extreme myeloid biased progeny and reduced lymphoid potential with transduction of cycling HSCs was only partly rescued.

Mechanism of Action of p38 Inhibition on Human HSC Fate

Next, the mechanism by which p38 inhibition can retain the LTRP of cultured and transduced HSCs was investigated. p38i had no effect on the total number of CD34+ cells, or viability in vitro and also no effect on gene transfer efficiency in vitro or in vivo (FIG. 11, Panels A-C). The HSC compartment also showed no difference in apoptosis, transduction efficiency, or ROS levels with p38 inhibition; and the increased phenotypic HSC population was similar, with or without p38i, except in prolonged cultures, when phenotypic HSCs were higher with p38i (FIG. 12).

RV/LV integrase[8,68] or GE nuclease mediated DNA double-strand break (DSB) could evoke DNA damage response and repair (DDR) pathways. Therefore, whether p38 inhibition reduces the DDR with HSC division and gene transfer was examined in FACS-sorted HSC by immunofluorescence. Indeed, increased γH2AX foci/cell were seen in transduced HSCs in either the 42 h or 72 h group; which were highly significantly reduced with p38 inhibition (FIG. 13, Panels A-C); 53bp1 staining, concurrently performed, ensured that increased γH2AX was associated with DDR foci (FIG. 13, Panels A-C).

The DDR pathway activation was also compared in transduced and untransduced HSCs by flow cytometry for γH2AX. As compared to unmanipulated HSCs (0 h), increased γH2AX MFI and increased number of γH2AX positive HSC were seen even at 24 h (a period where HSC are not in cycle), which returned to levels seen in unmanipulated HSCs with p38i treatment (FIG. 13, Panels D-F). Notably, this population is transduced, although GFP protein expression is not present at this early 24 h time point. Hence, increased DDR at 24 h is likely caused by the gene transfer induced DSB. After 36 hours, the untransduced (GFP−) versus transduced (GFP+) HSC population could be separately analyzed. The transduced (GFP+) population had higher γH2AX levels, and percentage of γH2AX positive HSCs than the untransduced (GFP−) population, both in the 36-42 h and 72-96 h group; p38i significantly reduced the percentage of γH2AX+ cells, although at these later time points, the levels of γH2AX did not return to levels seen in 0 h HSCs [both the percentage of HSCs that stain for γH2AX (FIG. 13, Panels D-F) and the γH2AX MFI (FIG. 13, panels D and E)]. Inducing dormant HSCs to cycle also triggers DDR[69]. The data show that p38 inhibition significantly reduces the DDR in HSCs both with increased cycling, and with transduction, although not to baseline levels seen in unmanipulated HSC.

p38 activation was highest in cycling HSCs (FIG. 7, Panel D, and FIG. 8, Panels G and H). Therefore, the role of p38i on HSC cell-cycle kinetics was examined. Nearly all HSCs were in $G_0$ phase when freshly isolated from MPB (FIG. 14, Panel A) or BM (FIG. 15); by 24 hours, a third of them transitioned to the $G_1$ phase, but most HSCs were not cycling (not in S-$G_2$M phase). p38i significantly increased the proportion of HSCs in the $G_0$ quiescent phase, and decreased the proportion of HSCs in the S-$G_2$M phase before the first HSC division in vitro (24 h). However, after HSCs progressed through cell cycle, the effect of p38i on increasing the $G_0$ population was lost (FIG. 14, Panels A and B). Therefore, when the transduction/DSB occurs when HSC are not in cycle, the p38i-mediated delay in transition from $G_0$ to $G_1$ and $G_1$ to S phase (FIG. 14, Panels A and B and FIG. 16), can allow the DDR to subside; hence HSC fate is maintained, as shown by rescue of LTRP and a balanced lineage production. The same phenomenon was also seen in HSCs derived from adult human bone marrow (FIG. 15). Significantly lower GFP+ HSCs in $G_0$ phase at 42 h were also noted, even though they were transduced within 24 h, indicating that LV preferably transduced $G_0$ cells that were not deeply dormant, and by 42 h, these had progressed to $G_1$ and S-$G_2$M phase. However, when HSCs were transduced when they were actively cycling, as with RV, there was no difference in the percentage of cells in the different phases of cell cycle, with or without p38i (FIG. 14, Panels A and B, and FIG. 16).

Another remarkable finding was that only the transduced (GFP+) 72 h RV HSC population showed a highly significant reduction in HSC in $G_1$ phase and increase in those in S-$G_2$M phase, regardless of p38 inhibition. Since in this condition, the transplanted HSCs produced a myeloid-biased progeny that p38i did not significantly rescue, the S-$G_2$M phase was examined (FIG. 9).

Crosstalk Between S-$G_2$M Checkpoint and HIF-1α Links RV-Induced DSB, Cell Cycle and HSC Fate The S-$G_2$M kinetics of transduced and untransduced non-cycling and cycling HSCs showed that when DSB occurred in cycling HSCs (RV transduction after 2 days of culture) there was accumulation of HSCs in the late S and $G_2$M phases (FIG. 14, Panel C). However, when vector integration occurred within the first 24 h (with LV), this phenomenon was not seen (FIG. 14, Panel D). Furthermore, this effect was not specific to RV, but specific to the cell-cycle phase of the HSCs when transduced. CD34+ cells from the same donor were cultured for ~2 days (44 h) and transduced at 44 h and 68 h either with LV (LV late or $LV^L$), or with RV, or HSCs were transduced with LV within 24 h but kept in culture for 72 h ($LV^E$) (FIG. 17, Panel A). The late S and $G_2$M accumulation was observed only in transduced (GFP+) cycling HSCs in the $LV^L$ or RV groups (FIG. 14, Panels E and F). The $G_2$M accumulation was lesser in the $LV^L$ than RV, since LV transduces both cycling and non-cycling HSC, and therefore the GFP+ population comprised of a mixed population. Notably, this $G_2$M accumulation did not result in apoptosis (rather, HSC numbers were increased, FIG. 7, Panel C and FIG. 12, Panel C), and HSCs transitioned out of the $G_2$M phase when followed serially (FIG. 14, Panel E). This $G_2$M accumulation was not seen when non-cycling HSCs were transduced (24 h LV or $LV^E$; FIG. 14, Panel E), even when cell cycle analysis was performed at the same time points after transduction with $LV^E$ versus RV (FIG. 14, Panels C and D).

The increase in phenotypic HSCs, which fail at maintaining LTRP and produce a myeloid biased progeny, is reminiscent of aged/exhausted HSCs. The HSC population was sorted after LV and RV at 24 h and 72 h, respectively, from one experiment for RNAseq analysis, to get an overview of the transcriptional profile of aging-related genes. Wnt5a and Wnt4 (non-canonical Wnt genes associated with aging of mouse HSC[70-71]) mRNA levels were undetectable in the human CD34+38−90+ RA-49f HSC, and only Wnt5b, Wnt11, and Fzd3 (a downstream target of Wnt signaling[72]) expression was at detectable levels. A qRTPCR for these genes in 24 h $LV^E$ and 72 h $LV^L$ sorted HSCs from different MPB donors, using P34 (Cdk2) mRNA expression to validate the non-cycling and cycling phases of HSCs at these time points, showed increased Fzd3 and Wnt family genes in the $LV^L$ group (FIG. 17, Panel B).

To further validate that this phenomenon is not vector induced, but occurs from any induced DSB in cycling HSCs, it was determined if this $G_2$M accumulation would also occur with a gene editing nuclease. To this end, an experiment was performed where CD34+ cells were cultured for the same 44 h period as $LV^L$ and RV groups, and then nucleoporated with a Cas9/hCD45gRNA ribonucleoprotein complex, that would induce a rapid DNA DSB in the human CD45 alleles; controls cells were nucleoporated with vehicle, without the Cas9/gRNA ribonucleoprotein complex. The $G_2$M accumulation was observed in the HSC population subjected to Cas9 nuclease-induced DSB (shown by loss of CD45 expression by FACS in HSCs; FIG. 17, Panels E and F).

Functionally, this delay of HSC in the $G_2$M phase changes HSC lineage fate, resulting in a myeloid biased progeny: the 24 h LV and 72 h $LV^E$ groups at 6 months post-1 T showed no myeloid biased, but 72 h $LV^L$ or RV groups had a myeloid-biased transduced HSC progeny at the expense of loss of B-lymphoid potential (FIG. 17, Panels C and D). Collectively, the data shows that when a DSB is induced in cycling HSCs via vector integration or a nuclease, the DDR stalls the HSC in the $G_2$M phase, and this delay results in HSC that primarily produce a myeloid progeny; this along with a concomitant increased number of HSC with increased expression of Fzd3 and Wnt5b suggests a HSC phenotype associated with exhaustion or aging[71]; alternatively, it is also contemplated that the lymphoid biased HSC population may be more vulnerable[73] with accumulation in $G_2$M phases.

Mechanisms of $G_2$M accumulation were sought, since their identification and targeting could restore normal cell-cycle progression in the HSCs transduced when cycling. Genetic manipulation of cycling HSC is essential for HDR-mediated gene editing, since few human diseases can be corrected with NHEJ-mediated gene disruption. DNA DSB classically triggers the cell cycle check point, ATM/Chk2 kinase, but if DSB occurs in S and $G_2$ phase, it can trigger ATR/Chk1 kinase[74-77]. More recently, activation of MK2/p38 MAPK by DNA DSBs during V(D)J recombination in thymocytes has been shown to induce a $G_2$M cell-cycle checkpoint[78]; and besides the canonical ATR/Chk1 and ATM/Chk2 kinases, MK2/p38 MAPK has recently been shown to be the non-canonical check-point kinase that controls the cell-cycle response to DNA damage in parallel to Chk1[79]. A specific Chk1 inhibitor (MK-8776; Chk1i), a Chk2 inhibitor (PV1019; chk2i) and p38i alone or in combination with Chk1i or Chk2i were used to determine their role in HSCs accumulated in $G_2$M phase. Fewer transduced-HSCs were found to accumulate in the $G_2$M phase with Chk1i (albeit not statistically significant), but not with Chk2i (FIG. 18, Panel A and FIG. 19, Panel A). However, remarkably fewer transduced-HSCs accumulated in $G_2$M phase with the combination of Chk1i and p38i, but not Chk2i and p38i, indicating that Chk1 kinase and p38 MAPK together induce the $G_2$M checkpoint when the DSB is induced in cycling HSCs (FIG. 19, Panel B). Furthermore, Chk1 did not reduce γH2AX levels in the transduced HSCs, which required p38i; and the combination of Chk1i and p38i did not have any additive effect in reducing γH2AX (FIG. 19, Panel B). Inhibition of a cell cycle checkpoint in HSCs can allow other DSBs that occur to go unchecked. Hence, alternatives to Chk1i were explored.

HIF-1α deficient mice develop an aged HSC phenotype[80]. It was hypothesized that delay in cell-cycle progression in HSCs could result in destabilization of HIF-1α, mediating the transduced HSC phenotype; and loss of HIF-1α could further activate Chk1, since HIF-1α deficient mouse embryonic fibroblasts show increased Chk1 expression[81]. Indeed, a significant decrease in HIF-1α levels by immunofluorescence was observed, when the HSCs were merely cultured for 72 hours and HIF-1α levels were further reduced in HSCs that were transduced when cycling (72 h) as compared to 0 h HSCs (FIG. 19, Panel D). Prostaglandin E2 (PGE2) has been reported to enhance HSC survival and homing in murine and CB HSCs[42][52][82] by stabilizing HIF-1α in HSCs[82]. Herein, it was investigated if PGE2 would stabilize HIF-1a in cycling, transduced, adult HSCs, and whether this stabilization would prevent $G_2M$ accumulation and restore the HSC lineage fate. Immunofluorescence analysis for HIF-1α in sorted highly HSC-enriched CD34$^+$38$^-$90$^+$ cells demonstrated that HIF-1α was significantly reduced by RV induced DNA DSB in cycling HSC, and it could be stabilized with PGE2, albeit, the highest HIF-1α levels were seen when PGE2 was combined with p38i (FIG. 19, Panels C-E). The immunofluorescence data was confirmed with flow cytometry (FIG. 18, Panel B). Furthermore, increased HIF-1α in transduced cycling HSCs was associated with their reduced accumulation in the $G_2M$ phase of cell cycle. Importantly, PGE2 alone tended to reduce the number of cycling transduced CD34$^+$38$^-$90$^+$ cells in $G_2M$ phase, but a significant reduction in $G_2M$ accumulation only occurred with the combination of PGE2 and p38i. Notably though, PGE2 alone had no effect on reducing the DDR (reducing γH2AX levels) in these HSC-enriched populations. However, p38i significantly reduced the γH2AX as described above, and the combination of p38i and PGE2 resulted in a highly significant reduction of γH2AX (FIG. 19, Panel G and FIG. 18, panel C) and $G_2M$ accumulation, indicating both are essential for LTRP and lineage fate retention of HSC.

p38i Combined with PGE2 Restore LTRP and Lineage Fate of Transduced HSCs.

Next, a limiting dilution transplant with the combination treatment of p38i and/or PGE2 in NSG mice was performed. CD34$^+$ cells were cultured overnight and then transduced with LV 12 h apart (at 18 and 30 h), for a total culture period of 42 hours, and transplanted into NSG mice with limiting doses of CD34$^+$ cells, starting with half the dose (500K CD34+/mouse) used in prior experiments. Myeloid skewing and loss of B-lymphoid potential was observed at 6 mo in the 500K and 250K cell groups, similar to RV transduced cells (FIG. 20, Panels A-D). Remarkably, at further limiting HSC doses, which impose severe regenerative stress on engrafted HSC, a myeloid skewing was observed and loss of B lymphoid potential even in the untransduced CD34$^+$ cells, indicating that excessive HSC proliferation induces the myeloid biased progeny. Treatment with p38i alone was sufficient to restore lineage balance in untransduced progeny at higher HSPC dosage, but had less effect on transduced HSCs progeny (as was observed with high HSC dose in earlier experiments [FIG. 9]). PGE2 alone was sufficient to restore the lineage skewing, although at the lowest cell doses, where there was a combination of excess cycling and transduction stress, the combination of PGE2 and p38i was most effective at reversing the myeloid skewing and restoring the B lymphoid potential, rather than PGE2 alone (FIG. 20, Panels A-D). Moreover, the total human engraftment in the bone marrow at 24 weeks after 1 T revealed higher engraftment levels with the p38i and PGE2 combination in the higher CD34$^+$ dose groups, where engraftment could be meaningfully analyzed (FIG. 20, Panel E). Furthermore, the competitive repopulating units (CRU) in BM at 6 months were enhanced nearly five-fold with the combination treatment, as compared to the single treatment with p38i or PGE2 (FIG. 20, Panel F). Finally, the assessment of LTRP in 2 T mice at 3 months showed the effect of the p38i and PGE2 combination treatment, at increasing both the LTRP and reversal of the myeloid skewed phenotype (FIG. 20, Panels G, I-L). It is to be noted that the use of p38i or PGE2 or the combination did not have any effect in the GFP marking, even in the long-termed secondary human grafts (FIG. 20, Panel H).

DISCUSSION

Presented herein are important and distinct mechanisms by which in vitro genetic manipulation of HSCs results in HSC loss and fate change. p38 stress signaling has been shown to be induced by ROS[37]. It is shown in this study that p38 activation increases the DDR, which reduces the LTRP of HSCs. The present study also explains the mechanism of increase DDR in HSCs with exit from dormancy and the resultant HSC attrition seen in vivo in mouse HSCs[69], and shows that the DDR response is further exaggerated by gene transfer-mediated DSB, which is also reduced with p38 inhibition.

In addition, it is shown herein that the DNA-DSBs, induced by vector integrase or gene editing nucleases in cycling HSCs destabilize HIF-1α and evoke Chk1/p38-mediated $G_2M$ checkpoint, altering the cell cycle progression of HSC, which appears to age/exhaust HSC (increased numbers of HSCs that have poor LTRP, a myeloid biased progeny and upregulation of Wnt signaling). While the data presented herein supports p38 as a non-canonical checkpoint kinase in 'cycling HSC', where it acts in concert with Chk1 to evoke the $G_2M$ checkpoint, increased p38 signaling may also hasten 'quiescent HSCs' into cycle, since p38 inhibition increases HSCs in $G_0$ phase. The rapid transition of HSCs from $G_0$ phase into active cell cycle alters their fate to HPCs, which have reduced LTRP. Cell cycle and cell fate have been intimately linked through chromatin remodeling in many stem cell types[85]. The data presented herein reveals that alteration in specific cell-cycle phase duration during the first HSC division in vitro is sufficient to alter human HSC lineage fate and LTRP.

Further, it was found in this study that either PGE2 or Chk1 is required concomitant p[38] inhibition to significantly abrogate the $G_2M$ accumulation, and more importantly, to reduce DDR in HSCs, and these combined effects improved the CRU potential of cycling adult HSCs by nearly five-fold. It is also contemplated that PGE2 mediates survival of the lymphoid-biased HSCs, which are more vulnerable to genotoxic stress[73]. Regardless, the study presented herein provides critical mechanistic insight based solution for both vector-mediated gene transfer or nuclease mediated gene correction of cycling HSCs, and ways to prevent alteration of their lineage fate and LTRP.

Additionally, it was observed that DDR is activated even in non-cycling, genetically manipulated-HSCs, but HSCs appear much more tolerant of this genotoxic stress when quiescent. Hence GE methodologies geared towards gene disruption via NHEJ could be targeted to quiescent HSCs without sustaining the genotoxic stress associated with GE of cycling HSC; and here, p38i can dampen the DDR and likely reduce the regenerative stress. From a translational perspective, these studies presented herein explain the basis of the outcomes of RV and LV GT trials, and explain the poor in vivo engraftment of gene targeted HSPCs (where HDR occurs in cycling HSC), despite high in vitro gene editing efficiencies.

In summary, by identifying the mechanism of loss of LTRP and HSC fate change with gene transfer, presented herein are important insights into gene transfer/repair at different cell-cycle phase of HSCs; and also the means of genetic manipulation of cycling HSCs by inhibition of p38 stress signaling and stabilization of HIF-1α, that is applicable to vector-mediated and GE-mediated HDR.

Exemplary Methods

Human CD34+ Cell Isolation, Culture and Transduction

Fresh G-CSF mobilized peripheral blood cells were collected via apheresis from normal healthy volunteers (with informed consent obtained from all subject) using an IRB approved protocol, and were subjected to a positive selection using anti-CD34 antibody on the CLINIMACS® (Miltenyi Biotech, Germany) or Indirect CD34 Micro Bead Kit, human (Miltenyi Biotech, Inc. Bisley, Germany) as described previously[21] to a greater than 95% purity. Fresh or cryopreserved CD34+ was used freshly for ex vivo culture and transduction. For controls, freshly isolated CD34+ cells were immediately transplanted into NSG mice. In some experiments, normal bone marrow donor derived CD34+ cells were purchased.

Freshly isolated CD34+ cells were used, wherever possible, and especially for 0 h controls. In some experiments cryopreserved CD34+ cells were thawed for 4 hrs in IMDM containing cytokines, then washed and used for experiments. CD34+ cells were transduced in X-VIVO 10™ (Lonza) medium supplemented with 2% human serum albumin (Baxter), recombinant human Flt-3 ligand (Flt3-L; 200 ng/mL), stem cell factor (SCF; 300 ng/mL), thrombopoietin (TPO; 100 ng/mL) (all cytokines obtained from PeproTech), and penicillin-streptomycin (ThermoFisher Scientific) on non-tissue culture treated plates coated with retronectin (4 µg/cm2, CH-296, Takara Bio Inc.). For LV transduction, CD34+ cells (2-5×10$^6$/mL) were pre-stimulated for 4-8 hours and transduced twice with lentivirus vector (LV) maintaining the vector concentration between 5×10$^7$ to 1×10$^8$ infectious unit (IU) per mL of media volume, 12-14 hours apart. Cells were kept in culture for a total of either 18-24 hours, 36-42 hours or 72-96 hours. For RV transduction, human CD34+ cells were pre-stimulated for ~2 days (42-48 hours) hours at a cell density of 3×10$^5$ cells/ml. Retronectin coated tissue culture flasks or plates were pre-loaded at room temperature with GALV pseudotyped RV twice for one hour each. The vector supernatant was removed and the cells were loaded into the RV loaded retronectin coated flasks. RV transduction was also performed twice 24 hours apart at an MOI ranging from 5 to 10. After total of 72-96 hours in culture, cells were harvested. LV and RV transductions were performed at 37° C. under 5% $CO_2$ in ambient oxygen concentrations (20% 02). For some experiments, LV was added just like RV after 2 days of pre-stimulation. p38 MAPK inhibitors Birb 796 (600 nM), Vx-745 (1 µM), or LY 2228820 (500 nM) (all from Selleckchem) were supplemented to the culture media. The Chk1 inhibitor: MK-8776 (1 µM) (Selleckchem S2735) or Chk2 Inhibitor: PV1019 (1 µM) (Calbiochem 220488) were added only with transductions; 16,16 dimethyl Prostaglandin E2 (PGE2) (10 µM) (Cayman) was added at the beginning of culture, at first transduction and one hour before harvest. N-acetyl cysteine amide (NACA) (Sigma A0737) was used in the concentrations as described.

Following transduction, cells were harvested and washed and resuspended in PBS, and injected intravenously (1×10$^6$ cells per mouse) into NSG mice that had received 280 cGy radiation, using a 135Cs source (Mark I Model 68A Irradiator, J.L. Shepherd and Associates, San Fernando, Calif.). In some experiments, a portion of the cells were plated on METHOCULT™ GF 4434 (Stem Cell Technologies, Vancouver, Canada) to determine the gene transfer efficiency at day 14 in colony forming unit-cells (CFC), and in liquid cultures to estimate the percentage of eGFP+ cells at day 7.

Xeno-Transplantation

NOD.Cg-Prkdcscid Il2rgtm1Wjl/SzJ (NSG) mice were purchased from The Jackson Laboratory (Bar Harbor, Me.). All animals were bred and maintained in a specific pathogen-free environment and all experiments were approved by the Institutional Animal Care and Use (IACUC) Committee. Male and female NSG mice aged 8 to 14 weeks old were fed doxycycline chow (TestDiet; Modified Prolab RMH-1500 with 0.0625% doxycycline) a week prior to, during and for 2 weeks post irradiation. Human engraftment was analyzed in bone marrow (BM), via BM aspirates performed at 6 and 12 weeks from left and right femurs. After sacrifice at 24 weeks, marrow from all of the primary mice (1 T) was harvested. Peripheral blood analysis was also performed in some experiments. Secondary transplants (2 T) were performed after mouse CD45+ cells were depleted from BM harvested from each 1 T mouse separately, using Biotin Rat Anti-Mouse CD45 (BD Biosciences 553078) and Streptavidin Particles Plus-DM (BD Biosciences 557812) and injected into one irradiated (280 cGy) secondary NSG mouse. For calculating competitive repopulating units (CRU) from limiting dilution transplantation, the L-CAL-C$^T$M software (Stem Cell Technologies) was used. All of the mice used for this study were randomly assigned to a treatment group. No animals were excluded from the analysis.

Lentivirus and γ-Retrovirus Vector Constructs

Lentiviral vector (LV) pRRL.SIN.cPPT.MNDU3.eGFP.WPRE[86] encodes the enhanced green fluorescent protein (GFP) under the control of MNDU3 promoter. The vector was packaged using the VSV-G envelope. The retroviral vector (RV) pSRS11.EFS.GFP.PRE (GALV)[87] encodes GFP under the control of a short EFlu (EFS) promoter, and was packaged using the GALV envelope.

Flow Cytometry Analyses

PE-Cyanine 7 or APC-EFLUOR® 780, APC- or PE-conjugated antibodies directed to human CD34 (BD Biosciences 560710 or 555824), CD38 (eBiosciences, San Diego, Calif. 47-0389-42), CD90 (BioLegend 328120), CD45RA (eBiosciences 17-0458-42), CD49f (BD Biosciences 555736), CD45 (BD 55485 or Biolegend 304026), CD33 (eBiosciences 25-0338-42), CD19 (BD Biosciences 557791), or CD3 (BD Biosciences 555340). Cells (~5×10$^5$–1×10$^6$) were used to label with antibodies as per manufacturer instructions with the appropriate isotype controls. For phospho-flow, primary antibodies phospho-p38 (Thr180/Tyr182; 4092S), phospho-p44/42 MAPK (ERK ½) (Thr202/Tyr204; 4094S), and phospho-JNK (Thr183-Tyr185 PE conjugate; 5755S) (all from Cell Signaling) were used for staining overnight followed by wash and secondary antibody stain including Goat anti-Rabbit IgG (H+L) or Goat anti-Rabbit IgG (H+L) or Pacific Blue (P-10994) antibody. Apoptosis assay was performed using PE Annexin V Apoptosis Detection Kit (BD Biosciences 559763) according to the manufacturer's instructions. Total ROS and mitochondrial specific ROS were detected using 10 µM CM-H2DCFDA (ThermoFisher Scientific C6827) and 5 µM MITOSOX™ Red (Red Mitochondrial Superoxide Indicator) (ThermoFisher Scientific M36008) respectively, following manufacturer's instructions.

For cell cycle analysis, cells were first labeled with surface markers, fixed and permeabilized using BD Fixation/Permeabilization solution (BD Biosciences 554714) and then stained with PerCP-Cy™5.5 anti-Ki-67 (BD Biosciences 561284), ALEXA FLUOR® 647 anti-Ki-67 (BD Biosciences 558615) and Hoechst 33342 (Sigma-Aldrich B2261) at 10 µg/mL, as described previously[88]. For EdU incorporation assay, cells were incubated with 10 µM EdU throughout the culture period and the CLICK-IT® Plus EdU Pacific Blue Flow Cytometry Assay Kit (ThermoFisher Scientific C10636) was used for staining. For DDR detection, fixed and permeabilized cells were stained with PE mouse anti-H2AX (pS139) (BD Biosciences 562377). Samples were run through a FACSCANTO™, FORTESSA™, or LSR 2 flow cytometers (BD Biosciences), and the data was analyzed by FACSDIVA™ software (BD). In some experiments, cells were stained with the appropriate antibodies as stated above and then sorted using BD FACSARIA™ II cell sorter.

Immunofluorescence

FACS sorted CD34+38−90+ cells were fixed in 2% paraformaldehyde and permeabilized using 0.1% TRITON™ X-100 (Alkaryl polyether alcohol, Sigma-Aldrich). Cells were then stained with primary antibodies Anti-phospho-H2AX (Ser 139) (Millipore, 05-636), anti-53BP1 antibody (Novus Biologicals, NB100-904), or anti-HIF-1α (ab103063). For secondary antibodies, Alexa Fluor 594 conjugated Goat anti-Rabbit IgG (H+L) (A-11037) or, ALEXA FLUOR® 647 conjugated Goat anti-Rabbit IgG (H+L) (A-21245) (both from ThermoFisher Scientific) were used for 1 hour at 37° C. Cells were counterstained and mounted with VECTASHIELD® antifade mounting medium with DAPI (H-1200 Vector Laboratories). Images were obtained using a Nikon 90i upright microscope.

Nucleoporation of Cas9/gRNA RNP in Human CD34+ Cells

CD45 sgRNA was synthesized by assembly PCR and in vitro-transcription using the GENEART® Precision gRNA Synthesis Kit. The quality of the sgRNA sample was determined by running it on a 10% NOVEX™ TBE-Urea Gel and a discreet band at 100 bases indicated intact sgRNA. Cas9 buffer was prepared with 20 mM HEPES pH 7.5, 150 mM KCl, 1 mM MgCl2, 10% glycerol and 1 mM TCEP. Thawed and 44 hours pre-stimulated human MPB derived CD34+ cells were subjected to nucleofection with Cas9 RNPs. Cas9 RNPs were assembled immediately prior to nucleofection of CD34+ cells as described previously[29]. To nucleofect a 20 µL cell suspension (150,000-200,000 cells) with Cas9 RNP, a 5 µL solution containing 120 pmol of sgRNA in Cas9 buffer was prepared. A 5 µL solution containing 100 pmol Cas9 protein in Cas9 buffer was prepared and added to the sgRNA solution slowly over ~30 seconds, and incubated at room temperature for 20 minutes. For each nucleofection, 150,000 to 200,000 CD34+ cells were re-suspended in 20 µL P3 solution (Lonza), and mixed with 10 µL Cas9 RNP. This mixture was then nucleofected using the LONZA 4D NUCLEOFECTOR® using the E0100 program. Nucleofected cells were recovered in fresh medium (supplemented with human cytokines as described above) and cultured at 37° C. for further time periods. Cells were harvested at 6 and 24 hours post-nucleofection for cell cycle staining. The remaining cells were cultured for 5-8 additional days prior to genotyping and CD45 staining for flow cytometry.

Quantitative PCR Analyses

RNAseq analysis was performed on RNA from FACS sorted cultured and transduced CD34+38−90+45RA−49f+ HSC at 24 h and 72 h with and without treatment with p38i in one experiment. For qRT PCR, cultured and transduced cells were harvested and sorted for CD34+CD38-CD90+ markers using FACSARIA™ cell sorter (BD) directly into-TRI REAGENT® (guanidine, thiocyanate, and phenol solution, Molecular Research Center, Inc.). Total RNA was purified with phase separation by chloroform and precipitation by isopropanol. cDNA was generated using the SUPERSCRIPT™ IV VILO™ Master Mix (ThermoFisher Scientific 11756050). The cDNA was amplified by qPCR using the primer/probe sets as follows: FZD3 Hs00184043_m1, WNT5B Hs01086864_m1, p34 CDC2 Hs00938777_m1 (ABI/ThermoFisher, 4331182) and analyzed on ABI 7900 Fast Real-time PCR system. The master mix used for qPCR set up was ITAQ™ Universal Probes Supermix (BioRad 1725134). Gene expression level was calculated using ΔΔCt method, normalized to human glyceraldehyde-3-phosphate dehydrogenase (GAPDH) (ABI/ThermoFisher).

Statistical Analyses

Data are expressed as mean±standard error of the mean (SEM). Depending upon the groups, data was analyzed by using two-tailed Mann-Whitney U test, paired Student's t-test or Wilcoxon test, log rank test as indicated in the figure legends, using the GRAPHPAD PRISM® (V.7) software. Since pairwise comparison between two groups was performed, multiple comparison test were not used. P values ≤0.05 were considered significant.

REFERENCES CITED IN EXAMPLES

1 Hacein-Bey-Abina, S. et al. Insertional oncogenesis in 4 patients after retrovirus-mediated gene therapy of SCID-X1. *J Clin Invest* 118, 3132-3142 (2008).
2 Ginn, S. L. et al. Lymphomagenesis in SCID-X1 mice following lentivirus-mediated phenotype correction independent of insertional mutagenesis and gammac overexpression. *Mol Ther* 18, 965-976, doi:10.1038/mt.2010.50 (2010).
3 Negre, O. et al. Preclinical evaluation of efficacy and safety of an improved lentiviral vector for the treatment of beta-thalassemia and sickle cell disease. *Curr Gene Ther* 15, 64-81 (2015).
4 Imren, S. et al. High-level beta-globin expression and preferred intragenic integration after lentiviral transduction of human cord blood stem cells. *The Journal of clinical investigation* 114, 953-962 (2004).
5. Imren, S. et al. Permanent and panerythroid correction of murine beta thalassemia by multiple lentiviral integration in hematopoietic stem cells. *Proceedings of the National Academy of Sciences of the United States of America* 99, 14380-14385 (2002).
6 Pawliuk, R. et al. Correction of sickle cell disease in transgenic mouse models by gene therapy. *Science* 294, 2368-2371 (2001).
7 May, C. et al. Therapeutic haemoglobin synthesis in beta-thalassaemic mice expressing lentivirus-encoded human beta-globin. *Nature* 406, 82-86 (2000).
8 Rivella, S., May, C., Chadburn, A., Riviere, I. & Sadelain, M. A novel murine model of Cooley anemia and its rescue by lentiviral-mediated human beta-globin gene transfer. *Blood* 101, 2932-2939 (2003).
9 Persons, D. A., Hargrove, P. W., Allay, E. R., Hanawa, H. & Nienhuis, A. W. The degree of phenotypic correction of murine beta-thalassemia intermedia following lentiviral-mediated transfer of a human gamma-globin gene is influenced by chromosomal position effects and vector copy number. *Blood* 101, 2175-2183 (2003).
10. Pestina, T. I. et al. Correction of murine sickle cell disease using gamma-globin lentiviral vectors to mediate high-level expression of fetal hemoglobin. *Mol Ther* 17, 245-252 (2009).
11 Puthenveetil, G. et al. Successful correction of the human beta-thalassemia major phenotype using a lentiviral vector. *Blood* 104, 3445-3453 (2004).
12 Arumugam, P. I. et al. Improved human beta-globin expression from self-inactivating lentiviral vectors carrying the chicken hypersensitive site-4 (cHS4) insulator element. *Mol Ther* 15, 1863-1871, doi:10.1038/sj.mt.6300259 (2007).
13 Perumbeti, A. et al. A novel human gamma-globin gene vector for genetic correction of sickle cell anemia in a humanized sickle mouse model: critical determinants for successful correction. *Blood* 114, 1174-1185, doi:10.1182/blood-2009-01-201863 (2009).
14 Kiem, H. P. et al. Pigtailed macaques as a model to study long-term safety of lentivirus vector-mediated gene therapy for hemoglobinopathies. *Mol Ther Methods Clin Dev* 1, 14055, doi:10.1038/mtm.2014.55 (2014).
15 Romero, Z. et al. beta-globin gene transfer to human bone marrow for sickle cell disease. *J Clin Invest*, doi:10.1172/JCI67930 (2013).
16 Akala, O. O. & Clarke, M. F. Hematopoietic stem cell self-renewal. *Curr Opin Genet Dev* 16, 496-501 (2006).
17 Orford, K. W. & Scadden, D. T. Deconstructing stem cell self-renewal: genetic insights into cell-cycle regulation. *Nature reviews* 9, 115-128 (2008).
18 Morrison, S. J. & Kimble, J. Asymmetric and symmetric stem-cell divisions in development and cancer. *Nature* 441, 1068-1074 (2006).
19 Notta, F. et al. Isolation of single human hematopoietic stem cells capable of long-term multilineage engraftment. *Science* (New York, N. Y.) 333, 218-221, doi:10.1126/science.1201219 (2011).
20 Girard-Gagnepain, A. et al. Baboon envelope pseudotyped LVs outperform VSV-G-LVs for gene transfer into early-cytokine-stimulated and resting HSCs. *Blood* 124, 1221-1231, doi:10.1182/blood-2014-02-558163 (2014).
21 Kang, E. M. et al. Retrovirus gene therapy for X-linked chronic granulomatous disease can achieve stable long-term correction of oxidase activity in peripheral blood neutrophils. *Blood* 115, 783-791, doi:10.1182/blood-2009-05-222760 (2010).
22 Gouble, A. et al. Efficient in toto targeted recombination in mouse liver by meganuclease-induced double-strand break. *J Gene Med* 8, 616-622, doi:10.1002/jgm.879 (2006).
23 Hoban, M. D. et al. Correction of the sickle cell disease mutation in human hematopoietic stem/progenitor cells. *Blood* 125, 2597-2604, doi:10.1182/blood-2014-12-615948 (2015).
24 Urnov, F. D. et al. Highly efficient endogenous human gene correction using designed zinc-finger nucleases. 435, 646-651 (2005).
25 Wang, J. et al. Homology-driven genome editing in hematopoietic stem and progenitor cells using ZFN mRNA and AAV6 donors. *Nature biotechnology* 33, 1256-1263, doi:10.1038/nbt.3408 (2015).
26 Sather, B. D. et al. Efficient modification of CCR5 in primary human hematopoietic cells using a megaTAL nuclease and AAV donor template. *Sci Transl Med* 7, 307ra156, doi:10.1126/scitranslmed.aac5530 (2015).
27 Genovese, P. et al. Targeted genome editing in human repopulating haematopoietic stem cells. *Nature* 510, 235-240, doi:10.1038/nature13420 (2014).
28 Hoban, M. D. et al. CRISPR/Cas9-Mediated Correction of the Sickle Mutation in Human CD34+ cells. *Mol Ther* 24, 1561-1569, doi:10.1038/mt.2016.148 (2016).
29 DeWitt, M. A. et al. Selection-free genome editing of the sickle mutation in human adult hematopoietic stem/progenitor cells. *Sci Transl Med* 8, 360ra134, doi:10.1126/scitranslmed.aaf9336 (2016).
30 Aiuti, A. et al. Lentiviral hematopoietic stem cell gene therapy in patients with Wiskott-Aldrich syndrome. *Science* 341, 1233151, doi:10.1126/science.1233151 (2013).
31 Cartier, N. et al. Hematopoietic stem cell gene therapy with a lentiviral vector in X-linked adrenoleukodystrophy. *Science* 326, 818-823 (2009).
32 Biffi, A. et al. Lentiviral hematopoietic stem cell gene therapy benefits metachromatic leukodystrophy. Science 341, 1233158, doi:10.1126/science.1233158 (2013).
33 Cavazzana-Calvo, M. et al. Transfusion independence and HMGA2 activation after gene therapy of human beta-thalassaemia. *Nature* 467, 318-322, doi:10.1038/nature09328 (2010).
34 Chou, S., Chu, P., Hwang, W. & Lodish, H. Expansion of human cord blood hematopoietic stem cells for transplantation. *Cell stem cell* 7, 427-428, doi:10.1016/j.stem.2010.09.001 (2010).
35 Huang, J., Nguyen-McCarty, M., Hexner, E. O., Danet-Desnoyers, G. & Klein, P. S. Maintenance of hematopoietic stem cells through regulation of Wnt and mTOR pathways. *Nature medicine* 18, 1778-1785, doi:10.1038/nm.2984 (2012).
36 Zou, J. et al. Inhibition of p38 MAPK activity promotes ex vivo expansion of human cord blood hematopoietic stem cells. *Annals of hematology* 91, 813-823, doi:10.1007/s00277-011-1397-7 (2012).
37 Ito, K. et al. Reactive oxygen species act through p38 MAPK to limit the lifespan of hematopoietic stem cells. *Nature medicine* 12, 446-451, doi:10.1038/nm1388 (2006).
38 Zhang, C. C. et al. Angiopoietin-like proteins stimulate ex vivo expansion of hematopoietic stem cells. *Nature medicine* 12, 240-245, doi:10.1038/nm1342 (2006).
39 Hoggatt, J., Singh, P., Sampath, J. & Pelus, L. M. Prostaglandin E2 enhances hematopoietic stem cell homing, survival, and proliferation. *Blood* 113, 5444-5455, doi:10.1182/blood-2009-01-201335 (2009).
40 Hoggatt, J., Mohammad, K. S., Singh, P. & Pelus, L. M. Prostaglandin E2 enhances long-term repopulation but does not permanently alter inherent stem cell competitiveness. *Blood* 122, 2997-3000, doi:10.1182/blood-2013-07-515288 (2013).
41 North, T. E. et al. Prostaglandin E2 regulates vertebrate haematopoietic stem cell homeostasis. *Nature* 447, 1007-1011, doi:10.1038/nature05883 (2007).
42 Goessling, W. et al. Prostaglandin E2 enhances human cord blood stem cell xenotransplants and shows long-term safety in preclinical nonhuman primate transplant models. *Cell Stem Cell* 8, 445-458, doi:10.1016/j.stem.2011.02.003 (2011).
43 Boitano, A. E. et al. Aryl hydrocarbon receptor antagonists promote the expansion of human hematopoietic stem cells. *Science* 329, 1345-1348, doi:10.1126/science.1191536 (2010).

44 Wagner, J. E., Jr. et al. Phase I/II Trial of StemRegenin-1 Expanded Umbilical Cord Blood Hematopoietic Stem Cells Supports Testing as a Stand-Alone Graft. *Cell Stem Cell* 18, 144-155, doi:10.1016/j.stem.2015.10.004 (2016).

45 Fares, I. et al. Cord blood expansion. Pyrimidoindole derivatives are agonists of human hematopoietic stem cell self-renewal. *Science* 345, 1509-1512, doi:10.1126/science.1256337 (2014).

46 Chen, X. et al. G9a/GLP-dependent histone H3K9me2 patterning during human hematopoietic stem cell lineage commitment. *Genes Dev* 26, 2499-2511, doi:10.1101/gad.200329.112 (2012).

47 Hao, Q. L., Shah, A. J., Thiemann, F. T., Smogorzewska, E. M. & Crooks, G. M. A functional comparison of $CD34^+$ CD38- cells in cord blood and bone marrow. *Blood* 86, 3745-3753 (1995).

48 Bakker, S. T. & Passegue, E. Resilient and resourceful: genome maintenance strategies in hematopoietic stem cells. *Exp Hematol* 41, 915-923, doi:10.1016/j.exphem.2013.09.007 (2013).

49 Cuadrado, A. & Nebreda, A. R. Mechanisms and functions of p38 MAPK signalling. *The Biochemical journal* 429, 403-417, doi:10.1042/bj20100323 (2010).

50 Baudet, A. et al. RNAi screen identifies MAPK14 as a druggable suppressor of human hematopoietic stem cell expansion. *Blood* 119, 6255-6258, doi:10.1182/blood-2012-01-403949 (2012).

51 Goessling, W. et al. Genetic interaction of PGE2 and Wnt signaling regulates developmental specification of stem cells and regeneration. *Cell* 136, 1136-1147, doi:10.1016/j.cell.2009.01.015 (2009).

52 Cutler, C. et al. Prostaglandin-modulated umbilical cord blood hematopoietic stem cell transplantation. *Blood* 122, 3074-3081, doi:10.1182/blood-2013-05-503177 (2013).

53 Mendelson, A. & Frenette, P. S. Hematopoietic stem cell niche maintenance during homeostasis and regeneration. *Nature medicine* 20, 833-846, doi:10.1038/nm.3647 (2014).

54 Thornhill, S. I. et al. Self-inactivating gammaretroviral vectors for gene therapy of X-linked severe combined immunodeficiency. *Mol Ther* 16, 590-598 (2008).

55 Zychlinski, D. et al. Physiological promoters reduce the genotoxic risk of integrating gene vectors. *Mol Ther* 16, 718-725 (2008).

56 Hacein-Bey-Abina, S. et al. A modified gamma-retrovirus vector for X-linked severe combined immunodeficiency. *N Engl J Med* 371, 1407-1417, doi:10.1056/NEJMoa1404588 (2014).

57 De Ravin, S. S. et al. Lentiviral hematopoietic stem cell gene therapy for X-linked severe combined immunodeficiency. *Sci Transl Med* 8, 335ra357, doi:10.1126/scitranslmed.aad8856 (2016).

58 Zhou, S. et al. Evaluating the Safety of Retroviral Vectors Based on Insertional Oncogene Activation and Blocked Differentiation in Cultured Thymocytes. *Molecular therapy: the journal of the American Society of Gene Therapy* 24, 1090-1099, doi:10.1038/mt.2016.55 (2016).

59 Kelly, P. F. et al. Stem cell collection and gene transfer in Fanconi anemia. *Mol Ther* 15, 211-219 (2007).

60 Sadelain, M. et al. Strategy for a multicenter phase I clinical trial to evaluate globin gene transfer in beta-thalassemia. *Annals of the New York Academy of Sciences* 1202, 52-58, doi:10.1111/j.1749-6632.2010.05597.x (2010).

61 Lewis, P. F. & Emerman, M. Passage through mitosis is required for oncoretroviruses but not for the human immunodeficiency virus. *Journal of virology* 68, 510-516 (1994).

62 Huntsman, H. D. et al. Human hematopoietic stem cells from mobilized peripheral blood can be purified based on CD49f integrin expression. *Blood* 126, 1631-1633, doi:10.1182/blood-2015-07-660670 (2015).

63 Kubota, Y., Takubo, K. & Suda, T. Bone marrow long label-retaining cells reside in the sinusoidal hypoxic niche. *Biochemical and biophysical research communications* 366, 335-339, doi:10.1016/j.bbrc.2007.11.086 (2008).

64 Mantel, C. R. et al. Enhancing Hematopoietic Stem Cell Transplantation Efficacy by Mitigating Oxygen Shock. *Cell* 161, 1553-1565, doi:10.1016/j.cell.2015.04.054 (2015).

65 McGuire, V. A. et al. Cross talk between the Akt and p38alpha pathways in macrophages downstream of Toll-like receptor signaling. *Molecular and cellular biology* 33, 4152-4165, doi:10.1128/mcb.01691-12 (2013).

66 Campbell, R. M. et al. Characterization of LY2228820 dimesylate, a potent and selective inhibitor of p38 MAPK with antitumor activity. *Molecular cancer therapeutics* 13, 364-374, doi:10.1158/1535-7163.mct-13-0513 (2014).

67 Pargellis, C. et al. Inhibition of p38 MAP kinase by utilizing a novel allosteric binding site. *Nature structural biology* 9, 268-272, doi:10.1038/nsb770 (2002).

68 Skalka, A. M. & Katz, R. A. Retroviral DNA integration and the DNA damage response. *Cell death and differentiation* 12 Suppl 1, 971-978, doi:10.1038/sj.cdd.4401573 (2005).

69 Walter, D. et al. Exit from dormancy provokes DNA-damage-induced attrition in haematopoietic stem cells. *Nature* 520, 549-552, doi:10.1038/nature14131 (2015).

70 Florian, M. C. et al. A canonical to non-canonical Wnt signalling switch in haematopoietic stem-cell ageing. *Nature* 503, 392-396, doi:10.1038/nature12631 (2013).

71 Geiger, H., de Haan, G. & Florian, M. C. The ageing haematopoietic stem cell compartment. *Nature reviews. Immunology* 13, 376-389, doi:10.1038/nri3433 (2013).

72 Khoo, M. L. et al. Gene profiling reveals association between altered Wnt signaling and loss of T-cell potential with age in human hematopoietic stem cells. *Aging cell* 13, 744-754, doi:10.1111/acel.12229 (2014).

73 Wang, J. et al. Per2 induction limits lymphoid-biased haematopoietic stem cells and lymphopoiesis in the context of DNA damage and ageing. *Nature cell biology* 18, 480-490, doi:10.1038/ncb3342 (2016).

74 Iliakis, G., Wang, Y., Guan, J. & Wang, H. DNA damage checkpoint control in cells exposed to ionizing radiation. *Oncogene* 22, 5834-5847, doi:10.1038/sj.onc.1206682 (2003).

75 Sartori, A. A. et al. Human CtIP promotes DNA end resection. *Nature* 450, 509-514, doi:10.1038/nature06337 (2007).

76 Jazayeri, A., McAinsh, A. D. & Jackson, S. P. *Saccharomyces cerevisiae* Sin3p facilitates DNA double-strand break repair. *Proc Natl Acad Sci USA* 101, 1644-1649, doi:10.1073/pnas.0304797101 (2004).

77 Byun, T. S., Pacek, M., Yee, M. C., Walter, J. C. & Cimprich, K. A. Functional uncoupling of MCM helicase and DNA polymerase activities activates the ATR-dependent checkpoint. *Genes Dev* 19, 1040-1052, doi:10.1101/gad.1301205 (2005).

78 Pedraza-Alva, G. et al. Activation of p38 MAP kinase by DNA double-strand breaks in V(D)J recombination induces a G2/M cell cycle checkpoint. *EMBO J* 25, 763-773, doi:10.1038/sj.emboj.7600972 (2006).

79 Reinhardt, H. C. & Yaffe, M. B. Kinases that control the cell cycle in response to DNA damage: Chk1, Chk2, and MK2. *Curr Opin Cell Biol* 21, 245-255, doi:10.1016/j.ceb.2009.01.018 (2009).

80 Takubo, K. et al. Regulation of the HIF-1alpha level is essential for hematopoietic stem cells. *Cell stem cell* 7, 391-402, doi:10.1016/j.stem.2010.06.020 (2010).

81 Wirthner, R., Wrann, S., Balamurugan, K., Wenger, R. H. & Stiehl, D. P. Impaired DNA double-strand break repair contributes to chemoresistance in HIF-1 alpha-deficient mouse embryonic fibroblasts. *Carcinogenesis* 29, 2306-2316, doi:10.1093/carcin/bgn231 (2008).

82 Speth, J. M., Hoggatt, J., Singh, P. & Pelus, L. M. Pharmacologic increase in HIFIalpha enhances hematopoietic stem and progenitor homing and engraftment. *Blood* 123, 203-207, doi:10.1182/blood-2013-07-516336 (2014).

83 Tesio, M. et al. Hematopoietic stem cell quiescence and function are controlled by the CYLD-TRAF2-p38MAPK pathway. *The Journal of experimental medicine* 212, 525-538, doi:10.1084/jem.20141438 (2015).

84 Wang, Y., Kellner, J., Liu, L. & Zhou, D. Inhibition of p38 mitogen-activated protein kinase promotes ex vivo hematopoietic stem cell expansion. *Stem cells and development* 20, 1143-1152, doi:10.1089/scd.2010.0413 (2011).

85 Ma, Y., Kanakousaki, K. & Buttitta, L. How the cell cycle impacts chromatin architecture and influences cell fate. *Frontiers in genetics* 6, 19, doi:10.3389/fgene.2015.00019 (2015).

86 Robert-Richard, E. et al. Murine Retroviral but not Human Cellular Promoters Induce In vivo Erythroid-specific Deregulation that can be Partially Prevented by Insulators. *Mol Ther* 15, 173-182 (2007).

87 Arumugam, P. I. et al. Genotoxic potential of lineage-specific lentivirus vectors carrying the beta-globin locus control region. *Mol Ther* 17, 1929-1937, doi:mt2009183 [pii] 10.1038/mt.2009.183 (2009).

88 Wilson, A. et al. Hematopoietic stem cells reversibly switch from dormancy to self-renewal during homeostasis and repair. *Cell* 135, 1118-1129, doi:10.1016/j.cell.2008.10.048 (2008).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for preparing hematopoietic stem cells (HSCs), the method comprising:
    culturing a first population of HSCs in the presence of an effective amount of a p38 mitogen—activated protein kinase (MAPK) inhibitor and an effective amount of a hypoxia inducible factor-1a (HIF-1α) stabilizer to produce a second population of HSCs, wherein the second population of HSCs has enhanced engraftment activity relative to HSCs cultured in the absence of the p38 MAPK inhibitor or the HIF-1α stabilizer;
    wherein the MAPK inhibitor is selected from the group consisting of Birb-796, VX-745, and Ly2228820, and the HIF-1α stabilizer is prostaglandin E2 (PGE2), or 16-16 dimethyl prostaglandin E2 (dmPGE2).

2. The method of claim 1, wherein the first population of HSCs has undergone a genetic manipulation that induces a DNA double strand break.

3. The method of claim 2, wherein the genetic manipulation comprises transduction of an integrating vector.

4. The method of claim 3, wherein the integrating vector is a viral vector.

5. The method of claim 4, wherein the viral vector is a retroviral vector or a lentiviral vector.

6. The method of claim 2, wherein the genetic manipulation comprises genome editing.

7. The method of claim 1, wherein the first population of HSCs are dividing HSCs.

8. The method of claim 1, wherein the first population of HSCs are obtained from a subject.

9. The method of claim 8, wherein the subject is a human subject.

10. The method of claim 9, wherein the first population of HSCs are adult HSCs obtained from bone marrow or peripheral blood cells of the human subject.

11. The method of claim 9, wherein the first population of HSCs are obtained from umbilical cord blood cells of the human subject.

12. The method of claim 1, further comprising administering the second population of HSCs to a subject in need thereof.

13. The method of claim 12, wherein a dose of about 50,000 to about 500,000 HSCs is administered to the subject.

14. The method of claim 13, wherein a dose of about 50,000 to about 100,000 HSCs is administered to the subject.

15. The method of claim 12, wherein the subject is the same subject from whom the first population of HSCs is obtained.

16. The method of claim 1, wherein the culturing step is performed for 1 to 7 days.

17. The method of claim 1, wherein the MAPK inhibitor is at a concentration of 300 nM to 3 µM; and/or wherein the HIF-1α stabilizer is at a concentration of 5 µM to 20 µM.

18. The method of claim 1, wherein the HSCs are human $CD34^+$ HSCs.

* * * * *